(12) United States Patent
Kao et al.

(10) Patent No.: US 12,173,080 B1
(45) Date of Patent: *Dec. 24, 2024

(54) PREVENTION OF DISULFIDE BOND REDUCTION DURING RECOMBINANT PRODUCTION OF POLYPEPTIDES

(71) Applicant: Genentech, Inc., South San Francisco, CA (US)

(72) Inventors: Yung-Hsiang Kao, San Mateo, CA (US); Michael W. Laird, San Ramon, CA (US); Melody Trexler Schmidt, Danville, CA (US); Rita L. Wong, Redwood City, CA (US); Daniel P. Hewitt, Sunnyvale, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/824,681

(22) Filed: Sep. 4, 2024

Related U.S. Application Data

(60) Division of application No. 18/648,209, filed on Apr. 26, 2024, which is a division of application No. 18/194,471, filed on Mar. 31, 2023, now Pat. No. 12,098,211, which is a continuation of application No. 17/087,313, filed on Nov. 2, 2020, now Pat. No. 11,639,395, which is a continuation of application No. 16/847,317, filed on Apr. 13, 2020, now Pat. No. 10,906,986, which is a continuation of application No. 16/240,592, filed on Jan. 4, 2019, now Pat. No. 10,759,866, which is a continuation of application No. 15/488,917, filed on Apr. 17, 2017, now abandoned, which is a division of application No. 14/043,758, filed on Oct. 1, 2013, now abandoned, which is a division of application No. 13/354,223, filed on Jan. 19, 2012, now Pat. No. 8,574,869, which is a continuation of application No. 12/217,745, filed on Jul. 8, 2008, now abandoned.

(60) Provisional application No. 60/948,677, filed on Jul. 9, 2007.

(51) Int. Cl.
C07K 16/28 (2006.01)
A61K 39/395 (2006.01)
C07K 1/14 (2006.01)

(52) U.S. Cl.
CPC ..... *C07K 16/2887* (2013.01); *A61K 39/39591* (2013.01); *C07K 1/14* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,049,494 A | 9/1977 | Tomei |
| 4,560,655 A | 12/1985 | Baker |
| 4,572,798 A | 2/1986 | Koths et al. |
| 4,620,948 A | 11/1986 | Builder et al. |
| 4,652,630 A | 3/1987 | Bentle et al. |
| 4,767,704 A | 8/1988 | Cleveland et al. |
| 5,122,469 A | 6/1992 | Mather et al. |
| 5,252,708 A | 10/1993 | Abecassis et al. |
| 5,380,826 A | 1/1995 | Castor et al. |
| 5,808,006 A | 9/1998 | Builder et al. |
| 5,830,761 A | 11/1998 | Drapeau et al. |
| 5,866,362 A | 2/1999 | Cousens et al. |
| 6,048,728 A | 4/2000 | Inlow et al. |
| 6,127,526 A | 10/2000 | Blank |
| 6,207,802 B1 | 3/2001 | Zsebo et al. |
| 6,309,861 B1 | 10/2001 | Ambrosius et al. |
| 6,566,514 B1 | 5/2003 | Wright et al. |
| 6,590,072 B2 | 7/2003 | Diers |
| 6,872,563 B1 | 3/2005 | Beckwith et al. |
| 7,041,479 B2 | 5/2006 | Swartz et al. |
| 7,153,426 B2 | 12/2006 | Van Reis |
| 7,189,811 B2 | 3/2007 | Panda et al. |
| 7,521,210 B2 | 4/2009 | Knudsen |
| 7,723,490 B2 | 5/2010 | Treuheit et al. |
| 8,574,869 B2 | 11/2013 | Kao et al. |
| 9,284,371 B2 | 3/2016 | Pla et al. |
| 10,759,866 B2 | 9/2020 | Kao et al. |
| 10,808,037 B1 | 10/2020 | Kao et al. |
| 10,906,986 B2 | 2/2021 | Kao et al. |
| 11,078,294 B2 | 8/2021 | Kao et al. |
| 11,639,395 B2 | 5/2023 | Kao et al. |

(Continued)

FOREIGN PATENT DOCUMENTS

| | | |
|---|---|---|
| CA | 2666607 C | 10/2008 |
| CN | 1272550 A | 11/2000 |

(Continued)

OTHER PUBLICATIONS

Adams, C. et al. (2008). "Structural and Functional Analysis of the Interaction Between the Agonistic Monoclonal Antibody Apomab and the Proapoptotic Receptor DR5," *Cell Death and Differentiation* 15:751-761.

Adlersberg, J.B. (1976). "The Immunoglobulin Hinge (Interdomain) Region," *La Ricerca Clin. Lab.* 6:191-205.

(Continued)

*Primary Examiner* — Manjunath N Rao
*Assistant Examiner* — Jae W Lee
(74) *Attorney, Agent, or Firm* — Morrison & Foerster LLP

(57) ABSTRACT

The invention concerns methods for preventing the reduction of disulfide bonds during the recombinant production of disulfide-containing polypeptides. In particular, the invention concerns the prevention of disulfide bond reduction during harvesting of disulfide-containing polypeptides, including antibodies, from recombinant host cell cultures.

10 Claims, 40 Drawing Sheets

Specification includes a Sequence Listing.

(56) References Cited

U.S. PATENT DOCUMENTS

| | | | |
|---|---|---|---|
| 11,976,127 B1 | 5/2024 | Kao et al. |
| 11,987,638 B1 | 5/2024 | Kao et al. |
| 11,999,791 B2 | 6/2024 | Kao et al. |
| 12,098,211 B2 | 9/2024 | Kao |
| 2002/0032315 A1 | 3/2002 | Baca et al. |
| 2002/0142984 A1 | 10/2002 | Brigham et al. |
| 2003/0040095 A1 | 2/2003 | Arini et al. |
| 2003/0087372 A1 | 5/2003 | DelaCruz et al. |
| 2003/0152966 A1 | 8/2003 | Alred et al. |
| 2004/0029229 A1 | 2/2004 | Reeves et al. |
| 2004/0138424 A1 | 7/2004 | Takeda et al. |
| 2004/0138428 A1 | 7/2004 | Zapata |
| 2004/0185535 A1 | 9/2004 | Wilson et al. |
| 2005/0019334 A1 | 1/2005 | Treuheit et al. |
| 2005/0038231 A1 | 2/2005 | Fahrner et al. |
| 2005/0100984 A1 | 5/2005 | Opper et al. |
| 2006/0003405 A1 | 1/2006 | Kallmeier et al. |
| 2006/0030022 A1 | 2/2006 | Beckwith et al. |
| 2006/0040348 A1 | 2/2006 | Qin et al. |
| 2006/0105389 A1 | 5/2006 | Kordyum et al. |
| 2006/0142549 A1 | 6/2006 | Takeda et al. |
| 2006/0143549 A1 | 6/2006 | Yasumoto et al. |
| 2006/0194280 A1 | 8/2006 | Dillon et al. |
| 2006/0216790 A1 | 9/2006 | Knudsen |
| 2007/0212733 A1 | 9/2007 | Martin |
| 2007/0292411 A1 | 12/2007 | Salcedo et al. |
| 2009/0053786 A1 | 2/2009 | Kao et al. |
| 2009/0263866 A1 | 10/2009 | Wilson et al. |
| 2013/0017598 A1 | 1/2013 | Kao et al. |
| 2014/0128575 A1 | 5/2014 | Kao et al. |
| 2017/0313780 A1 | 11/2017 | Kao et al. |
| 2019/0135935 A1 | 5/2019 | Kao et al. |
| 2020/0317801 A1 | 10/2020 | Kao et al. |
| 2020/0347145 A1 | 11/2020 | Kao et al. |
| 2021/0095040 A1 | 4/2021 | Kao et al. |
| 2021/0188993 A1 | 6/2021 | Kao et al. |
| 2023/0365704 A1 | 11/2023 | Kao et al. |
| 2024/0132612 A1 | 4/2024 | Kao et al. |
| 2024/0150486 A1 | 5/2024 | Kao et al. |
| 2024/0158527 A1 | 5/2024 | Kao et al. |
| 2024/0301080 A1 | 9/2024 | Kao |

FOREIGN PATENT DOCUMENTS

| | | |
|---|---|---|
| CN | 1756768 A | 4/2006 |
| EP | 0 185 459 A2 | 6/1986 |
| EP | 0 363 126 A2 | 4/1990 |
| EP | 0 414 151 A1 | 2/1991 |
| EP | 0 612 846 A1 | 8/1994 |
| EP | 0 656 064 B1 | 3/1997 |
| EP | 1 228 076 B1 | 8/2002 |
| EP | 1 241 250 A2 | 9/2002 |
| EP | 2 188 302 B1 | 5/2010 |
| EP | 2 586 788 B1 | 5/2013 |
| GB | 2 237 288 A | 5/1991 |
| GB | 2 251 249 B | 6/1995 |
| JP | 2002-524104 A | 8/2002 |
| JP | 2005-520569 A | 7/2005 |
| JP | 2010-533192 A | 10/2010 |
| WO | WO-1993/10260 A1 | 5/1993 |
| WO | WO-1994/03603 A1 | 2/1994 |
| WO | WO-96/36358 A1 | 11/1996 |
| WO | WO-1997/26357 A1 | 7/1997 |
| WO | WO-1998/14467 A1 | 4/1998 |
| WO | WO-1998/21234 A2 | 5/1998 |
| WO | WO-1999/33988 A1 | 7/1999 |
| WO | WO-1999/54440 A1 | 10/1999 |
| WO | WO-00/15665 A2 | 3/2000 |
| WO | WO-2000/12537 A1 | 3/2000 |
| WO | WO-2001/021628 A1 | 3/2001 |
| WO | WO-2002/04616 A2 | 1/2002 |
| WO | WO-2002/20818 A1 | 3/2002 |
| WO | WO-2002/068455 A2 | 9/2002 |
| WO | WO-2002/068455 A3 | 9/2002 |
| WO | WO-2003/029442 A1 | 4/2003 |
| WO | WO-03/083056 A2 | 10/2003 |
| WO | WO-03/083056 A3 | 10/2003 |
| WO | WO-2003/102132 A2 | 12/2003 |
| WO | WO-2004/001056 A1 | 12/2003 |
| WO | WO-2004/067556 A1 | 8/2004 |
| WO | WO-2004/069876 A2 | 8/2004 |
| WO | WO-2005/016968 A2 | 2/2005 |
| WO | WO-2005/083058 A1 | 9/2005 |
| WO | WO-2006/034488 A2 | 3/2006 |
| WO | WO-2006/047340 A2 | 5/2006 |
| WO | WO-2006/054063 A1 | 5/2006 |
| WO | WO-2006/060083 A1 | 6/2006 |
| WO | WO-2006/083971 A2 | 8/2006 |
| WO | WO-2006/083971 A3 | 8/2006 |
| WO | WO-2006/084264 A2 | 8/2006 |
| WO | WO-2007/103521 A2 | 9/2007 |
| WO | WO-2008/083288 A2 | 7/2008 |
| WO | WO-2008/121616 A2 | 10/2008 |
| WO | WO-2008/127305 A2 | 10/2008 |
| WO | WO-2008/127305 A3 | 10/2008 |
| WO | WO-2008/135498 A2 | 11/2008 |
| WO | WO-2008/135498 A3 | 11/2008 |
| WO | WO-2009/009523 A2 | 1/2009 |
| WO | WO-2009/009523 A3 | 1/2009 |
| WO | WO-2011/009625 A1 | 1/2011 |
| WO | WO-2015/085003 A1 | 6/2015 |

OTHER PUBLICATIONS

Aiba, S. et al. (1973). "Aeration and Agitation," Chapter 6 in *Biochemical Engineering* 2$^{nd}$ *Ed.*, pp. 186-188, and "Equipment Design and Asepsis," Chapter 11 in *Biochemical Engineering* 2$^{nd}$ *Ed.* pp. 303-306, total pp. 8.

Ajouz, B. et al. (Oct. 9, 1998). "Release of Thioredoxin via the Mechanosensitive Channel MscL During Osmotic Downshock of *Escherichia coli* Cells," *The Journal of Biological Chemistry* 273(41):26670-26674.

Alberts, B. et al. (2002). "Proteins," Chapter 3 in Molecular Biology of The Cell, Fourth Edition, pp. 129-188, and "The Adaptive Immune System," Chapter 24, in in Molecular Biology of The Cell, Fourth Edition, pp. 1363-1421.

Albert, B. et al. (2002). "Proteins," Chapter 3 in *Molecular Biology of the Cell*, pp. 129-157.

Al-Fageeh, M.B. et al. (Apr. 5, 2006, e-pub. Dec. 2, 2005). "The Cold-Shock Response in Cultured Mammalian Cells: Harnessing the Response for the Improvement of Recombinant Protein Production," *Biotechnology and Bioengineering* 93(5):829-835.

Alvi, K. (2007). "Book Reviews: Cell Culture Technology For Pharmaceutical and Cell-Based Therapies," Ozturk, S.S. and Hu, W.-S., eds. CRC Press,*Journal of Natural Products* 70(4):711-713.

Andersen, D.C. et al. (2004). "Production Technologies for Monoclonal Antibodies and Their Fragments," *Current Opinion in Biotechnology* 15:456-462.

Annis, I. et al. (1997). "Disulfide Bond Formation in Peptides," Methods in Enzymology 289:198-221.

AVASTIN Label. (2004). "1.14.1.3, Labeling Text, Avastin™M (Bevacizumab)," 27 pages.

Biogen, Inc. (May 17, 1996). "Summary Basis for Approval AVONEX," Biogen Inc. 32 pages.

Backer, M.P. et al. (Oct. 1988). "Large-Scale Production of Monoclonal Antibodies in Suspension Culture," *Biotechnol. & Bioeng.* 32:993-1000.

Bailey, J.E. (1986). "Transport Phenomena in Bioprocess Systems," Chapter 8 in *Biochemical Engineering Fundamentals*, pp. 457-532 and "Design and Analysis of Biological Reactors," Chapter 9 in *Biochemical Engineering Fundamentals*, pp. 533-657, and "Instrumentation Control," Chapter 10 in in *Biochemical Engineering Fundamentals*, pp. 658-725.

Becker, K. et al. (2000). "Thioredoxin Reductase as a Pathophysiological Factor and Drug Target," *Eur. J. Biochem.* 267:6118-6125.

Berggren, M. et al. (1996). "Thioredoxin and Thioredoxin Reductase Gene Expression in Human Tumors and Cell Lines, and the Effects of Serum Stimulation and Hypoxia," *Anticancer Research* 16:3459-3466.

(56) References Cited

OTHER PUBLICATIONS

Biaglow, J.E. et al. (2005, e-pub. Nov. 16, 2004). "The Thioredoxin Reducatase/Thioredoxin System: Novel Redox Targets for Cancer Therapy," *Cancer Biology& Therapy* 4(1):6-13.
Birch, J.R. et al. (2006, e-pub. May 22, 2006). "Antibody Production," *Advanced Drug Delivery Reviews* 58:671-685.
Bjurstrom, E. et al. (Feb. 18, 1985). "Feature Report. Biotechnology Has Been Described as the Last Great Technical Innovation of the Twentieth Century. Chemical Engineers are Ideally Placed to Bring the Innovation to Fruition. Here We Discuss the Two Main Areas of Interest-Fermentation, and the Subsequent Recovery and Purification of Desirable Products," *Chemical Engineering* pp. 126-148.
Bliem, R. et al. (Sep. 1988). "Scale-Up Engineering in Animal cell technology: Part II," Tibtech 6:224-230.
Bobovnikova, Y. et al. (1997). "Characterization of Soluble, Disulfide Bond-Stabilized Prokaryotically Depressed Human Thryotropin Receptor Ectodomain," *Endocrinology* 138(2):588-593.
Boettcher, M. et al. (May 21, 2015). "Choosing the Right Tool for the Job: RNAi, TALEN, or CRISPR," *Molecular Cell* 58:575-585.
Boraston, R. et al. (1984). "Growth and Oxygen Requirements of Antibody Producing Mouse Hybridoma Cells in Suspension Culture," *5th General Meeting of ESACT*, Copenhagen, Denmark, 1982, *Develop. Biol. Standard*, vol. 55, pp. 103-111.
Borys, M.C. et al. (Jun. 11, 1993). "Culture pH Affects Expression Rates and Glycosylation of Recombinant Mouse Placental Lactogen Proteins by Chinese Hamster Ovary (CHO) Cells," *Nature Publishing* 11:720-724.
Bragadin, M. et al. (2004). "Effect of Metal Complexes on Thioredoxin Reductase and the Regulation of Mitochondrial Permeability Conditions," *Ann. N.Y. Acad. Sci.* 1030:348-354.
Broadwater, J.A. et al. (1999). "Spinach Holo-Acyl Carrier Protein: Overproduction and Prosphopantetheinylation in *Escherichia coli* BL21 (DE3), *in Vitro* Acylation, and Enzymatic Desaturation of Histidine-Tagged Isoform I," *Protein Expression and Purification* 15:314-326.
Burgener, A. et al. (2006). "Medium Development," Chapter 3 in *Cell Culture Technology for Pharmaceutical and Cell-Based Therapies*, Ozturk, S.S. et al. eds., CRC Press, Boca Raton, FL, pp. 41-79.
Butler, M. (2007). "Cell Line Development and Culture Strategies: Future Prospects to Improve Yields," Chapter 1 in Cell Culture and Upstream Processing Taylor and Francis Group, pp. 3-15.
Butler, M. (2005). "Animal Cell Cultures: Recent Achievements and Perspectives in the Production of Biopharmaceuticals," *Appl. Microbiol. Biotechnol.* 68:283-291.
Butler, M. (2004). *Animal Cell Culture and Technology*, Second Edition, BIOS Scientific Publishers Taylor & Francis Group, p. 183.
Cabilly, S. (1989). "Growth at Sub-Optimal Temperatures allows the Production of Functional, Antigen-Biding Fab Fragments in *Escherichia coli*," *Gene* 85:553-557.
Canales, M. et al. (1997). "Large-Scale Production in *Pichia pastoris* of the Recombinant Vaccine GavacTM Against Cattle Tick," *Vaccine* 15(4):414-422.
Carter-Franklin, J.N. et al. (2007, e-pub. Jun. 12, 2007). "Fragments of Protein a Eluted During Protein a Affinity Chromatography," *J. Chromatogr. A* 1163:105-111.
Certified U.S. Appl. No. 60/855,734, filed Nov. 1, 2006, for Romero et al., 55 pages.
Certified the U.S. Appl. No. 60/909,232, filed Mar. 30, 2007, 87 pages.
Chaderjian, W. B. et al. (2005). "Effect of Copper Sulfate on Performance of a Serum-Free CHO Cell Culture Process and the Level of Free Thiol in the Recombinant Antibody Expressed," *Biotechnology Progress* 21(2):550-553.
Chisti, M.Y. et al. (1987). "Airlift Reactors : Characteristics, Applications and Design Considerations," *Chem. Eng. Comm.* 60 :195-242.
Chollangi, S. et al. (Nov. 2015, e-pub. May 6, 2015). "Development of Robust Antibody Purification by Optimizing Protein-A Chromatography in Combination With Precipitation Methodologies," *Biotechnology and Bioengineering* 112(11):2292-2304.

Christansen, J. et al. (1998). "Catalytic and Biophysical Properties of a Nitrogenase Apo-MoFe Protein Produced by *nifB*-Deletion Mutant of *Azotobacter vinelandii*," Biochemistry 37:12611-12623.
Chung, W.K. (Jun. 2017, e-pub. Feb. 10, 2017). "Effects of Antibody Disulfide Bond Reduction on Purification Process Performance and Final Drug Substance Stability," *Biotechnology& Bioengineering* 114(6):1264-1274.
Connors, N.C. (2003). "Mammalian Cell Culture," Chapter 7 in *Handbook of Industrial Cell Culture: Mammalian, Microbial, and Plant Cells*, Vinci, V.A. et al., eds., Humana Press, Totowa, N.J., pp. 171-193.
Conradt, H.S. et al. (Oct. 15, 1989). "Expression of Human Interleukin-2 in Recombinant Baby Hamster Kidney, Ltk, and Chinese Hamster Ovary Cells," *J. Biol. Chem.* 264(29):17368-17373.
Cromwell, M.E.M. et al. (2006). "Protein Aggregation and Bioprocessing," 6*APPS Journal* 8(3):E572-E579.
CUNO. (Apr. 2002). "CUNO Application Brief. Zeta Plus® Depth Filtration and Alternative Technologies, for Cell Culture Clarification," Bioprocess, Biological, & Pharmaceutical, 8 pages.
Curriculum Vitae of Jeffrey Chalmers, (1982-2016), 30 pages.
Curriculum Vitae of Hansjörg Hauser, (1974-2014), 13 pages.
Curriculum Vitae for Arne Holmgren (Aug. 2019), 2 pages.
Davies, D.R. et al. (Dec. 31, 1975). "Three-Dimensional Structure of Immunoglobulins," *Annu. Rev. Biochem.* 44:639-667.
Declaration and Exhibits for Dr. Jeffrey Chalmers, dated Jan. 25, 2019, 628 pages.
Declaration and Exhibits for Dr. Hansjörg Hauser, dated Dec. 21, 2018, 197 pages.
De Jesus, M.J. et al. (2001). "The Influence of pH on Cell Growth and Specific Productivity of Two CHO Cell Lines Producing Human Anti Rh D IgG," in *Animal Cell Technology: From Target Market*, Lindner-Osson, E. et al. eds., Kluwer Academic Publishers, pp. 197-199.
De Kock, S. H. et al. (2004). "Oxygen and Carbon Dioxide Kinetic Challenges for Thermophilic Mineral Bioleaching Processes," *Biochem Soc Trans*. 32(Pt 2):273-275.
Delafuente, G. (1970). "Specific Inactivation of Yeast Hexokinase Induced by Xylose in the Presence of a Phosphoryl Donor Substrate," *Eur. J. Biochem.* 176:240-243.
Donovan, R.S. et al. (2000, e-pub. May 11, 2000). "Optimizing the Expression of a Monoclonal Antibody Fragment Under the Transcriptional Control of the *Escherichia coli lac* Promoter," *Can. J. Microbiol.* 46:532-541.
Dyring, C. et al. (1994). "Observations on the Influence of Glutamine, Asparagine and Peptone on Growth and t-PA Production of Chinese Hamster Ovary (CHO) Cells," *Cytotechnology* 16:37-42.
EMEA. (2007). "Scientific Discussion, ORENCIA" EMEA 36 pages.
Emery, A.N. et al. (1995). "Oxygenation of Intensive Cell-Culture System," *Appl. Microbiol. Biotechnol*. 43:1028-1033.
Encyclopedia of Chinese Chemical Products. (Jan. 2005). Encyclopedia of Chinese Chemical Products, 3rd edition, vol. 3 of 3, Chemical Industry Press, 7 pages in total.
Excerpt from DrugBank showing the HC/LC sequences of Trastuzumab, located at <http://www.drugbank.ca/drugs/DB00072>, last visited on Jun. 25, 2018, 20 pages.
Excerpt of Drugbank entry for Parathyroid Hormone, located at <http://www.drugbank.ca/drugs/DB05829>, last visited on Jul. 17, 2018, 6 pages.
Expert Opinion of Prof. Dr. Arne Holmgren (Aug. 21, 2019), 4 pages. (D129).
Fahey, C. (2002). Thesis—Investigation of Largescale Production and Qualification Methodology of Monoclonal Antibodies (MAbs), Dublin City University, 309 pages.
Fahrner, R.L. et al. (2001, e-pub. Apr. 15, 2013). "Industrial Purification of Pharmaceutical Antibodies: Development, Operation, and Validation of Chromatography Processes," *Biotechnology and Genetic Engineering Rev.* 18:301-327.
Finn, R.K. (1954). "Agitation-Aeration in the Laboratory and in Industry," *Bacteriol. Rev.* 18:254-274.
Fiore, M.M. et al. (Dec. 15, 1992). "An Unusual Antibody that Blocks Tissue Factor/Factor VIIa Function by Inhibiting Cleavage Only of Macromolecular Substrates," *Blood* 80(12):3127-3134.

(56) References Cited

OTHER PUBLICATIONS

Fischer et al. (1993). "Isolation Renaturation and Formation of Disulfide Bonds of Eukaryotic Proteins Expressed in *Escherichia coli* as Inclusion Bodies," *Biotechnology and Bioengineering* 41:3-13.
Fischer, B.E. et al. (1994). "Renaturation of Recombinant Proteins Produced as Inclusion Bodies," *Biotech. Adv.* 12:89-101.
Follman et al. (2004). "Factorial Screening of Antibody Purification Process Using three Chromatography Steps Without Protein A," *Journal of Chromatography A* 1024:79-85.
Fujiki, Y. et al. (Aug. 21, 1980). "Studies on the Disulfide Bonds in Human Pituitary Follicle-Stimulating Hormone," *Biochim. Biphys Acta.* 624(2):428-435. (Abstract Only).
Fujita, J. (1999). "Cold Shock Response in Mammalian Cells," *J. Mol. Microbial. Biotechnol.* 1(2): 243-255.
Gagnon, P. (1996). "Protein A Affinity Chromatography," Chapter 9 in Purification Tools for Monoclonal Antibodies, pp. 157, 161, 172-175, total pp. 10.
Gawlitzek, M. et al. (1995). "Effect of Different Cell Culture Conditions on the Polypeptide Integrity and N-Glycosylation of a Recombinant Model Glycoprotein," *Biotechnology& Bioengineering* 46:536-544.
GEA Mechanical Separation Division. (2005). "Westfalia Separator Industry, Components, Systems, Installations: Pharmaceutical Biotechnology," *GEA Westfalia Separator Industry GmbH* pp. 1-36.
Glockshuber et al. (1992). "The Disulfide Bonds in Antibody Variable Domains: Effects on Stability, Folding in Vitro, and Functional Expression in *Escherichia coli*," Biochemistry 31(5):1270-1279.
Glynn, J. (Mar. 2, 2008). "Process-Scale Precipitation of Impurities in Mammalian Cell Culture Broth," *Biopharm International* 3:1-8.
Gódia, F. et al. (2006). "Cell Metabolism," Chapter 4 in *Cell Culture Technology for Pharmaceutical and Cell-Based Therapies*, Ozturk, S.S. et al. eds., CRC Press, Boca Raton, FL, pp. 81-112.
Gordon, G. et al. (Apr. 1, 1995). "On the Mechanism of Interaction of Steroid with Human Glucose 6-Phosphate Dehydrogenase," *Archives of Biochemistry and Biophysics* 318(1):25-29.
Gray, D.R. (2003, e-pub. Jan. 15, 2003). "Bioreactor Operations-Preparation, Sterilization, Charging, Culture Initiation and Harvesting," *Encyclopedia of Cell Technology*, 52 pages.
Gromer, S. et al. (Jan. 2004). "The Thioredoxin System: From Science to Clinic," *Medicinal Research Reviews* 24(1):40-89.
Transcript of Hansjörg Hauser deposition, Jan. 23, 2019, 80 pages.
Higashi, S. et al. (Oct. 10, 1997). "Conformation of Factor VIIa Stabilized by a Labile Disulfide Bond (Cys-310-Cys-329) in the Protease Domain is Essential for Interaction with Tissue Factor," *The Journal of Biological Chemistry* 272(41):25724-25730.
Holmgren, A. (Sep. 25, 1979). "Reduction of Disulfides by Thioredoxin. Exceptional Reactivity of Insulin and Suggested Functions of Thioredoxin in Mechanism of Hormone Action," *J. Bio. Chem.* 254(18):9113-9119.
Holmgren, A. (Oct. 10, 1979). "Thioredoxin Catalyzes the Reduction of Insulin Disulfides by Dithiothreitol and Dihydrolipoamide," *J. Bio. Chem.* 254(19):9627-9632.
Holmgren, A. (Mar. 15, 1995). "Thioredoxin Structure and Mechanism: Conformational Changes on Oxidation of the Active-Side Sulfhydryls to a Disulfide," *Structure* 3(3):239-243.
Howe, C. (1995). *Gene Cloning And Manipulation*, Cambridge University Press, p. 185.
Huang, H. et al. (2007, e-pub. Oct. 19, 2007). "Nitrogen Metabolism of Asparagine and Glutamate in Vero Cells Studied by $^1$H/$^{15}$N NMR Spectroscopy," *Applied Microbiol. Biotechnol.* 77:427-436.
Hutchinson, N. et al. (Oct. 20, 2006, e-pub. Jun. 9, 2006). "Shear Stress Analysis of Mammalian Cell Suspensions for Prediction of Industrial Centrifugation and Its Verification," *Biotechnology and Bioengineering* 95(3):483-491.
Hutterer, K.M. (Jul./Aug. 2013, e-pub. Apr. 18, 2013). "Monoclonal Antibody Disulfide Reduction During Manufacturing. Untangling Process Effects From Product Effects," *mAbs* 5(4):608-613.
Ikebuchi, M. (Sep. 1993). "Effect of Medium pH on Glutathione Redox Cycle in Cultured. Human Umbilical Vein Endothelial Cells," *Metabolism* 42(9):1121-1126.
Jayapal, KP. et al. (2007). "Recombinant Protein Therapeutics from CHO Cells—20 Years and Counting," CHO Consortium SBE Special Section pp. 40-47.
Jing, Y. et al. (2012, e-pub. Oct. 18, 2011). Identification of Ce !! Culture Conditions to Control Protein Aggregation of !gG Fusion Proteins Expressed in Chinese Hamster Ovary Cells, Process Biochem. 47:69-75.
Julien, C. et al. (Jan. 2007). "Getting the Most from Your Bioreactor," *Supplement*, 5 pages.
Johansson, C. et al. (Feb. 27, 2004). "Human Mitochondrial Glutaredoxin Reduces S-Glutathionylated Proteins with High Affinity Accepting Electrons from Either Glutathione or Thioredoxin Reductase," *The Journal of Biological Chemistry* 279(9):7537-7543.
Jorjani, P. et al. (Aug. 5, 1999). "Effects of Cell Density and Temperature on Oxygen Consumption Rate for Different Mammalian Cell Lines," *Biotechnology and Bioengineering* 64(3):349-356.
Junker, B. (2005). "Fermentation," in *Kirk-Othmer Encyclopedia of Chemical Technology* 11:1-55.
Junn, E. et al. (2000). "Vitamin $D_3$ Up-Regulated Protein 1 Mediates Oxidative Stress Via Suppressing the Thioredoxin Function," *Journal of Immunology* 164:6287-6295.
Junutula, J.R. et al. (Aug. 2008, e-pub. Jul. 20, 2008). "Site-Specific Conjugation of a Cytotoxic Drug to an Antibody Improves the Therapeutic Index," *Nature Biotechnology* 26(8):925-932.
Kaji, A. et al. (Nov. 1965). "Adenosine Triphosphate Activity of Yeast Hexokinase and Its Relation to the Mechanism of the Hexokinase Reaction," *The Journal of Biological Chemistry* 240(11):4454-4462.
Kao, Y-H. et al. (Nov. 1, 2010, e-pub. Jun. 29, 2010). "Mechanism of Antibody Reduction in Cell Culture Production Processes," *Biotechnology and Bioengineering* 107(4):622-632.
Kemp, G. et al. (2004). "Large-Scale Production of Therapeutics Antibodies: Considerations for Optimizing Product Capture and Purification," Chapter 3 in Antibodies vol. 1: Production and Purification, Subramanian, G. ed., Kluwer Academic/Plenum Publishers, pp. 75-100.
Kempken, R. et al. (Apr. 20, 1995). "Assessment of a Disc Stack Centrifuge for Use in Mammalian Cell Separation," *Biotechnology and Bioengineering* 46:132-138.
Kerblat, I. et al. (1999). "Importance of Thioredoxin in the Proteolysis of an Immunoglobulin G an Antigen by Lysosomal Cys-Proteases," *Immunology* 97(1):62-68.
Kirkpatrick, D.L. et al. (1998). "Mechanisms of Inhibition of the Thioredoxin Growth Factor System by Antitumor 2—Imidazolyl Disulfides," *Biochemical Pharmacology* 55:987-994.
Khan, H. A. et al. (Aug. 24, 2014). "Protein Disulfide Isomerase a Multifunctional Protein With Multiple Physiological Roles," *Frontiers in Chemistry* 2(70):1-9.
Koterba, K.L. et al. (2012, e-pub. Nov. 25, 2011). "Thioredoxin 1 is Responsible for Antibody Disulfide Reduction in CHO Cell Culture," *Journal of Biotechnology* 157:261-267.
Kunert, R. et al. (2016). "Advances in Recombinant Antibody Manufacturing," *Appl. Microbiol. Biotechnol.* 100:3451-3461. (D134).
Kurano, N. et al. (1990). "Growth Behavior Of Chinese Hamster Ovary Cells in a Compact Loop Bioreactor: 1. Effects of Physical and Chemical Environments," *J. Biotechnol.* 15:101-112.
Kurano, N. et al. (1990). "Growth Behavior Of Chinese Hamster Ovary Cells in a Compact Loop Bioreactor: 2. Effects of Physical and Chemical Environments," *J. Biotechnol.* 15:113-128.
Kwon, S-G. et al. (2006). "Increase of Xylitol Productivity by Cell-Recycle Fermentation of *Candida tropicalis* Using Submerged Membrane Bioreactor," *Journal of Bioscience and Bioengineering* 101(1):13-18.
Ladenstein, R. et al. (2006). "Protein Disulfides and Protein Disulfide Oxidoreductases in Hyperthermophiles," *FEBS Journal* 273:4170-4185.
Lambert, K.J. et al. (1987). "Industrial Scale Production of Monoclonal Antibodies in Airlift Fermenters," pp. 112-119.

(56) References Cited

OTHER PUBLICATIONS

Lambooy, P.K. (Apr. 2009). "Antibody Disulfide Bond Reduction Mitigation Strategies," 14th International Meeting, Waterside Conference, South San Francisco, Apr. 20-22, 2009, 11 pages.

Letter from Mewburn Ellis Intellectual Property, dated Nov. 25, 2015, to the European Patent Office, for Applicant Genentech, Inc. for European Patent Application No. 12178200.7, 4 pages.

Levy, R. et al. (2001). "Production of Correctly Folded Fab Antibody Fragment in the Cytoplasm of *Escherichia coli* trxB gor Mutants via the Coexpression of Molecular Chaperones," *Protein Expression and Purification* 23:338-347.

Li, L., et al. (1996). "Low Level Formation of Potent Catalytic IgG Fragments Mediated by Disulfide Bond Instability," *Molecular Immunology*, 33(7-8): 593-600.

Lillig, C.H. et al. (Jan. 2007). "Thioredoxin and Related Molecules—From Biology to Health and Disease," *Antioxidants& Redox Signaling* 9(1):25-47.

List of Approved Antibodies as of 2017, 4 pages, from European Opposition for European Patent No. 2 188 302, filed by Huttermann & Partner Patentanwaite mbB, 4 pages.

Liu, G. ed. (Oct. 1996). Aging and Cancer: Basic and Clinical, Sichuan University Press, 5 pages in total.

Liu, L. et al. (Jun. 30, 2006). "Study on Thioredoxin," *Journal of Northeast Agricultural University* 34(2):219-225. (English Translation).

Lundblad, J.L. et al. (1988). "The Effect of Processing Methods on Intravenous Immune Globulin Preparations," *Journal of Hospital Infection* 12(Supplemental D):3-15.

Lunn, C.A. et al. (Oct. 10, 1982). "Localization of Thioredoxin from *Escherichia coli* in an Osmotically Sensitive Compartment," *The Journal of Biological Chemistry* 257(19):11424-11430.

Lydersen, B.K. et al. (Nov. 1994). "Acid Precipitation of Mammalian Cell Fermentation Broth," *Ann. N.Y. Acad. Sci.* 745:222-231.

Ma, N. et al. (2006). "Aeration, Mixing and Hydrodynamics in Bioreactors," Chapter 7 in *Cell Culture Technology for Pharmaceutical and Cell-Based Therapies*, CRC Press, Boca Raton, FL., Ozturk, S.S. et al. eds., pp. 225-248.

Magnusson, C.G.M. et al. (1997). "Human IgG Substrate for the Thioredoxin System: Differential Cleavage Pattern of Interchain Disulfide Bridges in IgG Subclasses," *Molecular Immunology* 34(10):709-717.

Maita, N. et al. (Sep. 3, 2013). "Human α-L-Iduronidase Uses Its Own N-Glycan as a Substrate-Binding and Catalytic Module," *Proc. Nat. Acad. Sci.* USA 110(36):14628-14633.

Maloney, D.G. et al. (Sep. 15, 1997). "IDEC-C2B8 (Rituximab) Anti-CD20 Monoclonal Antibody Therapy in Patients With Relapsed Low-Grade Non-Hodgkin's Lymphoma," *Blood* 90(6):2188-2195.

Mcdonald, M.R. (1955). "Yeast Hexokinase. ATP + Hexose-→Hexose-6-Phosphate + ADP," *Method Enzymol.* 1:269-276.

McGraw-Hill Dictionary of Scientific and Technical Terms (2003) 6th Edition, p. 786, total 3 pages.

Menzella, H.G. et al. (2002). "High Recovery of Prochymosin From Inclusion Bodies Using Controlled Air Oxidation," *Protein Expression and Purification* 25:248-255.

Michaels, J.D. et al. (1996). "Sparing and Agitation-Induced Injury of Cultured Animal Cells: Do Cell-to-Bubble Interactions in the Bulk Liquid Injure Cells?," *Biotechnology and Bioengineering* 51:399-409.

Michalski—Hüttermann (Feb. 5, 2020)—Statement of English Language Use, 1 page.

Michalski—Hüttermann (Feb. 5, 2020)—Response to Patent Proprietor's Reply to Opposition, 33 pages.

Middelberg, A.P.J. (1995). "Process-Scale Disruption of Microorganisms," *Biotechnology Advances* 13(3):491-551.

Milhausen, M. et al. (1975). "Evidence for an Essential Lysine in Glucose-6-Phosphate Dehydrogenase from *Leuconostoc mesenteroid*," *Eur. J. Biochem.* 50:453-461.

Mowry, M.C. et al. (2004, e-pub. Jul. 27, 2004). "Production and Purification of a Chimeric Monoclonal Antibody Against Botulinum Neurotoxin Serotype A," *Protein Expression and Purification* 37:399-408.
Mowry, M.C. et al. (Oct. 2004). "Production and Purification of a Chimeric Monoclonal Antibody Against Botulinum Neurotoxin Serotype A," *Papers in Biotechnology-University of Nebraska—Lincoln* 33:1-23.
Mukherjee, A. et al. (2005, e-pub. Jan. 18, 2005). "Cytotoxic and Antiangiogenic Activity of AW464 (NSC 706704), a Novel Thioredoxin Inhibitor: an *in Vitro* Study," *British Journal of Cancer* 92:350-358.
Mullan, B. et al. (2011). "Disulphide Bond Reduction of a Therapeutic Monoclonal Antibody During Cell Culture Manufacturing Operations," BMC Proceedings 5(Supp. 8):p110, total 3 pages.
Mun, M. S. et al. (Aug. 2009). "BIOT 245-Air Sparging of Harvested Cell Culture Fluid (HCCF) to Prevent Antibody Disulfide Bond Reduction," Abstracts of Papers American Chemical Society 238:245.
Mun, M. et al. (Apr. 2015, e-pub. Dec. 23, 2014). "Air Sparging for Prevention of Antibody Disulfide Bond Reduction in Harvested CHO Cell Culture Fluid," Biotechnology & Bioengineering 112(4):734-742.
Nagle, S.C. et al. (1971). "An Improved Heat-stable Glutamine-free Chemically Defined Medium for Growth of Mammalian Cells," *J. Cell. Physiol*. 77:259-264.
Necina, R. et al. (Dec. 20, 1998). "Capture of Human Monoclonal Antibodies from Cell Culture Supernatant by Ion Exhange Media Exhibiting High Charge Density," *Biotechnology and Bioengineering* 60(6):689-698.
Neergaard, M.S. et al. (2014, e-pub. Nov. 26, 2013). "Stability of Monoclonal Antibodies at High-Concentration: Head-to-Head Comparison of the lgG1 and lgG4 Subclass," *Journal of Pharmaceutical Sciences* 103:115-127.
Newby, D. et al. (2005). "Short Communication. Dissolved Oxygen Concentration in Culture Medium: Assumptions and Pitfalls," *Placenta* 26:353-357.
The New Oxford American Dictionary. (2001). p. 623, total 3 pages.
Noda, T. et al. (2002). "Exogenous Cysteine and Cystine Promote Cell Proliferation in CaCo-2 Cells," Cell Prolif. 35:117-129.
Nordberg, J. et al. (2001). "Reactive Oxygen Species, Antioxidants, and the Mammalian Thioredoxin System," *Free Radical Biology & Medicine* 31(11):1287-1312.
Noiva, R. et al. (1999). "Protein Disulfide Isomerase: The Multifunctional Redox Chaperone of the Endoplasmic Reticulum," *Cell& Development* 10:481-493.
Non-Final Office Action Feb. 25, 2013, for U.S. Appl. No. 13/354,223, filed Jan. 19, 2012, 10 pages.
Oblong, J.E. et al. (1994). "Reversible Inhibition of Human hioredoxin Reductase Activity by Cytotoxic Alkyl 2-Imidazolyl Disulfide Analogues," *Cancer Chemother. Pharmacol*. 34:434-438.
Oh, J-E. et al. (2004). "Thioredoxin secreted upon ultraviolet A irradiation modulates activities of matrix metalloprotelnase-2 and tissue inhibitor of metalloproteinase-2 in human dermal fibroblasts," *Archives of Biochemistry and Biophysics* 423:218-226.
Ou, J. (2004). "Studies on Production Technology of Recombinant Human Stem Cell Factor," Northwest University Master's Degree Thesis, Issue 1, 16 pages in total.
Ozturk, S.S. et al. eds. (2005). *Cell Culture Technology for Pharmaceutical and Cell-Based Therapies*, CRC Press, Boca Raton, FL, pp. 1-788.
PubMed Search Results for Thioredoxin and Holmgren, Arne, (cited in European Opposition on Feb. 5, 2020), 3 pages.
Petersen, J.G.L. et al. (Sep. 10, 1974). "An *in Vitro* System for Studying the Kinetics of Interchain Disulfide Bond Formation in Immunoglobin G," *J. of Biological Chemistry* 249(17):5633-5641.
Petrides, D. (2000). "Bioprocess Design and Economics," Chapter 11 in *Bioprocess Design and Economics*, Oxford University Press Scotch Plains, NJ, pp. 1-60.
Pigiet, V.P. et al. (Oct. 1986). "Thioredoxin-Catalyzed Refolding of Disulfide-Containing Proteins," *Proc. Natl. Acad. Sci. USA 83*:7643-7647.

(56) References Cited

OTHER PUBLICATIONS

Pleasants, J.C. et al. (1989). "A Comparative Study of the Kinetics of Selenol/Diselenide and Thiol/Disulfide Exchange Reactions," *J. Am. Chem. Soc.* 111(17):6553-6558.

Powis, G et al., "Thioredoxin Redox Control of Cell Growth and Death and the Effects of Inhibitors," *Chemico-BiologicalInteractions* 111-112:23-34, (1998).

Powis, G. et al., "Properties and Biological Activities of Thioredoxins," *Annual Review of Pharmacology and Toxicology* 41:261-295, (2001).

Price, P.A. et al. (Feb. 25, 1969). "Effect of Divalent Cations on the Reduction and Re-formation of the Disulfide Bonds of Deoxyribonuclease," The Journal of Biological Chemistry 244(4):929-932.

Prinz, W.A. et al. (Jun. 20, 1997). "The Role of the Thioredoxin and Glutaredoxin Pathways in Reducing Protein Disulfide Bonds in the *Escherichia coli* Cytoplasm," *The Journal of Biological Chemistry* 272(25):15661-15667.

Proba, K. et al. (1995). "Functional Antibody Single-chain Fragments From the Cytoplasm of *Escherichia Coli*: Influence of Thioredoxin Reductase (trxb)," Gene 159(2):203-207.

Ramirez, D.M. et al. (2002). "Production, Recovery and Immunogenicity of the Protective Antigen From a Recombinant Strain of *Bacillus anthracis*," *J. of Industr. Microbiol. & Biotechn.* 28:232-238.
Ren, T. et al. (Jun. 1, 2021). "Antibody Disulfide Bond reduction and Recovery During Biopharmaceutical Process Development—A Review," Biotechnology and Bioengineering 118(8):2829-2844.
Reuveny, S. et al. (1986). "Factors Affecting Cell Growth and Monoclonal Antibody Production in Stirred Reactors," *Journal of Immunological Methods* 86:53-59.
Rieder, C.L. et al. (2002, e-pub. Mar. 20, 2002). "Cold-Shock and the Mammalian Cell Cycle," *Cell Cycle* 1:3:168-175.
Roman, B. et al. (Sep. 2005). "Development of a Robust Clarification Process for MAb Purification," *Case Study presented at the BioProcess International 2005 Conference& Exhibition*, Sep. 19-22, 2005, Boston, MA, four pages particularly p. 4.
Rose, S. et al. (2003). "Mammalian Cell Culture," Chapter 4 in *Handbook of Industrial Cell Culture: Mammalian, Microbial, and Plant Cells*, Vinci, V.A et al., eds., Humana Press, Totowa, N.J., pp. 69-103.
Roush, D.J. et al. (2008). "Advances in Primary Recovery: Centrifugation and Membrane Technology," *Biotechnol. Prog.* 24(3):488-495.
Rubartelli, A. et al. (Dec. 5, 1992). "Secretion of Thioredoxin by Normal and Neoplastic Cells Through a Leaderless Secretory Pathway," Journal of Biological Chemistry 267(34):24161-24164.
SAFC BIosciences™. (2006). "Product Information Ex-Cell™ CD CHO Serum-Free Medium for CHO Cells, Chemically Defined," Catalogue No. 14360C, 4 pages.
Salas-Solano, O. et al. "Optimization and Validation of a Quantitative Capillary Electrophoresis Sodium Dodecyl Sulfate Method for Quality Control and Stability Monitoring of Monoclonal Antibodies," *Analytical Chemistry* 78(18):6583.6594, (2006).
Sambrook, J. et al. (1989). *Molecular Cloning A Laboratory Manual*, Second Edition. Cold Spring Harbor Laboratory Press, 18.30 and 18.31, 3 pages.
Sandberg, H. et al. (Dec. 5, 2006, e-pub. Aug. 8, 2008). "Mapping and Partial Characterization of Proteases Expressed by a CHO Production Ceil Line," *Biotechnology and Bioengineering* 95(5):961-971.
Sanfeliu, A. et al. (Jul. 5, 1999). "Effect of Glutamine Limitation on the Death of Attached Chinese Hamster Ovary Cells," *Biotechnology& Bioengineering* 64(1):46-53.
Schuler, M.L. et al. (2002). *Bioprocess Engineering: Basic Concepts*, Second Edition, Prentice Hall PTR, Upper Saddle River, N.J., pp. 1-576). 2002.
Schwartz, A.G. et al. (2004). "Dehydroepiandrosterone, Glucose-6-Phosphate Dehydrogenase, and Longevity," *Ageing Research Reviews* 3:171-187.
Selles, B. et al. (Mar. 31, 2017). "Atypical Protein Disulfide Isomerases (PDI): Comparison of the Molecular and Catalytic Properties of Poplar PDI-A and PDI-M with PDSI-L1A," *Plos One* 12(3):30174753, 1-21.
Sevier, C.S. et al. (Nov. 2002). "Formation and Transfer of Disulphide Bonds in Living Cells," *Nature Reviews* 3:836-847.
Shaunak, S. et al. (Jun. 2006, e-pub. Apr. 23, 2006). "Site-Specific PEGylation of Native Disulfide Bonds in Therapeutic proteins," *Nature Chemical Biology* 2(6):312-313, (3 pages).
Shukla, A. et al. (Jul. 7, 2006). "Process Scale Bioseparations for the Biopharmaceutical Industry," CRC press, p. 127, 3 pages total.
Siegel, M.H. et al. (Sep./Oct. 1992). "Applications of Airlift Gas-Liquid-Solid Reactors in Biotechnolgy," Chemical Engineering Science 47(13/14):3215-3229.
SIGMA-ALDRICH. (Cited In European Opposition Aug. 27, 2018). "Product Specification Ex-Cell ACF CHO Medium-Animal-Component Free, with HEPES, Without L-Glutamine, Liquid, Sterile-Filtered, Suitable for Cell Culture," Product No. C5467, 1 page.
SIGMA-ALDRICH. (2017). "Product Information Hexokinase From Saccharomyces Cerivisiae," Catalog No. H4502, 2 pages.
SIGMA. (Dec. 2002). "Product Information, 1,2-bis(2-Aminophenoxy)ethane-N,N,N',N'—Tetraacetic Acid (BAPTA)," Product No. A4926, 1 page.
SIGMA. (Jan. 2003). "Product Information L-Cystine," Product No. C 8755, 1 page.
Singh, R. et al. (1991). "A Reagent for Reduction of Disulfide Bonds in Proteins That Reduces Disulfide Bonds Faster Than Does Dithiothreitol," *J. Org. Chem.* 56:2332-2337.
Singh, R. et al. (1993). "Thiol-Disulfide Interchange," Chapter 13 in Supplement S: *The Chemistry of Sulphur Containing Functional Groups*, Patai, S. et al. eds., John Wiley & Sons, Inc., pp. 633-658.
Singh, S. et al. (Dec. 2003). "Biochemical and Immunological Characterization of Bacterially Expressed and Refolded Plasmodium Falciparum 42-Kiloldalton C-Terminal Merozoite Surface Protein 1," *Infection and Immunity* 71(12):6766-6774.
Smith, A.D. et al. (2001). "Effect of Gold (I) Compounds on the Virulence of Amyocarditic Strain of Coxsackievirus B3," *Biological Trace Element Research*, vol. 84, 14 pages in total.
Smith, M., et al. (1996). "Specific Cleavage of Immunoglobulin G by Copper Ions," *International Journal of Peptide and Protein Research* 48(1): 48-55.
Smith, A.D. et al. (1999). "Aurothioglucose Inhibits Murine Thioredoxin Reductase Activity In Vivo," *J. Nutr.* 129:194-198.
Soderbert, S. et al. (Aug. 1998). "Monoclonal Antibodies to Human Thioredoxin Reductase," *Biochem. Bioph. Res. Comm.* 249(1):86-89. (Abstract only).
Sonderegger, C. (Apr. 2009). "SANDOZ. Antibody Reduction and More Recent Challenges to the Scale-up of CHO Manufacturing Processes," Wllbio 14$^{th}$ Waterside Conference in San Francisco, Apr. 20-22, 2009, 14 pages.
Specification of PCT/US2008/069395, internationally filed on Jul. 8, 2008, published as WO-2009/009523 on Jan. 15, 2009, 87 pages.
Stanbury, P.F. et al. (1995). *Principles of Fermentation Technology*, Chapter 7 through 9, Second Edition, pp. 167-312.
Starks, C.M. et al. (Jan. 2007). "Atomic-Resolution Crystal Structure of Thioredoxin From the Acidophilic Bacterium *Acetobacter Aceti*," *Protein Science* 16(1):92-98.
Staudacher, A.H. et al. (2014). "The La Antigen is Over-Expressed in Lung Cancer and is a Selective Dead Cancer Cell Target for Radioimmunotherapy Using the La-Specific Antibody Apomab®," *EJNMMI Research* 4(2):1-13.
Stephanopoulos, G. ed. (1993). "Bioprocessing," in vol. 3: *Bioprocessing, in Biotechnology*, Second Edition, VCH Publishers, Inc., New York, 20 pages.
Stryer, L. et al. (2003). "20.3 The Pentose Phosphate Pathway Produces NADPH and $C_5$ Carbohydrates," *Biochemie*, Guglielmi, J. et al. eds., Spektrum Academic Publishing Heidelberg, Berlin, pp. 616-617, with English translation 6 pages.
Tam, J.P. et al. (1991). "Disulfide Bond Formation in Peptides by Dimethyl Sulfoxide, Scope and Applications," J. Am. Chem. Soc. 113(17):6657-6662.

(56) References Cited

OTHER PUBLICATIONS

Tanudji, M. et al. (Jan. 15, 2003). "The Nonclassic Secretion of Thioredoxin is not Sensitive to Redox State," Am. J. Physiol. Cell Physiol. 284:C1272-C1279.
Tebbe, H. et al. (1996). "Lysis-Free Separation of Hybridoma Cells by Continuous Disc Stack Centrifugation," *Cytotechnology* 22:119-127.
Technical data sheet for a hexokinase enzyme product, dated 2017, from European Opposition for European Patent No. 2 188 302, 2 pages.
Teilum, K. et al., "Disulfide Bond Formation and Folding of Plant Peroxidases Expressed as Inclusion Body Protein in *Escherichia Coli* Thioredoxin Reductase Negative Strains," *Protein Expression and Purification Academic Press* 15(1):77-82, (1999).
Thomsen, J. et al. (Apr. 1972). "The Amino Acid Sequence of Human Glucagon," *FEBS Letters* 21(3):315-319.
Tian, W.N. et al. (Apr. 24, 1998). "Importance of Glucose-6-phosphate Dehydrogenase Activity for Cell Growth," *The Journal of Biological Chemistry* 273(17):10609-10617.
Trexler-Schmidt et al. (Jun. 15, 2010). "Identification and Prevention of Antibody Disulfide Bond Reduction During Cell Culture Manufacturing," *Biotechnology and Bioengineering* 160(3):452-461.
Trocha, M. et al. (1995). "Bubble Bed Aeration for Animal Cell Cultures," *Animal Cell Technology: Developments Towards the 21st Century*, Beuvery, E.C et al. eds., Kluwer Academic Publishers, pp. 893-898.
Tsuji, T. et al. (1987). "Characterization of Disulfide Bonds in Recombinant Proteins: Reduced Human Interleukin 2 in Inclusion Bodies and Its Oxidative Refolding," *Biochemistry* 26:3129-3134.
UPTIMA. (Cited in European Opposition Jul. 30, 2018). "Product Leaflet From Interchim Regarding EDTA," Life Sciences Interchim®, 3 pages.
Urig, S. et al. (2006). "On the Potential of Thioredoxin Reductase Inhibitors for Cancer Therapy," *Seminars in Cancer Biology* 16(6): 452-465.
Assignment for U.S. Appl. No. 12/217,745, recorded on Oct. 31, 2008, 12 pages.
Van Der Pol, L.A. (Dec. 4, 1998). *Sparging-Shear Sensitivity of Animal Cells*, 96 pages.
Varley, J. et al. (1999). "Reactor Design for Large Scale Suspension Animal Cell Culture," *Cytotechnology* 29:177-205.
Velez, D. et al. (1986). "Kinetics of Monoclonal Antibody Production in Low Serum Growth Medium," *Journal of Immunological Methods* 86: 45-52.
Vermeer, A.W.P. (Jan. 2000). "The Thermal Stability of Immunogobulin: Unfolding and Aggregation of Multi-Domain Protein," *Biophysical Journal* 78:394-404.
Voet, D. et al. (1995). *Biochemistry*, Second Edition, John Wiley & Sons, Inc., New York, pp. 447, 618, 786, 811.
Vogel, H.C. et al. (1997). *Fermentation and Biochemical Engineering Handbook: Principles, Process Design, and Equipment*, Second Edition, Noyes Publication, Westwood, N.J., pp. 1-829.
Wall, J.S. (1971). "Disulfide Bonds: Determination, Location, and Influence on Molecular Properties of Proteins," *J. Agr. Food Chem.* 19(4):619-625.
Wang, T. et al. (Aug. 2013, e-pub. Jul. 3, 2013). "Effect of Ionic Strength and pH on the Physical and Chemical Stability of a Monoclonal Antibody Antigen-Binding Fragment," *Journal of Pharmaceutical Sciences* 102(8):2520-2537.
Wang, T. et al. (2015, e-pub. Oct. 31, 2014). "Investigation of Antibody Disulfide Reduction and Re-Oxidation and Impact to Biological Activities," *J. of Pharmaceutical and Biomedical Analysis* 102:519-528.
Watabe, S. et al. (1999). "Mitochondrial Thioredoxin Reductase in Bovine Adrenal Cortex. Its Purification, Properties, Nucleotide/ Amino Acids Sequences and Identification of Selenocysteine," *Eur. J. Biochem.* 264:74-84.

Whitesides, G.M. et al. (1977). "Rates of Thiol-Disulfide Interchange Reaction Between Mon-and Dithiols and Ellman's Reagents," *J. Org. Chem.* 42(2):332-338.
Whittemore, B.A. (Feb. 16, 2005). *Recombinant Collagen Production Optimization in Escherichia coli*, 159 pages.
Wipf, P. et al. (Dec. 31, 2001). "New Inhibitors of the Thioredoxin-Thioredoxin Reductase System Based on a Naphthoquione Spiroketal Natural Product Lead," *Bioorganic& Medicinal Chemistry Letters* 11:2637-2641.
Wong, D.C.F. et al. (2006, e-pub. Aug. 7, 2006). "Targeting Early Apoptotic Genes in Batch and Fed-Batch CHO Cell Cultures," Biotechnology and Bioengineering 95(3):350-361.
Wu, S. (Jun. 2005). Biochemistry, University of Science and Technology of China Press, 14 pages in total.
Wurm, F.M. (2004). "Production of Recombinant Protein Therapeutics in Cultivated Mammalian Cells," *Nature Biotechnology* 1393-1398.
Xia, L. et al. (Jan. 24, 2003, e-pub. Nov. 14, 2002). "The Mammalian Cytosolic Selenoenzyme Thioredoxin Reductase Reduces Ubiquinone," *The Journal of Biological Chemistry* 278(4):2141-2146.
Xie, L. et al. (2006). "Fed-Batch Cultivation of Mammalian Cells for the Production of Recombinant Proteins," Chapter 10 in *Cell Culture Technology for Pharmaceutical and Cell-Based Therapies*, CRC Press, Boca Raton, FL, pp. 349-386.
Xiong, Z. (2000). Environmental Biology, Wuhan University Press, p. 177, 5 pages in total.
Xiong, S. (2002). "Expression, Purification and Characterization of a Human Single-chain Fv Antibody Against HBsAg in *E. coli* and *P. pastoris*," by South China University of Technology, 13 pages (with English translation).
Yigzaw, Y. et al. (2006, e-pub. Jan. 6, 2006). "Exploitation of the Adsorptive Properties of Depth Filters for Host Cell Protein Removal During Monoclonal Antibody Purification," *Biotechnol. Prog.* 22:288-296.
Yoon, S.K. et al. (2007). "Effect Of Culture Temperature on Follicle-Stimulating Hormone Production by Chinese Hamster Ovary Cells in a Perfusion Bioreactor," *Appl. Microbiol. Biotechnol.* 76:83-89.
Zeng, A-P. et al. (2006). "Cell Culture Kinetics and Modeling," Chapter 9 in *Cell Culture Technology for Pharmaceutical and Cell-Based Therapies*, CRC Press, Boca Raton, FL., Ozturk, S.S et al. eds., pp. 299-348.
Zhang, W. et al. (2002). "Free Sulfhydryl in Recombinant Monoclonal Antibodies," *Biotechnology Progress* 18(3):509-513.
Zhong, L. et al. (Jun. 16, 2000, e-pub. Apr. 12, 2000). "Essential Role of Selenium in the Catalytic Activities of Mammalian Thioredoxin Reductase Revealed by Characterization of recombinant Enzymes With Selenocysteine Mutations," *The Journal of Biological Chemistry* 275(24):18121-18128.
Zhuang, P. et al. (Jun. 14, 1996). "Characterization of the Denaturation and Renaturation of Human Plasma Vitronectin," *The Journal of Biological Chemistry* 271(24):14333-14343.
Zubay, G. (2000). "Methods for Characterization and Purification of Proteins," *Biochemistry*, $4^{th}$ edition, Brandt, U. et al. eds., McGraw-Hill, pp. 140-155.
Zwart, J. et al. (Jan. 1981). "The Mechanism of the Copper Ion Catalyzed Autoxidation of Cysteine in Alkaline Medium," *Journal of Molecular Catalysis* 12:85-101.
U.S. Appl. No. 60/855,734, filed Nov. 1, 2006, for Romero et al., 111 pages.
U.S. Appl. No. 06/679,121, filed Dec. 6, 1984, for Koths et al. (A U.S. Patent Application is not submitted herewith pursuant to the waiver of 37 C.F.R. § 1.98(a)(2)(iii) issued by the Office on Sep. 21, 2004.).
U.S. Appl. No. 09/679,705, filed Oct. 5, 2000, for Beckwith et al. (A U.S. Patent Application is not submitted herewith pursuant to the waiver of 37 C.F.R. § 1.98(a)(2)(iii) issued by the Office on Sep. 21, 2004.).
U.S. Appl. No. 10/968,757, filed Oct. 19, 2004, for Kordyum et al. (A U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

Chinese Reexamination Decision No. 117911, for Chinese Patent Application No. 200880105932.5, dated Jan. 6, 2017, 35 pages.
Chinese Office Action Response, dated Aug. 8, 2013, for Chinese Patent Application No. 200880105932.5, made by the Patentee to the second office action, 10 pages in total.
Chinese Office Action Response, dated Apr. 25, 2014, for Chinese Patent Application No. 200880105932.5, of the Patentee to the Third Office Action, 10 pages.
Decision by Commercial Court of Vienna 30 Cg 43/19g, dated Oct. 31, 2019, with English Translation, 44 pages.
European Search Report and Search Opinion, mailed on Apr. 12, 2018, for European Patent Application No. 17196350.7, filed on Oct. 13, 2017, 17 pages.
European Extended Search Report and Search Opinion, mailed on Aug. 21, 2023, for European Patent Application No. 23153140.1, filed on Jan. 1, 2023, 11 pages.
Notice of European Opposition for European Patent No. 3 327 026, dated Feb. 18, 2020, Proprietor Genentech, Inc., Opponent Hexal AG, 35 pages.
Communication of a Notice of European Opposition for European Patent No. 3 327 026, dated Feb. 21, 2020, Proprietor Genentech, Inc., Opponent Hexal AG, 1 page.
European Patent Application No. 19181777.4, claims dated Jul. 22, 2021, 2 pages.
Notice of Opposition for European Patent No. 2 188 302-B1, dated Jul. 30, 2018, Proprietor Genentech, Inc., Opponent Grünecker Patent-und Rechtsanwälte PartG mbB, 37 pages.
Notice of Opposition for European Patent No. 2 188 302-B1, dated Jul. 30, 2018, Proprietor Genentech, Inc., Opponent Michalski Hüttermann & Partner, 60 pages.
Notice of Opposition for European Patent No. 2 188 302-B1, dated Aug. 1, 2018, Proprietor Genentech, Inc., Opponent Bayer Intellectual Property GmbH, 31 pages.
Notice of Opposition for European Patent No. 2 188 302-B1, dated Aug. 1, 2018, Proprietor Genentech, Inc., Opponent Cornella Oetke, 25 pages.
Notice of Opposition for European Patent No. 2 188 302-B1, dated Aug. 16, 2018, Proprietor Genentech, Inc., Opponent Mathys & Squire LLP, 23 pages.
Notice of Opposition for European Patent No. 2 188 302-B1, dated Aug. 1, 2018, Proprietor Genentech, Inc., Opponent Maiwald Patent-und Rechtsanwaltsgesellschaft mbH, 30 pages.
Notice of Opposition for European Patent No. 2 188 302-B1, dated Aug. 1, 2018, Proprietor Genentech, Inc., Opponent df-mp Dörries Frank-Molnia & Pohlman, Patentanwälte, Par G mbB, 34 pages.
Notice of Opposition for European Patent No. 2 188 302-B1, dated Aug. 1, 2018, Proprietor Genentech, Inc., Opponent Hoffmann Eitle, Patent-und Rechtsanwälte PartmbB, 24 pages.
Notice of Opposition for European Patent No. 2 188 302-B1, dated Aug. 1, 2018, Proprietor Genentech, Inc., Opponent Merck Sharp & Dohme Corp., 39 pages.
Notice of Opposition for European Patent No. 2 188 302-B1, dated Aug. 1, 2018, Proprietor Genentech, Inc., Opponent Dr. H. Ulrich Dörries, df-mp Dörries Frank-Molina & Pohlman, Patentanwälte Rechtsanwälte, PartG mbB, 18 pages.
Notice of Opposition for European Patent Application No. 08781481.0, dated Jan. 27, 2020, 21 pages.
Decision by Commercial Court of Vienna 30 Cg 43/19g. Oct. 22, 2019, with English Translation, 44 pages.
Notice of Opposition for European Patent No. 2 586 788, mailed on Aug. 24, 2018, Proprietor Genentech, Inc., Opponent Michalski Hüttermann & Partner Patenanwäite mbB, 43 pages.
Notice of Opposition for European Patent No. 2 586 788, mailed on Aug. 27, 2018, Proprietor Genentech, Inc., Opponent Grünecker Patent-und Reschtsanwäite Part G mbB, 41 pages.
Notice of Opposition for European Patent No. 2 586 788, mailed on Aug. 27, 2018, Proprietor Genentech, Inc., Opponent Glaxo Group Limited, 25 pages.
Notice of Opposition for European Patent No. 2 586 788, mailed on Aug. 29, 2018, Proprietor Genentech, Inc., Opponent UCB Biopharma SPRL, 23 pages.
Notice of Opposition for European Patent No. 2 586 788, mailed on Aug. 29, 2018, Proprietor Genentech, Inc., Opponent, Maiwald Patentanwaits-und Rechtsanwaitsgesellschaft mbH, 32 pages.
Notice of Opposition for European Patent No. 2 586 788, mailed on Aug. 29, 2018, Proprietor Genentech, Inc., Opponent, Bayer Intellectual Property GmbH, 27 pages.
Notice of Opposition for European Patent No. 2 586 788, mailed on Aug. 29, 2018, Proprietor Genentech, Inc., Opponent, df-mp Dörries Frank-Molnia & Pohlman, 35 pages.
Notice of Opposition for European Patent No. 2 586 788, mailed on Aug. 29, 2018, Proprietor Genentech, Inc., Opponent, Ms. Cornelia OETKE, 31 pages.
Notice of Opposition for European Patent No. 2 586 788, mailed on Aug. 29, 2018, Proprietor Genentech, Inc., Opponent: Merck Sharp & Dohme Corp., 23 pages.
Response to European Patent Office, Jun. 14, 2019, for European Patent No. 2188302, Genentech, Inc., Merck Sharp & Dohme Corporation O9, 15 pages.
Response to the European Patent Office, Jun. 27, 2019, for European Patent No. 2 188 302, Proprietor: Genentech, Inc., Opponent Cornelia Oetke (O4), 24 pages.
European Communication, Summons to Attend Oral Hearing, Jul. 15, 2019, for European Patent No. 2 188 302, 21 pages.
Response to European Patent Office, Apr. 23, 2019, for European Patent No. 2586788, Proprietor: Genentech, Inc., Proprietor Michalski Hüttermann & Partner Patentanwalte MBB et al., 149 pages.
European Communication, Summons to Attend Oral Hearings, dated Jul. 12, 2019, for European Patent No. 2586788, 23 pages.
Response to Non-Final Office Action May 25, 2013, for U.S. Appl. No. 13/354,223, filed Jan. 19, 2012, 11 pages.
Response to Non-Final Office Action Under 37 C.F.R §1.111, For U.S. Appl. No. 14/734,838, mailed on Jun. 8, 2017, 11 pages.
Response to European Office Action mailed on Jul. 20, 2016, for European Patent Application No. EP13713295.7, filed Oct. 17, 2014, 19 pages.
Response to European Opposition for European Patent No. 2188302, mailed on Apr. 1, 2019, Proprietor: Genentech Inc., Opposed by Grunecker Patent-Und Rechtsanwalte Partg MBH et al., 103 pages.
In the United States District Court for the District of Delaware, *Genentech, Inc.* and *City of Hope*, Plaintiffs, v. *Amgen Inc.*, Defendant, C.A. No. 17-1407-CFC (Consol.), Declaration of Dr. Hansjörg Hauser in Support of Plaintiffs' Opening Claim Construction Brief, Dec. 21, 2018, 35 pages.
In the United States District Court for the District of Delaware, *Genentech, Inc. and City of Hope*, Plaintiffs, v. *Amgen Inc.*, Defendant, C.A. No. 17-1407-CFC (Consol.), Genentech, Inc's Opening Claim Construction Brief, (Redacted), Jan. 2, 2019, 27 pages.
In the United States District Court for the District of Delaware, *Genentech, Inc. and City of Hope*, Plaintiffs and Counterclaim Defendants, v. *Amgen Inc.*, Defendant and Counterclaim Plaintiff, *Genentech, Inc. and City of Hope*, Plaintiffs and Counterclaim Defendants, v. *Samsung Bioepsis col. Ltd.*, Defendant and Counterclaim Plaintiff, Civ. No. 18-294-CFC, Civ. No. 18-1363-CFC, Jun. 14, 2019, 33 pages.
In the United States District Court for the District of Delaware, *Genentech, Inc. and the City of Hope* Plaintiffs, v. *Amgen Inc.*, Defendant, Civ. No. 17-1407-CFC, Consol., Memorandum Opinion, signed by United States District Judge Connolly, Jun. 17, 2019, 30 pages.
In the United States District Court for the District of Delaware, *Genentech, Inc. and City of Hope*, Plaintiffs, v. *Amgen Inc.*, Defendant, C.A. No. 17-1407-CFC (Consol.) Confidential Jury Trial Demanded, Jul. 23, 2019, 27 pages.
In the United States District Court for the District Court of Delaware, Declaration of Jeffrey Chalmers, Ph.D., in Support of Defendants' Construction Brief, dated Apr. 9, 2019, filed on Apr. 10, 2019, *Genentech, Inc. and City of Hope*, Plaintiffs and Counterclaim Defendants, v. *Amgen Inc.*, Defendant and Counterclaim Plaintiff, C.A. No. 18-924-CFC, *Genentech, Inc. and City of Hope*, Plaintiffs

(56) References Cited

OTHER PUBLICATIONS and Counterclaim Defendants, v. *Samsung Bioepis Co., Ltd.* Defendant and Counterclaim Plaintiff, C.A. No. 18-1363-CFC, 26 pages.
In the United States District Court for the District Court of Delaware, filed on Apr. 10, 2019, Revised Joint Claim Construction Brief, *Genentech, Inc. and City of Hope*, Plaintiffs and Counterclaim Defendants, v. *Amgen, Inc.*, Defendant and Counterclaim Plaintiff., C.A. No. 18-924-CFC, *Genentech, Inc. and City of Hope*, Plaintiffs and Counterclaim Defendants, v. 6*Samsung Bioepis Co., Ltd.* Defendant and Counterclaim Plaintiff., C.A. No. 18-1363-CFC, 148 pages.
In the United States District Court for the District Court of Delaware, Declaration of Dr. Hansjörg Hauser, in Support of Plaintiffs' Construction Brief, dated Jan. 11, 2019, filed on Mar. 22, 2019, *Genentech, Inc. and City of Hope*, Plaintiffs and Counterclaim Defendants, v. *Amgen, Inc.*, Defendant and Counterclaim Plaintiff., C.A. No. 18-924-CFC, *Genentech, Inc. and City of Hope*, Plaintiffs and Counterclaim Defendants, v. *Samsung Bioepis Co., Ltd.* Defendant and Counterclaim Plaintiff, C.A. No. 18-1363-CFC, 46 pages.
In the United States District Court Northern District of California, filed on Jan. 11, 2018, Complaint for Declaratory Judgement of Patent Non-Infringement and/or Invalidity, Redacted version of Document Sought to be Sealed, [Confidential Portions Redacted], *Celltrion, Inc., Celltrion Healthcare., Ltd. Teva Pharmaceuticals USA, Inc., and Teva Pharmaceuticals International GmbH*, Plaintiffs, v. *Genentech, Inc., Biogen Inc., Hoffmann-La Roche Inc., and City of Hope*, Defendants, 77 pages.
In the United States District Court for the District of New Jersey, filed on Jun. 14, 2018, Defendants' Answer, Affirmative Defenses, And Counterclaims, Redacted Version, *Genentech, Inc., Biogen, Inc., Hoffmann-La Roche Inc., and City Of Hope*, Plaintiffs, v. *Celltrion, Inc., Celltrion Healthcare Co., Ltd., Teva Pharmaceuticals USA, Inc., And Teva Pharmaceuticals International GmbH*, Defendants., Civil Action No. 18-0574 (RMB/KMW), 177 pages.
In the United States District Court for the District of Delaware, filed on Jan. 10, 2018, Defendant Pfizer Inc.'s Answer Affirmative Defenses, and Counterclaims, C.A. No. 17-1672-GMS, *Genentech, Inc. and City of Hope*, Plaintiffs, v. *Pfizer Inc.* Defendant, 176 pages.
In the United States District Court for the District of Delaware, filed on Aug. 24, 2018, Defendants' Answer, Affirmative Defenses and Counterclaims to Plaintiffs' Complaint, C.A. No. 18-1025-GMS, Redacted Public Version, *Genentech, Inc., City of Hope, and Hoffmann-La Roche Inc.*, Plaintiffs, v. *Celltrion, Inc., Celltrion Healthcare Co., Ltd., Teva Pharmaceuticals USA, Inc., and Teva Pharmaceuticals International GmbH*, Defendants, 136 pages.
In The United States District Court For The District of Delaware, Filed on Dec. 11, 2018, Joint Claim Construction Chart, Document 60, *Genentech, Inc., City Of Hope, And Hoffmann La Roche Inc.*, Plaintiffs And Counter Defendants, V. *Celltrion, Inc., Celltrion, Healthcare Co., Ltd., Teva Pharmaceuticals USA, Inc., And Teva Pharmaceuticals International Gmbh*, Defendants And Counterclaim Plaintiffs., C.A. No. 18-95-CFC (Consolidated), *Genentech, Inc. And City Of Hope*, Plaintiffs And Counterclaim Defendants, V. *Amgen Inc.*, Defendant And Counterclaim Plaintiff., C.A. No. 18-924-CFC, *Genentech, Inc. And City Of Hope*, Plaintiffs And Counterclaim Defendants, V. *Samsung Bioepis Co., Ltd*, Defendant And Counterclaim Plaintiff., C.A. No. 18-1363-CFC, 46 Pages.
In The United States District Court For The District Of Delaware, Filed On Dec. 11, 2018, Joint Claim Construction Chart, Document 96, *Genentech, Inc., City Of Hope, And Hoffmann La Roche Inc.*, Plaintiffs And Counter Defendants, V. *Celltrion, Inc., Celltrion, Healthcare Co., Ltd., Teva Pharmaceuticals USA, Inc., And Teva Pharmaceuticals International Gmbh*, Defendants And Counterclaim Plaintiffs., C.A. No. 18-95-CFC (Consolidated), *Genentech, Inc.* And *City Of Hope*, Plaintiffs And Counterclaim Defendants, V. *Amgen Inc.*, Defendant And Counterclaim Plaintiff., C.A. No. 18-924-CFC, *Genentech, Inc. And City Of Hope*, Plaintiffs And Counterclaim Defendants, V. *Samsung Bioepis Co., Ltd*, Defendant And Counterclaim Plaintiff., C.A. No. 18-1363-CFC, 46 Pages.

In The United States District Court For The District Of Delaware, Filed On Dec. 11, 2018, Joint Claim Construction Chart, Document 48, *Genentech, Inc., City Of Hope, And Hoffmann La Roche Inc.*, Plaintiffs And Counter Defendants, V. *Celltrion, Inc., Celltrion, Healthcare Co., Ltd., Teva Pharmaceuticals USA, Inc., And Teva Pharmaceuticals International Gmbh*, Defendants And Counterclaim Plaintiffs., C.A. No. 18-95-CFC (Consolidated), *Genentech, Inc. And City Of Hope*, Plaintiffs And Counterclaim Defendants, V. *Amgen Inc.*, Defendant And Counterclaim Plaintiff., C.A. No. 18-924-CFC, *Genentech, Inc. And City Of Hope*, Plaintiffs And Counterclaim Defendants, V. *Samsung Bioepis Co., Ltd*, Defendant And Counterclaim Plaintiff., C.A. No. 18-1363-CFC, 46 Pages.
In the United States District Court for the District of Delaware, filed on Jan. 31, 2019, Jury Trial Demanded, Document 66, Defendant Samsung Bioepis Co., LTD.'S Answer, Defenses, and Counterclaims to Plaintiffs' First Amended Complaint, *Genentech, Inc., and City of Hope*, Plaintiffs, v. *Samsung Bioepis Co., Ltd*., Defendants, C.A. No. 18-1363-CFC, 94 pages.
In the United States District Court for the District of Delaware, Filed on Nov. 21, 2018, Joint Claim Construction, *Genentech, Inc. and City of Hope*, Plaintiffs, v. *Amgen Inc.*, Defendant., C.A. No. 17-1407-GMS Consoliated, 31 pages.
*Genentech, Inc. and City of Hope*, Plaintiffs, v. *Amgen, Inc.*, Defendant, *Genentech, Inc.*, Plaintiff and Counterclaim Defendant, v. *Amgen, Inc.*, Defendant and Counterclaim Plaintiff, Genentech's Letter-Brief Concerning Construction of "Following Fermentation", C.A. No. 17-1407-CFC (Consolidated), Public Version Filed Mar. 3, 2020, C.A. No. 18-924-CFC, 44 pages.
*Genentech, Inc. and City of Hope*, Plaintiffs, v. *Amgen, Inc.*, Defendant, *Genentech, Inc.*, Plaintiff, v. *Amgen Inc.*, Defendant, Amgen Inc.'s Letter Response Regarding Court's Construction of "Following Fermentation", C.A. No. 17-1407-CFC-SRF (Consolidated), C.A. No. 18-924-CFC-SRF, Redacted, Public Version, dated Feb. 26, 2020, 13 pages.
Oral Claim Construction, *Genentech, Inc.* et al. v. *Amgen Inc.*, Case No. 1:17-cv-01407-CFC-SRF, Ordered by Judge Colm F. Connolly on Feb. 18, 2020, 1 page.
*Genentech, Inc. and City of Hope*, Plaintiffs, v. *Amgen, Inc.*, Defendant, *Genentech, Inc. and City of Hope*, Plaintiff, v. *Amgen Inc.*, Defendant, "Memorandum Opinion", C.A. No. 17-1407-CFC (Consolidated), C.A. No. 18-924-CFC, dated Mar. 9, 2020, 20 pages.
Casagrande, S. et al. (Jul. 23, 2002). "Glutathionylation of Human Thioredoxin: a Possible Crosstalk Between the Glutathione and Thioredoxin Systems," PNAS 99(15): 9745-9749, Cited in Submission Under Rule 116 EPC for Opposition of European Patent 2188302B1 from Opponent 09 (Merck & Sharp EP) dated Apr. 10, 2020. Forwarded in a Communication from the European Patent Office to Mewburn Ellis, Counsel for Genentech, on Apr. 17, 2020.
Hultberg, B. et al. (1997). "Copper Ions differ From Other Thiol Reactive Metal Ions in Their Effect on the Concentration and Redox Status of Thiols in Hela Cell Cultures," Toxicology 17:89-97. Cited in Submission Under Rule 116 EPC for European Patent 2188302B1 from Opponent 09 (Merck & Sharp EP) dated Apr. 10, 2020. Forwarded in a Communication from the European Patent Office to Mewburn Ellis, Counsel for Genentech, on Apr. 17, 2020.
Janson, J-C. et al. (1998). "Introduction To Protein Purification," Chapter 8 in Protein Purification: Principles, High Resolution Methods, and Applications, pp. 8-11. Cited in Letter from Opponent 06 (Maiwald) for Opposition of European Patent 2188302B1 dated Apr. 10, 2020. Forwarded in a Communication from the European Patent Office to Mewburn Ellis, Counsel for Genentech, on Apr. 17, 2020.
Smith, R.C. et al. (1994). "Oxidation Of Thiols by Copper(II)," Phosphorus, Sulfur, and Silicon and the Related Elements 90: 14 7-154. Cited in Letter from Opponent 04 (Cornelia Oetke) Observation pursuant to Rule 116 EPC for Opposition of European Patent 2188302B1 dated Apr. 9, 2020. Forwarded in a Communication from the European Patent Office to Mewburn Ellis, Counsel for Genentech, on Apr. 17, 2020.
Opinion of Dr. Ursula Kinkeldey Opinion Cited in Written Submission of Opponent 1 (Grunecker Patentent und Rechtsanwalte PartG mbB) pursuant to Rule 116 EPC for Opposition of EP2188302

(56) References Cited

OTHER PUBLICATIONS dated Apr. 9, 2020. Forwarded in a Communication from the European Patent Office to Mewburn Ellis, Counsel for Genentech, on Apr. 16, 2020, 16 pages.
Opinion of Dr. Ursula Kinkeldey Opinion Cited in Written Submission of Opponent 2 (Grunecker Patenent und Rechtsanwalte PartG mbB) pursuant to Rule 116 EPC for Opposition of EP2586788 dated Apr. 15, 2020. Forwarded in a Communication from the European Patent Office to Mewburn Ellis, Counsel for Genentech, on Apr. 21, 2020, 15 pages.
Qiong, Z. et al. (2006). "Functional Roles of Thioredoxin (Trx)," Molecular Plant Breeding 4(6)(S):78-82. (Translation of the Abstract Only). Cited in Invalidation Proceeding for Chinese Patent Chinese Patent 200880105932.5. Forwarded to Genentech in a Commination from the Chinese Patent Office dated Mar. 31, 2020, 11 pages.
Response to Proprietors Submission by Opponent 8 (Hoffmann Eitle) dated Apr. 9, 2020, for EP Patent No. 2 188 302, Hoffman Elite. Forwarded in a Communication from the European Patent Office to Mewburn Ellis, Counsel for Genentech, on Apr. 16, 2020, 20 pages.
Letter from Opponent 06 (Maiwald) for Opposition of European Patent 2188302B1 dated Apr. 10, 2020. Forwarded in a Communication from the European Patent Office to Mewburn Ellis, Counsel for Genentech, on Apr. 17, 2020, 10 pages.
Communication from Opponent 04 (Cornelia Oetke) Observation pursuant to Rule 116 EPC for Opposition of European Patent 2188302B1 dated Apr. 9, 2020. Forwarded in a Communication from the European Patent Office to Mewburn Ellis, Counsel for Genentech, on Apr. 17, 2020, 24 pages.
Submission under Rule 116 EPC for European Patent 2188302B1 from Opponent 09 (Merck & Sharp EP) dated Apr. 10, 2020. Forwarded in a Communication from the European Patent Office to Mewburn Ellis, Counsel for Genentech, on Apr. 17, 2020, 11 pages.
Final Written Submission Prior to the Oral Proceedings by Opponent 10 (Dr. Hans Ulrich Dorries)—for European Patent No. 2 188 302 dated Apr. 10, 2020. Forwarded in a Communication from the European Patent Office to Mewburn Ellis, Counsel for Genentech, on Apr. 17, 2020, 28 pages.
Written Submission of Opponent 2 (Grunecker Patent und Rechtsanwalte PartG mbB) pursuant to Rule 116 EPC for Opposition of EP2586788 dated Apr. 15, 2020. Forwarded in a Communication from the European Patent Office to Mewburn Ellis, Counsel for Genentech, on Apr. 21, 2020, 48 pages.
Final Submission under Rule 116 EPC by Opponent 3 (Glaxo Group Limited) for Opposition of EP2586788 dated Apr. 15, 2020. Forwarded in a Communication from the European Patent Office to Mewburn Ellis, Counsel for Genentech, on Apr. 21, 2020, 20 pages.
Response to attend Oral Proceedings by Opponent 5 (Maiwald Patentanwalts-und Rechtsanwaltsgesellschaft mbH) for Opposition of EP 2586788 dated Apr. 15, 2020. 12 Pages Forwarded in a Communication from the European Patent office to Mewburn Ellis LLP, Counsel for Genentech on Apr. 21, 2020.
Opponent's Observations Pursuant to Rule 116 EPC by Opponent Cornelia Oetke for Opposition of EP2586788 dated Apr. 15, 2020, for EP 2 586 788 (12178200.7); 35 pages. Forwarded in a Communication from the European Patent office to Mewburn Ellis LLP, Counsel for Genentech on Apr. 21, 2020.
Submission Under Rule 116 EPC by Opponent 9 for Opposition of EP 2586788 dated Apr. 15, 2020, 14 pages. Forwarded in a Communication from the European Patent office to Mewburn Ellis LLP, Counsel for Genentech on Apr. 21, 2020.
Written Submission of Opponent 1 (Grunecker Patenent und Rechtsanwalte PartG mbB) pursuant to Rule 116 EPC for Opposition of EP2188302 dated Apr. 9, 2020. Forwarded in a Communication from the European Patent office to Mewburn Ellis LLP, Counsel for Genentech on Apr. 16, 2020, 37 pages.
Handlogten, M.W. et al. (Jul. 2017). "Glutathione and Thioredoxin Systems Contribute to Recombinant Monoclonal Antibody Interchain Disulfide Bond Reduction During Bioprocessing," Biotechnology & Bioengineering 114(7):1469-1477.

European Examination Report for European Patent Application No. 19181777.4, mailed on Oct. 6, 2020, filed on Jun. 21, 2019, 5 pages.
FDA Label. (Oct. 2012). "Rituxan (rituximab) Injection, for Intravenous Use," FDA Label, 40 pages.
FDA Label. (Mar. 2017). "Ocrevus™ (ocrelizumab) Injection, for Intravenous Use," FDA Label, 18 pages.
Furukawa, K. et al. (1998). "Effect of Culture Temperature on a Recombinant CHO Cell Line Producing a C-Terminal α-Amidating Enzyme," Cytotechnology 26:153-164.
Kinkeldey, U. (Sep. 6, 2019). "Opinion, Law Firm Grünecker Patent-und Rechtsanwaite, Granted Claims of EP Patent No. 2 971 0404," 22 pages.
Response to the Opposition from The Proprietor of the Patent Genentech, Inc., dated Oct. 27, 2020, for European Patent No. 3327026, 50 pages.
Reply from the Opponent to Submission of Proprietor, dated Feb. 16, 2021, for European Patent No. 17196350.7, 20 pages.
Decision of Invalidation, Issued on Jan. 7, 2021, for Chinese Patent Application No. 200880105932.5, filed on Mar. 5, 2010, 43 pages.
Response to Summons dated Jul. 7, 2020, to Attend Oral Proceedings, mailed Mar. 12, 2021, for European Patent Application No. 08781481.0, 14 pages.
Response to EP 2586788 and EP2188302 Point Concerning the Oral Proceedings, dated Mar. 4, 2021, Proprietor: Genentech, Inc.; Opponent 9: Merck Sharp & Dohme Corp., 4 pages.
EP Communication dated Jul. 15, 2020, Annex Communication for European Application No. 2586788, 12 pages.
Opponent's Observations Pursuant to Rule 116 EPC In Preparation for Oral Proceedings, for EP Application No. 2586788, Dated Apr. 13, 2021, Opponent Dr. Cornella Oetke, 23 pages.
EP Communication dated Apr. 7, 2021, for EP Application No. 2188302, Mewburn Ellis, 207 pages.
EP Application No. 2188302, dated Apr. 6, 2021, In Response to the Summons to Attend Oral Proceedings Pursuant to Rule 115(1) EPC dated Jul. 7, 2020, 20 pages.
EP Application No. 2586788, dated Apr. 13, 2021, In Response to the Summons to Attend Oral Proceedings Pursuant to Rule 116 EPC dated Jul. 7, 2020, 24 pages.
EP Letter Response to New Summons dated Mar. 30, 2021, for EP Application No. 2188302, 3 pages.
Maloney, D. G. (2007). "Follicular NHL: From Antibodies and Vaccines to Graft-Versus-Lymphoma Effects," American Society of Hematology 226-232.
EP Opposition Response dated Apr. 7, 2021, Case Law for Claims Containing a Purpose Feature, EP 2188302, 3 pages.
Letter Mewburn Ellis Response dated Apr. 7, 2021, EP Application No. 2188302, 81 pages.
EP Opponent's Observations for EP 2586788, dated Apr. 13, 2021, Pursuant to Rule 116 EPC in preparation for Oral Proceedings, 24 pages.
EP Opponent's Observations for EP 2586788, dated Apr. 15, 2021, Pursuant to Rule 116 EPC in preparation for Oral Proceedings, 34 pages.
European Summons to Attend Oral Proceedings Pursuant to Rule 115(1) EPC, dated Jul. 7, 2020, for European Patent No. 2188302, 23 pages.
European Preliminary Opinion date Jul. 7, 2020, for European Patent No. 2188302, 8 pages.
European Summons to Attend Oral Proceedings Pursuant to Rule 115(1) EPCT, dated Jul. 15, 2020, for European Patent No. 2586788, 10 pages.
European Preliminary Opinion date Jul. 15, 2020, for European Patent No. 2586788, 9 pages.
Response To Proprietor's Response Hexal AG, dated Feb. 17, 2021, for European Patent No. 3327026, 18 pages.
European Summons to Attend Oral Processing Pursuant to Rule 115(1) EPC, dated Apr. 20, 2021, for European Patent No. 2586788, 10 pages.
Declaration of Dr. Corinna Sonderegger, May 13, 2021, for European Patent No. 2 188 302-B1, 2 pages.
Brief Communication for European Patent Application No. 08781481. 0, dated May 21, 2021, 10 pages.

(56) References Cited

OTHER PUBLICATIONS

Brief Communication for European Patent Application No. 19181777.4, mailed on Oct. 1, 2021, filed on Jul. 8, 2008, 8 pages.
Michalski—Hüttermann (Mar. 4, 2020)—Response to Patent Proprietor's Reply to Opposition for European Patent No. 2 586 788-B1, 30 pages.
Floriea, V. (Oct. 1968). "A Table for Converting pH to Hydrogen Ion Concentration [H+] Over the Range 5-9," Federal Aviation Admonition AM 68-23, 32 Pages.
Maiwald Intellectual Property mailed on Apr. 22, 2022, for European Patent No. 3327026, for Patentee: Genentech, Inc., Opponent: Hexal AG, In Response to Summons, date Apr. 23, 2021, 22 Pages.
Response to the Summons to Attend Oral Proceedings Pursuant to Rule 115(1), for EP Patent Application No. 2188302, dated Apr. 12, 2022, Proprietor: Genentech, Inc., Opponent: Dr. Conronelia Oetke, 15 pages.
Response to Rule 115(1) EPC, Carpmaels & Ransford, Dated Apr. 13, 2022, for European Patent No. 2188302, Genentech, Inc., 09: Merck Sharp & Dohme Corp. 9 pages.
INVIVO. "Experimental Work," dated Apr. 12, 2022, EP Patent No. 2188302: O9: Merck Sharp & Dohme Corp., for In Vivo's BioTech Services GmbH, 5 pages.
Response to European Office Action, mailed on Jul. 20, 2016, for European Application No. 13713295.7, filed on Oct. 27, 2014, 19 pages.
Amendment in Response to Non-Final Office Action under 37 C.F.R. §1.111, mailed on Jun. 8, 2017, for U.S. Appl. No. 14/734,848, filed Jun. 9, 2015, 11 pages.
U.S. Appl. No. 16/270,494, filed Feb. 7, 2019, for Laird et al. (A U.S. Patent Application is not submitted herewith pursuant to the waiver of 37 C.F.R. § 1.98(a)(2)(iii) issued by the Office on Sep. 21, 2004.).
Invivo Biotech Services GmbH. (2012). "Experimental Report Discussed in OD's Decision as D153, listed as(D155)," 6 pages.
Smith, A.D. et al. (1997). "Glutamine-Synthetase Adenylytransferase—Glutathione Transferase," Oxford Dictionary of biochemistry and Molecular Biology, Oxford University Press, Oxford, p. 270, 2 p.
Stryer, L. (1996). "Part III. Metabolic Energy," Biochemistry, Fourth Edition, W.H. Freeman and Company, New York, p. 568, 3 pages total.
Therapeutic Monoclonal Antibodies Approved in the EU or US as of Dec. 2023 Source: The Antibody Society, 5 pages.
Expert Opinion of Prof. Dr. Arne Holmgren, dated Aug. 8, 2019, 3 pages.
Wang, W. et al. (Jan. 2007). "Minireview. Antibody Structure, Instability, and Formulation," Journal of Pharmaceutical Sciences 96(1):1-26.
Bardwell, J.C.A. (2002), "Disulfide bond Formation, A Race Between FAD and Oxygen," Developmental Cell 3(6):758-760.
Yuan, Y. (2004). Modern Pharmaceutical Technology, vol. 1, Zhao, G. et al. Deputy Editor, Chemical Industry Press, 20 pages with English Translation.
Sears, D.W. et al. (Jan. 1975). "A Kinetic Study in Vitro of the Reoxidation of Interchain Disulfide Bonds in a Human Immunoglobulin IgGLk. Correlation Between Sulfhydryl Disappearance and Intermediates in Covalent Assembly of H2L2," Proc. Nat. Acad. Sci. USA 72(1):353-357.
Production and Quality Control of Monoclonal Antibodies, (Jul. 1995). 3AB4, Directive 75/318/EEC as Amended, pp. 237-262.
SAFCBioSciences. (Dec. 2006). "Product Information Dulbecco's Modified Eagle's Medium/ Ham's Nutrient Mixture F12," SAFC Biosciences, Catalog No. 51445C, 2 pages.
Communication of the Board of Appeal Pursuant to Article 15(1) of the Rules of Procedure of the Board of Appeal, mailed on Apr. 24, 2024, for EP Patent Application No. 2501799, filed Nov. 19, 2019, 13 pages.
Minutes of the Oral Proceedings mailed on Jun. 20, 2024, for European Patent Application No. 2501799, filed Nov. 19, 2019, 5 pages.

Free Thiol Levels from Dialysis Experiment

In Vitro Activity of Thioredoxin System

In vitro Activity of Thioredoxin System Inhibited by Aurothioglucose

In vitro Activity of Thioredoxin System Inhibited by Aurothiomalate

Inhibition of Ocrelizumab Reduction In HCCF by Aurothiomalate

The Lost Reduction Activity in HCCF Restored by Addition of NADPH

The Lost Reduction Activity in HCCF Restored by Addition of Glucose-6-Phosphate

Light Chain

```
1               15              30              45
DIQMTQSPSSLSASVGDRVTITCRASQDVNTAVAWYQQKPGKAPK
46              60              75              90
LLIYSASFLYSGVPSRFSGSRSGTDFTLTISSLQPEDFATYYCQQ
91        105
HYTTPPTFGQGTKVEIK
```

FIG. 21

Heavy Chain

```
1               15              30              45
EVQLVESGGGLVQPGGSLRLSCAASGFNIKDTYIHWVRQAPGKGL
46              60              75              90
EWVARIYPTNGYTRYADSVKGRFTISADTSKNTAYLQMNSLRAED
91        105       120
TAVYYCSRWGGDGFYAMDYWGQGTLVTVSS
```

FIG. 22

PREVENTION OF DISULFIDE BOND REDUCTION DURING RECOMBINANT PRODUCTION OF POLYPEPTIDES

CROSS REFERENCE TO RELATED APPLICATIONS

This application is a divisional of U.S. application Ser. No. 18/648,209, filed Apr. 26, 2024, which is a divisional of U.S. application Ser. No. 18/194,471, filed Mar. 31, 2023, which is a continuation of U.S. application Ser. No. 17/087,313, filed Nov. 2, 2020, now U.S. Pat. No. 11,639,395, issued May 2, 2023, which is a continuation of U.S. application Ser. No. 16/847,317, filed Apr. 13, 2020, now U.S. Pat. No. 10,906,986, issued Feb. 2, 2021, which is a continuation of U.S. application Ser. No. 16/240,592, filed Jan. 4, 2019, now U.S. Pat. No. 10,759,866, issued Sep. 1, 2020, which is a continuation of U.S. application Ser. No. 15/488,917, filed Apr. 17, 2017, now abandoned, which is a divisional of U.S. application Ser. No. 14/043,758, filed Oct. 1, 2013, now abandoned, which is a divisional of U.S. application Ser. No. 13/354,223, filed Jan. 19, 2012, now U.S. Pat. No. 8,574,869, issued Nov. 5, 2013, which is a continuation of U.S. application Ser. No. 12/217,745, filed Jul. 8, 2008, now abandoned, which is a non-provisional application filed under 37 CFR 1.53 (b)(1), claiming priority under 35 USC 119(e) to provisional Application No. 60/948,677 filed Jul. 9, 2007, the contents of each of which are hereby incorporated by reference in their entirety.

REFERENCE TO AN ELECTRONIC SEQUENCE LISTING

The content of the electronic sequence listing (146392013915seqlist.xml; Size: 53,984 bytes; and Date of Creation: Jun. 14, 2024) is herein incorporated by reference in its entirety.

FIELD OF THE INVENTION

The invention concerns methods and means for preventing the reduction of disulfide bonds during the recombinant production of disulfide-containing polypeptides. In particular, the invention concerns the prevention of disulfide bond reduction during harvesting of disulfide-containing polypeptides, including antibodies, from recombinant host cell cultures.

BACKGROUND OF THE INVENTION

In the biotechnology industry, pharmaceutical applications require a variety of proteins produced using recombinant DNA techniques. Generally, recombinant proteins are produced by cell culture, using either eukaryotic cells, such as mammalian cells, or prokaryotic cells, such as bacterial cells, engineered to produce the protein of interest by insertion of a recombinant plasmid containing the nucleic acid encoding the desired protein. For a protein to remain biologically active, the conformation of the protein, including its tertiary structure, must be maintained during its purification and isolation, and the protein's multiple functional groups must be protected from degradation.

Mammalian cells have become the dominant system for the production of mammalian proteins for clinical applications, primarily due to their ability to produce properly folded and assembled heterologous proteins, and their capacity for post-translational modifications. Chinese hamster ovary (CHO) cells, and cell lines obtained from various other mammalian sources, such as, for example, mouse myeloma (NS0), baby hamster kidney (BHK), human embryonic kidney (HEK-293) and human retinal cells, such as the PER.C6® cell line isolated from a human retinal cell, which provides human glycosylation characteristics, and is able to naturally produce antibodies that match human physiology, have been approved by regulatory agencies for the production of biopharmaceutical products.

Usually, to begin the production cycle, a small number of transformed recombinant host cells are allowed to grow in culture for several days (see, e.g., FIG. 23). Once the cells have undergone several rounds of replication, they are transferred to a larger container where they are prepared to undergo fermentation. The media in which the cells are grown and the levels of oxygen, nitrogen and carbon dioxide that exist during the production cycle may have a significant impact on the production process. Growth parameters are determined specifically for each cell line and these parameters are measured frequently to assure optimal growth and production conditions.

When the cells grow to sufficient numbers, they are transferred to large-scale production tanks and grown for a longer period of time. At this point in the process, the recombinant protein can be harvested. Typically, the cells are engineered to secrete the polypeptide into the cell culture media, so the first step in the purification process is to separate the cells from the media. Typically, harvesting includes centrifugation and filtration to produce a Harvested Cell Culture Fluid (HCCF). The media is then subjected to several additional purification steps that remove any cellular debris, unwanted proteins, salts, minerals or other undesirable elements. At the end of the purification process, the recombinant protein is highly pure and is suitable for human therapeutic use.

Although this process has been the subject of much study and improvements over the past several decades, the production of recombinant proteins is still not without difficulties. Thus, for example, during the recombinant production of polypeptides comprising disulfide bonds, especially multi-chain polypeptides comprising inter-chain disulfide bonds such as antibodies, it is essential to protect and retain the disulfide bonds throughout the manufacturing, recovery and purification process, in order to produce properly folded polypeptides with the requisite biological activity.

SUMMARY OF THE INVENTION

The instant invention generally relates to a method for preventing reduction of a disulfide bond in a polypeptide expressed in a recombinant host cell, comprising supplementing the pre-harvest or harvested culture fluid of the recombinant host cell with an inhibitor of thioredoxin or a thioredoxin-like protein.

In one embodiment, the thioredoxin inhibitor is added to the pre-harvest culture fluid.

In another embodiment, the thioredoxin inhibitor is added to the harvested culture fluid.

In a further embodiment, the thioredoxin inhibitor is a direct inhibitor of thioredoxin.

In all embodiments, the thioredoxin inhibitor may, for example, be an alkyl-2-imidazolyl disulfide or a naphthoquinone spiroketal derivative.

In a further embodiment, the thioredoxin inhibitor is a specific inhibitor of thioredoxin reductase.

In a still further embodiment, the thioredoxin inhibitor is a gold complex, where the gold complex may, for example, be aurothioglucose (ATG) or aurothiomalate (ATM). While the effective inhibitory concentration may vary, it typically is between about 0.1 mM and 1 mM. Similarly, the minimum effective inhibitory concentration varies depending on the nature of the polypeptide and overall circumstances, and is typically reached when the ATG or ATG concentration is at least about four-times of thioreduxin concentration in the pre-harvest or harvested culture fluid.

In another embodiment of this aspect of the invention, the thioredoxin inhibitor is a metal ion, where the metal ion, without limitation, may be selected from the group consisting of $Hg^{2+}$, $Cu^{2+}$, $Zn^{2+}$, $Co^{2+}$, and $Mn^{2+}$. When the metal ion is added in the form of cupric sulfate, the effective inhibitory concentration generally is between about 5 µM and about 100 µM, or between about 10 µM and about 80 µM, or between about 15 µM and about 50 µM. The minimum inhibitory concentration of cupric sulfate also varies, but typically is reached when cupric sulfate is added at a concentration at least about two-times of thioredoxin concentration in the pre-harves or harvested culture fluid.

In different embodiment, the thioredoxin inhibitor is an oxidizing agent, e.g., an inhibitor of G6PD, such as, for example, pyridoxal 5'-phosphate, 1 fluoro-2,4 dinitrobenzene, dehydroepiandrosterone (DHEA) or epiandrosterone (EA); cystine or cysteine. Typical effective inhibitor concentrations of DHEA are between abour 0.05 mM and about 5 mM, or between about 0.1 mM and about 2.5 mM.

In a further embodiment, the thioredoxin inhibitor is an inhibitor of hexokinase activity, including, without limitation, chelators of metal ions, such as, for example, ethylenediamine tetraacetic acid (EDTA). EDTA is typically added and effective at a concentration between about 5 mM and about 60 mM, or about 10 mM and about 50 mM, or about 20 mM and about 40 mM.

In other preferred embodiments, the inhibitor of hexokinase activity is selected from the group consisting of sorbose-1-phosphate, polyphosphates, 6-deoxy-6-fluoroglucose, 2-C-hydroxy-methylglucose, xylose, and lyxose.

Other inhibitors include cystine, cysteine, and oxidized glutathione which are typically added at a concentration at least about 40-times of the concentration of the polypeptide in question in the pre-harvest or harvested culture fluid.

In a still further embodiment, the thioredoxin inhibitor is an siRNA, an antisense nucleotide, or an antibody specifically binding to a thioredoxin reductase.

In another embodiment, the thioredoxin inhibitor is a measure indirectly resulting in the inhibition of thioredoxin activity. This embodiment includes, for example, air sparging the harvested culture fluid of the recombinant host cell, and/or lowering the pH of the harvested culture fluid of the recombinant host cell.

In various embodiments, indirect means for inhibiting thioredoxin activity, such as air sparging and/or lowering of the pH, can be combined with the use of direct thioredoxin inhibitors, such as those listed above.

In all embodiments, the polypeptide may, for example, be an antibody, or a biologically functional fragment of an antibody. Representative antibody fragments include Fab, Fab', $F(ab')_2$, scFv, $(scFv)_2$, dAb, complementarity determining region (CDR) fragments, linear antibodies, single-chain antibody molecules, minibodies, diabodies, and multispecific antibodies formed from antibody fragments.

Therapeutic antibodies include, without limitation, anti-HER2 antibodies anti-CD20 antibodies; anti-IL-8 antibodies; anti-VEGF antibodies; anti-CD40 antibodies, anti-CD11a antibodies; anti-CD18 antibodies; anti-IgE antibodies; anti-Apo-2 receptor antibodies; anti-Tissue Factor (TF) antibodies; anti-human $\alpha_4\beta_7$ integrin antibodies; anti-EGFR antibodies; anti-CD3 antibodies; anti-CD25 antibodies; anti-CD4 antibodies; anti-CD52 antibodies; anti-Fc receptor antibodies; anti-carcinoembryonic antigen (CEA) antibodies; antibodies directed against breast epithelial cells; antibodies that bind to colon carcinoma cells; anti-CD38 antibodies; anti-CD33 antibodies; anti-CD22 antibodies; anti-EpCAM antibodies; anti-GpIIb/IIIa antibodies; anti-RSV antibodies; anti-CMV antibodies; anti-HIV antibodies; anti-hepatitis antibodies; anti-CA 125 antibodies; anti-$\alpha v \beta 3$ antibodies; anti-human renal cell carcinoma antibodies; anti-human 17-1A antibodies; anti-human colorectal tumor antibodies; anti-human melanoma antibody R24 directed against GD3 ganglioside; anti-human squamous-cell carcinoma; and anti-human leukocyte antigen (HLA) antibodies, and anti-HLA DR antibodies.

In other embodiments, the therapeutic antibody is an antibody binding to a HER receptor, VEGF, IgE, CD20, CD11a, CD40, or DR5.

In a further embodiment, the HER receptor is HER1 and/or HER2, preferably HER2. The HER2 antibody may, for example, comprise a heavy and/or light chain variable domain sequence selected from the group consisting of SEQ ID NO: 16, 17, 18, and 19.

In another embodiment, the therapeutic antibody is an antibody that binds to CD20. The anti-CD20 antibody may, for example, comprise a heavy and/or light chain variable domain sequence selected from the group consisting of SEQ ID NOS: 1 through 15.

In yet another embodiment, the therapeutic antibody is an antibody that binds to VEGF. The anti-VEGF antibody may, for example, comprise a heavy and/or light chain variable domain sequence selected from the group consisting of SEQ ID NOS: 20 through 25.

In an additional embodiment, the therapeutic antibody is an antibody that binds CD11a. The anti-CD11a antibody may, for example, comprise a heavy and/or light chain variable domain sequence selected from the group consisting of SEQ ID NOS: 26 through 29.

In a further embodiment, the therapeutic antibody binds to a DR5 receptor. The anti-DR5 antibody may, for example, be selected from the group consisting of Apomabs 1.1, 2.1, 3.1, 4.1, 5.1, 5.2, 5.3, 6.1, 6.2, 6.3, 7.1, 7.2, 7.3, 8.1, 8.3, 9.1, 1.2, 2.2, 3.2, 4.2, 5.2, 6.2, 7.2, 8.2, 9.2, 1.3, 2.2, 3.3, 4.3, 5.3, 6.3, 7.3, 8.3, 9.3, and 25.3, and preferably is Apomab 8.3 or Apomab 7.3, and most preferably Apomab 7.3.

In other embodiments of the method of the present invention, the polypeptide expressed in the recombinant host cell is a therapeutic polypeptide. For example, the therapeutic polypeptide can be selected from the group consisting of a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of said polypeptides.

In all embodiments, the recombinant host cell can be an eukaryotic host cell, such as a mammalian host cell, including, for example, Chinese Hamster Ovary (CHO) cells.

In all embodiments, the recombinant host cell can also be a prokaryotic host cell, such as a bacterial cell, including, without limitation, *E. coli* cells.

BRIEF DESCRIPTION OF THE DRAWINGS

FIG. 21 shows the $V_L$ (SEQ ID NO. 24) amino acid sequence of an anti-Her2 antibody (Trastuzumab).

FIG. 22 shows the $V_H$ (SEQ ID No. 25) amino acid sequence of an anti-Her2 antibody (Trastuzumab).

μM thioredoxin reductase, 2 mM glucose, 0.6 mM ATP, 2 mM Mg$^{2+}$, and 2 mM NADP in 50 mM histidine sulfate buffer at pH=7.38.

Figure 41:
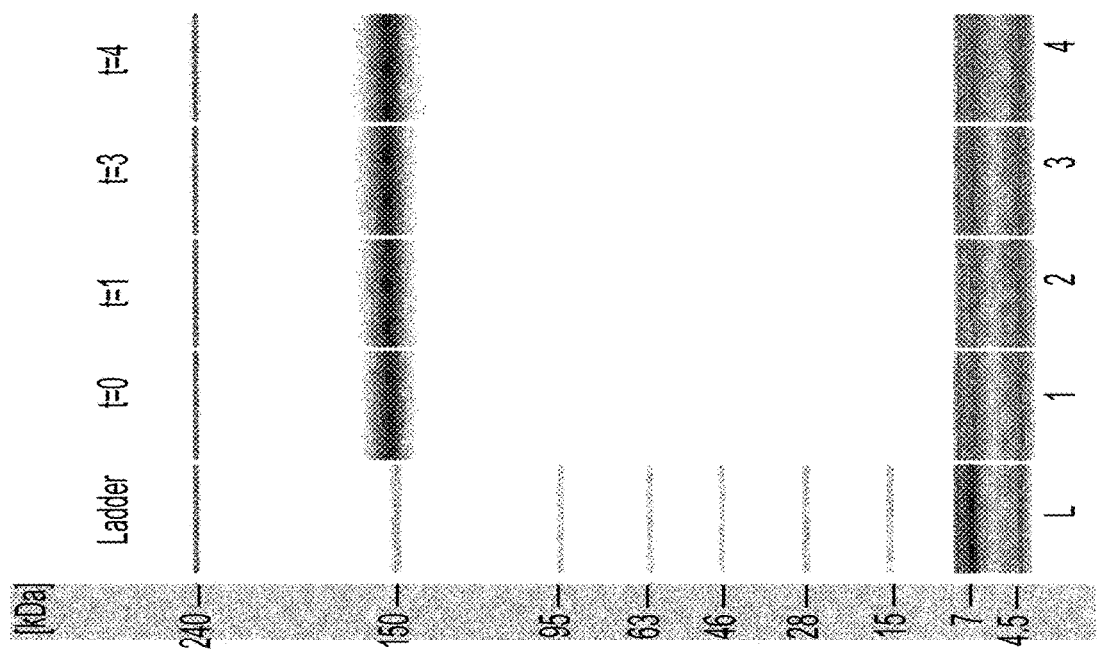

FIG. 41 The thioredoxin system requires NADPH. 1 mg/ml 2H7 (Variant A)+5 μM thioredoxin, 0.1 μM thioredoxin reductase, and 2 mM NADP in 50 mM histidine sulfate buffer at pH=7.38.

DETAILED DESCRIPTION OF THE PREFERRED EMBODIMENTS

I. Definitions

In the present invention, in the context of proteins, including antibodies, in general, or with regard to any specific protein or antibody, the term "reduction" is used to refer to the reduction of one or more disulfide bonds of the protein or antibody. Thus, for example, the terms "ocrelizumab reduction" is used interchangeably with the term "ocrelizumab disulfide bond reduction" and the term "antibody (Ab) reduction" is used interchangeably with the term "antibody (Ab) disulfide bond reuction."

The terms "reduction" or "disulfide bond reduction" are used in the broadest sense, and include complete and partial reduction and reduction of some or all of the disulfide bonds, interchain or intrachain, present in a protein such as an antibody.

By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD. Examples of proteins encompassed within the definition herein include all mammalian proteins, in particular, therapeutic and diagnostic proteins, such as therapeutic and diagnostic antibodies, and, in general proteins that contain one or more disulfide bonds, including multi-chain polypeptides comprising one or more inter- and/or intrachain disulfide bonds.

The term "therapeutic protein" or "therapeutic polypeptide" refers to a protein that is used in the treatment of disease, regardless of its indication or mechanism of action. In order for therapeutic proteins to be useful in the clinic it must be manufactured in large quantities. "Manufacturing scale" production of therapeutic proteins, or other proteins, utilize cell cultures ranging from about 400 L to about 80,000 L, depending on the protein being produced and the need. Typically such manufacturing scale production utilizes cell culture sizes from about 400 L to about 25,000 L. Within this range, specific cell culture sizes such as 4,000 L, about 6,000 L, about 8,000, about 10,000, about 12,000 L, about 14,000 L, or about 16,000 L are utilized.

The term "therapeutic antibody" refers to an antibody that is used in the treatment of disease. A therapeutic antibody may have various mechanisms of action. A therapeutic antibody may bind and neutralize the normal function of a target associated with an antigen. For example, a monoclonal antibody that blocks the activity of the of protein needed for the survival of a cancer cell causes the cell's death. Another therapeutic monoclonal antibody may bind and activate the normal function of a target associated with an antigen. For example, a monoclonal antibody can bind to a protein on a cell and trigger an apoptosis signal. Yet another monoclonal antibody may bind to a target antigen expressed only on diseased tissue; conjugation of a toxic payload (effective agent), such as a chemotherapeutic or radioactive agent, to the monoclonal antibody can create an agent for specific delivery of the toxic payload to the diseased tissue, reducing harm to healthy tissue. A "biologically functional fragment" of a therapeutic antibody will exhibit at least one if not some or all of the biological functions attributed to the intact antibody, the function comprising at least specific binding to the target antigen.

The term "diagnostic protein" refers to a protein that is used in the diagnosis of a disease.

The term "diagnostic antibody" refers to an antibody that is used as a diagnostic reagent for a disease. The diagnostic antibody may bind to a target antigen that is specifically associated with, or shows increased expression in, a particular disease. The diagnostic antibody may be used, for example, to detect a target in a biological sample from a patient, or in diagnostic imaging of disease sites, such as tumors, in a patient. A "biologically functional fragment" of a diagnostic antibody will exhibit at least one if not some or all of the biological functions attributed to the intact antibody, the function comprising at least specific binding to the target antigen.

"Purified" means that a molecule is present in a sample at a concentration of at least 80-90% by weight of the sample in which it is contained.

The protein, including antibodies, which is purified is preferably essentially pure and desirably essentially homogeneous (i.e. free from contaminating proteins etc.).

An "essentially pure" protein means a protein composition comprising at least about 90% by weight of the protein, based on total weight of the composition, preferably at least about 95% by weight.

An "essentially homogencous" protein means a protein composition comprising at least about 99% by weight of protein, based on total weight of the composition.

As noted above, in certain embodiments, the protein is an antibody. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The term "antibody" is used in the broadest sense and specifically covers monoclonal antibodies (including full length antibodies which have an immunoglobulin Fc region), antibody compositions with polyepitopic specificity, bispecific antibodies, diabodies, and single-chain molecules such as scFv molecules, as well as antibody fragments (e.g., Fab,F(ab')$_2$, and Fv).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256:495 (1975); Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., *Proc. Natl. Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; 5,661,016; Marks et al., *BioTechnology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996) and Lonberg and Huszar, *Intern. Rev. Immunol.* 13:65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994). The humanized antibody includes a Primatized™ antibody wherein the antigen-binding region of the antibody is derived from an antibody produced by immunizing macaque monkeys with the antigen of interest.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs/HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., *Bio/Technology* 10:779-783 (1992) describes affinity maturation by $V_H$ and $V_L$ domain shuffling. Random mutagenesis of CDR/HVR and/or framework residues is described by: Barbas et al., *Proc Nat. Acad. Sci. USA* 91:3809-3813 (1994); Schier et al., *Gene* 169:147-155 (1995); Yelton et al., *J. Immunol.* 155:1994-2004 (1995); Jackson et al., *J. Immunol.* 154(7):3310-9 (1995); and Hawkins et al., *J. Mol. Biol.* 226:889-896 (1992).

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, MD (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called a, d, e, g, and m, respectively. The subunit structures and three-dimensional configurations of different classes of immunoglobulins are well known and described generally in, for example, Abbas et al., Cellular and *Mol. Immunology*, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields anF(ab')$_2$ fragment that has two antigen-combining sites and is still capable of cross-linking antigen.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group.F(ab')2 antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "scFv" antibody fragments comprise the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO93/1161; Hudson et al., (2003) *Nat. Med.* 9:129-134; and Hollinger et al., *Proc. Natl. Acad. Sci. USA* 90:6444-6448 (1993). Triabodies and tetrabodies are also described in Hudson et al., (2003) *Nat. Med.* 9:129-134.

The antibody may bind to any protein, including, without limitation, a member of the HER receptor family, such as HER1 (EGFR), HER2, HER3 and HER4; CD proteins such as CD3, CD4, CD8, CD19, CD20, CD21, CD22, and CD34; cell adhesion molecules such as LFA-1, Mol, p150,95, VLA-4, ICAM-1, VCAM and av/p3 integrin including either α or β or subunits thereof (e.g. anti-CD11a, anti-CD18 or anti-CD11b antibodies); growth factors such as vascular endothelial growth factor (VEGF); IgE; blood group antigens; flk2/flt3 receptor; obesity (OB) receptor; and protein C. Other exemplary proteins include growth hormone (GH), including human growth hormone (hGH) and bovine growth hormone (bGH); growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin (HSA); mullerian-inhibiting substance; relaxin A-chain; relaxin B-chain; prorelaxin; mouse gonadotropin-associated peptide; DNase; inhibin; activin; receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins (IGFBPs); erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides. Many other antibodies and/or other proteins may be used in accordance with the instant invention, and the above lists are not meant to be limiting.

A "biologically functional fragment" of an antibody comprises only a portion of an intact antibody, wherein the portion retains at least one, and as many as most or all, of the functions normally associated with that portion when present in an intact antibody. In one embodiment, a biologically functional fragment of an antibody comprises an antigen binding site of the intact antibody and thus retains the ability to bind antigen. In another embodiment, a biologically functional fragment of an antibody, for example one that comprises the Fc region, retains at least one of the biological functions normally associated with the Fc region when present in an intact antibody, such as FcRn binding, antibody half life modulation, ADCC function and complement binding. In one embodiment, a biologically functional fragment of an antibody is a monovalent antibody that has an in vivo half life substantially similar to an intact antibody. For example, such a biologically functional fragment of an antibody may comprise an antigen binding arm linked to an Fc sequence capable of conferring in vivo stability to the fragment.

The terms "thioredoxin inhibitor" and "Trx inhibitor" are used interchangeably, and include all agents and measures effective in inhibiting thioredoxin activity. Thus, thioredoxin (Trx) inhibitors include all agents and measures blocking any component of the Trx, G6PD and/or hexokinase enzyme systems. In this context, "inhibition" includes complete elimination (blocking) and reduction of thioredoxin activity, and, consequently, complete or partial elimination of disulfide bond reduction in a protein, such as an antibody.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a $C_H2/C_H3$ region, such as an Fc region. Protein A can be purchased commercially from Repligen, GE Healthcare and Fermatech. Protein A is generally immobilized on a solid phase support material. The term "ProA" also refers to an affinity chromatography resin or column containing chromatographic solid support matrix to which is covalently attached Protein A.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "affinity chromatography" and "protein affinity chromatography" are used interchangeably herein and refer to a protein separation technique in which a protein of interest or antibody of interest is reversibly and specifically bound to a biospecific ligand. Preferably, the biospecific ligand is covalently attached to a chromatographic solid phase material and is accessible to the protein of interest in solution as the solution contacts the chromatographic solid phase material. The protein of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "non-affinity chromatography" and "non-affinity purification" refer to a purification process in which affinity chromatography is not utilized. Non-affinity chromatography includes chromatographic techniques that rely on non-specific interactions between a molecule of interest (such as a protein, e.g. antibody) and a solid phase matrix.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g. SP-SEPHAROSE FAST FLOW™ or SP-SEPHAROSE HIGH PERFORMANCE™, from GE Healthcare) and sulphonyl immobilized on agarose (e.g. S-SEPHAROSE FAST FLOW™ from GE Healthcare). A "mixed mode ion exchange resin" refers to a solid phase which is covalently modified with cationic, anionic, and hydrophobic moieties. A commercially available mixed mode ion exchange resin is BAKERBOND ABX™ (J. T. Baker, Phillipsburg, NJ) containing weak cation exchange groups, a low concentration of anion exchange groups, and hydrophobic ligands attached to a silica gel solid phase support matrix.

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPH-ADEX™ and FAST Q SEPHAROSE™ (GE Healthcare).

A "buffer" is a solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these.

The "loading buffer" is that which is used to load the composition comprising the polypeptide molecule of interest and one or more impurities onto the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin.

The "intermediate buffer" is used to elute one or more impurities from the ion exchange resin, prior to eluting the polypeptide molecule of interest. The conductivity and/or pH of the intermediate buffer is/are such that one or more impurity is eluted from the ion exchange resin, but not significant amounts of the polypeptide of interest.

The term "wash buffer" when used herein refers to a buffer used to wash or re-equilibrate the ion exchange resin, prior to eluting the polypeptide molecule of interest. Conveniently, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

A "regeneration buffer" may be used to regenerate the ion exchange resin such that it can be re-used. The regeneration buffer has a conductivity and/or pH as required to remove substantially all impurities and the polypeptide of interest from the ion exchange resin.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein with regard to amounts or numerical values (and not as reference to the chemical process of reduction), denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B.

It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Percent (%) nucleic acid sequence identity" is defined as the percentage of nucleotides in a candidate sequence that are identical with the nucleotides in a reference Factor D-encoding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Treatment" refers to both therapeutic treatment and prophylactic or preventative measures. Those in need of treatment include those already with the disorder as well as those in which the disorder is to be prevented. "Treatment" herein encompasses alleviation of the disease and of the signs and symptoms of the particular disease.

A "disorder" is any condition that would benefit from treatment with the protein. This includes chronic and acute disorders or diseases including those pathological conditions which predispose the mammal to the disorder in question. Non-limiting examples of disorders to be treated herein include carcinomas and allergies.

"Mammal" for purposes of treatment refers to any animal classified as a mammal, including humans, non-human higher primates, other vertebrates, domestic and farm animals, and zoo, sports, or pet animals, such as dogs, horses, cats, cows, etc. Preferably, the mammal is human.

An "interfering RNA" or "small interfering RNA (siRNA)" is a double stranded RNA molecule less than about 30 nucleotides in length that reduces expression of a target gene. Interfering RNAs may be identified and synthesized using known methods (Shi Y., Trends in Genetics 19(1): 9-12 (2003), WO/2003056012 and WO2003064621), and siRNA libraries are commercially available, for example from Dharmacon, Lafayette, Colorado. Frequently, siRNAs can be successfully designed to target the 5' end of a gene.

II. Compositions and Methods of the Invention

The practice of the present invention will employ, unless otherwise indicated, conventional techniques of molecular biology and the like, which are within the skill of the art. Such techniques are explained fully in the literature. Sec e.g., *Molecular Cloning: A Laboratory Manual*, (J. Sambrook et al., Cold Spring Harbor Laboratory, Cold Spring Harbor, N.Y., 1989); *Current Protocols in Molecular Biology* (F. Ausubel et al., eds., 1987 updated); *Essential Molecular Biology* (T. Brown ed., IRL Press 1991); *Gene Expression Technology* (Goeddel ed., Academic Press 1991); *Methods for Cloning and Analysis of Eukaryotic Genes* (A. Bothwell et al., eds., Bartlett Publ. 1990); *Gene Transfer and Expression* (M. Kriegler, Stockton Press 1990); *Recombinant DNA Methodology II* (R. Wu et al., eds., Academic Press 1995); *PCR: A Practical Approach* (M. McPherson et al., IRL Press at Oxford University Press 1991); *Oligonucleotide Synthesis* (M. Gait ed., 1984); *Cell Culture for Biochemists* (R. Adams ed., Elsevier Science Publishers 1990); *Gene Transfer Vectors for Mammalian Cells* (J. Miller & M. Calos eds., 1987); *Mammalian Cell Biotechnology* (M. Butler ed., 1991); *Animal Cell Culture* (J. Pollard et al., eds., Humana Press 1990); *Culture of Animal Cells*, $2^{nd}$ Ed. (R. Freshney et al., eds., Alan R. Liss 1987); *Flow Cytometry and Sorting* (M. Melamed et al., eds., Wiley-Liss 1990); the series *Methods in Enzymology* (Academic Press, Inc.); Wirth M. and Hauser H. (1993); *Immunochemistry in Practice*, 3rd edition, A. Johnstone & R. Thorpe, Blackwell Science, Cambridge, MA, 1996; Techniques in Immunocytochemistry, (G. Bullock & P. Petrusz eds., Academic Press 1982, 1983, 1985, 1989); Handbook of Experimental Immunology, (D. Weir & C. Blackwell, eds.); *Current Protocols in Immunology* (J. Coligan et al., eds. 1991); *Immunoassay* (E. P. Diamandis & T. K. Christopoulos, eds., Academic Press, Inc., 1996); Goding (1986) *Monoclonal Antibodies: Principles and Practice* (2d ed) Academic Press, New York; Ed Harlow and David Lane, *Antibodies A laboratory Manual*, Cold Spring Harbor Laboratory, Cold Spring Harbor, New York, 1988; *Antibody Engineering*, $2^{nd}$ edition (C. Borrebaeck, ed., Oxford University Press, 1995); and the series *Annual Review of Immunology*; the series *Advances in Immunology*.

1. Prevention of Disulfide Bond Reduction

The present invention concerns methods for the prevention of the reduction of disulfide bonds of proteins during recombinant production. In particular, the invention concerns methods for preventing the reduction of disulfide bonds of recombinant proteins during processing following fermentation. The methods of the invention are particularly valuable for large scale production of disulfide bond containing proteins, such as at a manufacturing scale. In one embodiment, the methods of the invention are useful for large scale protein production at a scale of greater than 5,000 L.

It has been experimentally found that disulfide bond reduction occurs during processing of the Harvested Cell Culture Fluid (HCCF) produced during manufacturing of recombinant proteins that contain disulfide bonds. Typically, this reduction is observed after cell lysis, especially mechanical cell lysis during harvest operations, when it reaches a certain threshold, such as, for example, from about 30% to about 70%, or from about 40% to about 60%, or from about 50% to about 60% total cell lysis. This threshold will vary, depending on the nature of the protein (e.g. antibody) produced, the recombinant host, the production system, production parameters used, and the like, and can be readily determined experimentally.

Theoretically, such reduction might result from a variety of factors and conditions during the manufacturing process, and might be caused by a variety of reducing agents. The present invention is based, at least in part, on the recognition that the root cause of this reduction is an active thioredoxin (Trx) or thioredoxin-like system in the HCCF.

The Trx enzyme system, composed of Trx, thioredoxin reductase (TrxR) and NADPH, is a hydrogen donor system for reduction of disulfide bonds in proteins. Trx is a small monomeric protein with a CXXC active site motif that catalyzes many redox reactions through thiol-disulfide exchange. The oxidized Trx can be reduced by NADPH via TrxR. The reduced Trx is then able to catalyze the reduction of disulfides in proteins. The NADPH required for thioredoxin system is provided via reactions in pentose phosphate pathway and glycolysis. The results presented herein demonstrate that NADPH, which is required for activity of the Trx system is provided by glucose-6-phosphate dehydrogenase (G6PD) activity, which generates NADPH from glucose and ATP by hexokinase (see FIG. 4). These cellular enzymes (Trx system, G6PD, and hexokinase) along with their substrates are released into the CCF upon cell lysis, allowing reduction to occur. Accordingly, disulfide reduction can be prevented by inhibitors of the Trx enzyme system or upstream enzyme systems providing components for an active Trx system, such as G6PD and hexokinase activity.

For further details of these enzyme systems, or regarding other details of protein production, see, for example: Babson, A. L. and Babson, S. R. (1973) Kinetic Colorimetric Measurement of Serum Lactate Dehydrogenase Activity. *Clin. Chem.* 19:766-769; Michael W. Laird et al., "Optimization of BLyS Production and Purification from *Eschericia coli,*" *Protein Expression and Purification* 39:237-246 (2005); John C. Joly et al., "Overexpression of *Eschericia coli* Oxidoreductases Increases Recombinant Insulin-like Growth Factor-I Accumulation," Proc. Natl. Acad. Sci. USA 95:2773-2777 (March 1998); Dana C. Andersen et al., "Production Technologies for Monoclonal Antibodies and Their Fragments," *Current Opinion in Biotechnology* 15:456-462 (2004); Yariv Mazor et al., "Isolation of Engineered, Full-length Antibodies from Libraries Expressed in *Escherichia coli,*" *Nature Biotech.* 25, 563-565 (1 Jun. 2007); Laura C. Simmons et al., "Expression of Full-length Immunoglobulins in *Escherichia coli*: Rapid and Efficient Production of Aglycosylated Antibodies," *Journal of Immunological Methods* 263:133-147 (2002); Paul H. Bessette et al., "Efficient Folding of Proteins with Multiple Disulfide Bonds in the *Escherichia coli* cytoplasm," Proc. Natl. Acad. Sci. 96(24):13703-08 (1999); Chaderjian, W. B., Chin, E. T., Harris, R. J., and Etcheverry, T. M., (2005) "Effect of copper sulfate on performance of a serum-free CHO cell culture process and the level of free thiol in the recombinant antibody expressed," *Biotechnol. Prog.* 21:550-553; Gordon G., Mackow M. C., and Levy H. R., (1995) "On the mechanism of interaction of steroids with human glucose 6-phosphate dehydrogenase," Arch. Biochem. Biophys. 318: 25-29; Gromer S., Urig S., and Becker K., (2004) "TheTrx System—From Science to Clinic," Medicinal Research Reviews, 24:40-89; Hammes G. G. and Kochavi D., (1962a) "Studies of the Enzyme Hexokinase. I. Steady State Kinetics at pH 8," J. Am. Chem. Soc. 84:2069-2073; Hammes G. G. and Kochavi D., (1962b) "Studies of the Enzyme Hexokinase. III. The Role of the Metal Ion," J. Am. Chem. Soc. 84:2076-2079; Johansson C., Lillig C. H., and Holmgren A., (2004) "Human Mitochondrial Glutaredoxin Reduces S-Glutathionylated Proteins with High Affinity Accepting Electrons from Either Glutathione or Thioredoxin Reductase," J. Biol. Chem. 279:7537-7543; Legrand, C., Bour, J. M., Jacob, C., Capiaumont J., Martial, A., Marc, A., Wudtke, M., Kretzmer, G., Demangel, C., Duval, D., and Hache J., (1992) "Lactate Dehydrogenase (LDH) Activity of the Number of Dead Cells in the Medium of Cultured Eukaryotic Cells as Marker," J. Biotechnol., 25:231-243; McDonald, M. R., (1955) "Yeast Hexokinase: ATP+Hexose→Hexose-6-phosphate+ADP," Methods in Enzymology, 1:269-276, Academic Press, NY; Sols, A., DelaFuente, G., Villar-Palasi, C., and Asensio, C., (1958) "Substrate Specificity and Some Other Properties of Bakers' Yeast Hexokinase," Biochim Biophys Acta 30:92-101; Kirkpatrick D. L., Kuperus M., Dowdeswell M., Potier N., Donald L. J., Kunkel M., Berggren M., Angulo M., and Powis G., (1998) "Mechanisms of inhibition of the Trx growth factor system by antitumor 2-imidazolyl disulfides," Biochem. Pharmacol. 55:987-994; Kirkpatrick D. L., Watson S., Kunkel M., Fletcher S., Ulhaq S., and Powis G., (1999) "Parallel syntheses of disulfide inhibitors of the Trx redox system as potential antitumor agents," Anticancer Drug Des. 14:421-432; Milhausen, M., and Levy, H. R., (1975) "Evidence for an Essential Lysine in G6PD from *Leuconostoc mesenteroides,*" Eur. J. Biochem. 50:453-461; Pleasants, J. C., Guo, W., and Rabenstein, D. L., (1989) "A comparative study of the kinetics of selenol/diselenide and thiol/disulfide exchange reactions," J. Am. Chem. Soc. 111:6553-6558; Whitesides, G. M., Lilburn, J. E., and Szajewski, R. P., (1977) "Rates of thioldisulfide interchange reactions between mono- and dithiols and Ellman's reagent," J. Org. Chem. 42:332-338; and Wipf P., Hopkins T. D., Jung J. K., Rodriguez S., Birmingham A., Southwick E. C., Lazo J. S., and Powis G, (2001) "New inhibitors of the Trx-TrxR system based on a naphthoquinone spiroketal natural product lead," *Bioorg. Med. Chem. Lett.* 11:2637-2641.

According to one aspect of the present invention, disulfide bond reduction can be prevented by blocking any component of the Trx, G6PD and hexokinase enzyme systems. Inhibitors of these enzyme systems are collectively referred to herein as "thioredoxin inhibitors," or "Trx inhibitors." The Trx inhibitors are typically added to the cell culture fluid (CCF), which contains the recombinant host cells and the culture media, and/or to the harvested cell culture fluid (HCCF), which is obtained after harvesting by centrifugation, filtration, or similar separation methods. The HCCF lacks intact host cells but typically contains host cell proteins and other contaminants, including DNA, which are removed in subsequent purification steps. Thus, the Trx inhibitors may be added before harvest and/or during harvest, preferably before harvest.

Alternatively or in addition other, non-specific methods can also be used to prevent the reduction of disulfide bond reduction following fermentation during the recombinant production of recombinant proteins, such as air sparging or pH adjustment. Certain reduction inhibition methods contemplated herein are listed in the following Table 1.

TABLE 1

Reduction Inhibition Methods

| Method[1] | Purpose |
|---|---|
| Addition of EDTA, EGTA, or citrate | To inhibit hexokinase |
| Addition of sorbose-1-phosphate, polyphosphates, 6-deoxy-6-fluoroglucose, 2-C-hydroxy-methylglucose, xylose, or lyxose | To inhibit hexokinase |
| Addition of epiandrosterone or dehydroepiandrosterone (DHEA) | To inhibit G6PD |
| Addition of pyridoxal 5'-phosphate or 1-fluoro-2,4-dinitrobenzene | To inhibit G6PD |
| Addition of metal ions such as $Cu^{2+}$, $Zn^{2+}$ $Hg^{2+}$, $Co^{2+}$, or $Mn^{2+}$ | To inhibit Trx system |
| Addition of alkyl-2-imidazolyl disulfides and related compounds (e.g., 1 methylpropyl-2-imidazolyl disulfide[2]) or naphthoquinone spiroketal derivatives (e.g. palmarumycin $CP_1$[2]) | To inhibit Trx |
| Addition of aurothioglucose (ATG) or aurothiomalate (ATM) | To inhibit TrxR |
| Air sparging | To deplete G6P and NADPH; oxidizing agent |
| Cystine | Oxidizing agent |
| Oxidized glutathione | Oxidizing agents |
| pH Adjustment to below 6.0 | To reduce thiol-disulfide exchange rate and Trx system activity |

[1]Applied to CCF prior to harvest or in HCCF immediately after harvest.
[2]Currently not available commercially.

"Trx inhibitors" for use in the methods of the present invention include, without limitation, (1) direct inhibitors of Trx, such as alkyl-2-imidazolyl disulfides and related compounds (e.g., 1 methylpropyl-2-imidazolyl disulfide) (Kirkpatrick et al., 1998 and 1999, supra) and naphthoquinone spiroketal derivatives (e.g., palmarumycin $CP_1$) (Wipf et al., 2001, supra); (2) specific inhibitors of TrxR, including gold complexes, such as aurothioglucose (ATG) and aurothiomalate (ATM) (see, e.g., the review by Gromer et al., 2004), which are examples of irreversible inhibitors of TrxR; (3) metal ions, such as $Hg^{2+}$, $Cu^{2+}$, $Zn^{2+}$, $Co^{2+}$, and $Mn^{2+}$, which can form readily complexes with thiols and selenols, and thus can be used in embodiments of the instant invention as inhibitors of TrxR or Trx; (4) inhibitors of G6PD, such as, for example, pyridoxal 5'-phosphate and 1 fluoro-2,4 dinitrobenzene (Milhausen and Levy 1975, supra), certain steroids, such as dehydroepiandrosterone (DHEA) and epiandrosterone (EA) (Gordon et al., 1995, supra); and (4) inhibitors of hexokinase activity (and thereby production of G6P for the G6PD), including chelators of metal ions, e.g. $Mg^{2+}$, such as EDTA, and compounds that react with SH groups, sorbose-1-phosphate, polyphosphates, 6-deoxy-6-fluoroglucose, 2-C-hydroxy-methylglucose, xylose and lyxose (Sols et al., 1958, supra; McDonald, 1955, supra); further hexokinase inhibitors are disclosed in U.S. Pat. No. 5,854,067 entitled "Hexokinase Inhibitors." It will be understood that these inhibitors are listed for illustration only. Other Trx inhibitors exists and can be used, alone or in various combinations, in the methods of the present invention.

"Trx inhibitors" for use in the methods of the present invention also include reagents whereby the reduction of recombinantly produced antibodies or proteins may be reduced or prevented by decreasing the levels of enzymes of the Trx system, the pentose phosphate pathway or hexokinase at various points during the production campaign. In some embodiments, this reduction of enzyme levels may be accomplished by the use of targeted siRNAs, antisense nucleotides, or antibodies. To design targeted siRNAs or antisense nucleotides to the genes as found in CHO cells, these gene sequences are available from public databases to select sequences for targeting enzymes in different organisms. See Example 9 below for examples of the genes of the E. coli and mouse Trx system.

In addition to using inhibitors discussed above, it is also possible in certain embodiments of the instant invention to prevent the reduction of a recombinant protein to be purified by sparging the HCCF with air to maintain an oxidizing redox potential in the HCCF. This is a non-directed measure that can deplete glucose, G6P and NADPH by continuously oxidizing the reduced forms of Trx and TrxR. Air sparging of the HCCF tank can be performed, for example, with an air flow of about 100 liters to about 200 liters, such as, for example, 150 liters per minutes. Air sparging can be performed to reach an endpoint percentage of saturation; for example, air sparging can be continued until the HCCF is about 100% saturated with air, or it can be continued until the HCCR is about 30% saturated with air, or until it is between about 100% saturated to about 30% saturated with air. The minimum amount of dissolved oxygen ($dO_2$) required for the desired inhibitory effect also depends on the antibody or other recombinant protein produced. Thus, for example, about 10% $dO_2$ (or about 10 sccm for continuous stream) will have the desired effect during the production of antibody 2H7 (Variant A), while Apomab might require a higher (about 30%) $dO_2$.

In further embodiments of the instant invention, another non-directed method usable to block the reduction of the recombinant protein is lowering the pH of the HCCF. This embodiment takes advantage of particularly slow thiol-disulfide exchange at lower pH values (Whitesides et al., 1977, supra; Pleasants et al., 1989, supra). Therefore, the activity of the Trx system is significantly lower at pH values below 6, and thus the reduction of the recombinant protein, such as ocrelizumab, can be inhibited.

The non-directed approaches can also be combined with each other and/or with the use of one or more Trx inhibitors.

Disulfide bond reduction can be inhibited (i.e., partially or fully blocked) by using one or more Trx inhibitors and/or applying non-directed approaches following completion of the cell culture process, preferably to CCF prior to harvest or in the HCCF immediately after harvest. The optimal time and mode of application and effective amounts depend on the nature of the protein to be purified, the recombinant host cells, and the specific production method used. Determination of the optimal parameters is well within the skill of those of ordinary skill in the art.

For example, in a mammalian cell culture process, such as the CHO antibody production process described in the Examples herein, if cupric sulfate ($CuSO_4$ in the form of pentahydrate or the anhydrous form) is used as a Trx inhibitor, it can be added to supplement the CCF or HCCF in the concentration range of from about 5 μM to about 100 μM, such as from about 10 μM to about 80 μM, preferably from about 15 μM to about 50 μM. Since some cell cultures already contain copper (e.g. about 0.04 UM $CuSO_4$ for the CHO cell cultures used in the Examples herein), this amount is in addition to the copper, if any, already present in the cell culture. Any copper (II) salt can be used instead of $CuSO_4$ as long as solubility is not an issue. For example, copper acetate and copper chloride, which are both soluble in water, can be used instead of $CuSO_4$. The minimum effective concentration may also depend on the antibody produced and the stage where the inhibitor is used. Thus, for example, when cupric sulfate is added pre-lysis, for antibody 2H7

(Variant A) the minimum effective concentration is about 30 µM, for Apomab is about 75 µM, and for antibody Variant C (see Table 2) is about 50 µM. When cupric sulfate is added in CC medium, for antibody 2H7 (Variant A) the minimum effective concentration is about 15 µM, for Apomab is about 25 µM, and for antibody Variant C is about 20 µM. One typical minimal $CuSO_4$ inhibitor concentration of 2×Trx concentration (or Trx equivalence).

EDTA can be used in a wide concentration range, depending on the extent of cell lysis, the recombinant host cell used, and other parameters of the production process. For example, when using CHO or other mammalian host cells, EDTA can be typically added in a concentration of between about 5 mM to about 60 mM, such as from about 10 mM to about 50 mM, or from about 20 mM to about 40 mM, depending on the extent of cell lysis. For lower degree of cell lysis, lower concentrations of EDTA will suffice, while for a cell lysis of about 75%-100%, the required EDTA concentration is higher, such as, for example, from about 20 mM to about 40 mM. The minimum effective concentration may also depend on the antibody produced. Thus, for example, for antibody 2H7 (Variant A) the minimum effective EDTA concentration is about 10 mM.

DHEA as a Trx inhibitor is typically effective at a lower concentration, such as for example, in the concentration range from about 0.05 mM to about 5 mM, preferably from about 0.1 mM to about 2.5 mM.

Other Trx inhibitors, such as aurothioglucose (ATG) and aurothiomalate (ATM) inhibit reduction of disulfide bonds in the µM concentration range. Thus, for example, ATG or ATM may be added in a concentration between about 0.1 mM to about 1 mM. While the minimum inhibitory concentration varies depending on the actual conditions, for ATG and ATM typically it is around 4×TrxR concentration.

It is noted that all inhibitors can be used in an excess amount, therefore, it is not always necessary to know the amount of Trx or TrxR in the system.

In a preferred embodiment, the mammalian host cell used in the manufacturing process is a chinese hamster ovary (CHO) cell (Urlaub et al., *Proc. Natl. Acad. Sci. USA* 77:4216 (1980)). Other mammalian host cells include, without limitation, monkey kidney CV1 line transformed by SV40 (COS-7, ATCC CRL 1651); human embryonic kidney line (293 or 293 cells subcloned for growth in suspension culture), Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; a human hepatoma line (Hep G2); and myeloma or lymphoma cells (e.g. Y0, J558L, P3 and NS0 cells) (see U.S. Pat. No. 5,807,715).

A preferred host cell for the production of the polypeptides herein is the CHO cell line DP12 (CHO K1 dhfr). This is one of the best known CHO cell lines, widely used in laboratory practice (see, for example, EP 0,307,247, published Mar. 15, 1989). In addition, other CHO-K1 (dhfr⁻) cell lines are known and can be used in the methods of the present invention.

The mammalian host cells used to produce peptides, polypeptides and proteins can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM, Sigma) are suitable for culturing the host cells. In addition, any of the media described in Ham and Wallace (1979), Meth. in Enz. 58:44, Barnes and Sato (1980), Anal. Biochem. 102:255, U.S. Pat. Nos. 4,767,704; 4,657,866; 4,927,762; or 4,560,655; WO 90/03430; WO 87/00195; U.S. Pat. No. Re. 30,985; or 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

A protocol for the production, recovery and purification of recombinant antibodies in mammalian, such as CHO, cells may include the following steps: Cells may be cultured in a stirred tank bioreactor system and a fed batch culture, procedure is employed. In a preferred fed batch culture the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel).

Further, the cells of the culture may be propagated according to any scheme or routine that may be suitable for the particular host cell and the particular production plan contemplated. Therefore, a single step or multiple step culture procedure may be employed. In a single step culture the host cells are inoculated into a culture environment and the processes are employed during a single production phase of the cell culture. Alternatively, a multi-stage culture can be used. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

In certain embodiments, fed batch or continuous cell culture conditions may be devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., Na2CO$_3$ or NaOH). A suitable temperature range for culturing mammalian cells such as CHO cells is between about 30° C. to 38° C., and a suitable $dO_2$ is between 5-90% of air saturation.

At a particular stage the cells may be used to inoculate a production phase or step of the cell culture. Alternatively, as described above the production phase or step may be continuous with the inoculation or growth phase or step.

The cell culture environment during the production phase of the cell culture is typically controlled. Thus, if a glycoprotein is produced, factors affecting cell specific productivity of the mammalian host cell may be manipulated such that the desired sialic acid content is achieved in the resulting glycoprotein. In a preferred aspect, the production phase of the cell culture process is preceded by a transition phase of the cell culture in which parameters for the production phase of the cell culture are engaged. Further details of this process are found in U.S. Pat. No. 5,721,121, and Chaderjian et al., *Biotechnol. Prog.* 21(2):550-3 (2005), the entire disclosures of which are expressly incorporated by reference herein.

Following fermentation proteins are purified. Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins and components in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flowthrough." Thus, purification of recombinant proteins from the cell culture of mammalian host cells may include one or more affinity (e.g. protein A) and/or ion exchange chomarographic steps.

Ion exchange chromatography is a chromatographic technique that is commonly used for the purification of proteins. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). In the past, these changes have been progressive; i.e., the pH or conductivity is increased or decreased in a single direction.

For further details of the industrial purification of therapeutic antibodies see, for example, Fahrner et al., *Biotechnol. Genet. Eng. Rev.* 18:301-27 (2001), the entire disclosure of which is expressly incorporated by reference herein.

In addition to mammalian host cells, other eukaryotic organisms can be used as host cells for expression of the recombinant protein. For expression in yeast host cells, such as common baker's yeast or *Saccharomyces cerevisiae*, suitable vectors include episomally-replicating vectors based on the 2-micron plasmid, integration vectors, and yeast artificial chromosome (YAC) vectors. Other yeast suitable for recombinant production of heterologous proteins include *Schizosaccharomyces pombe* (Beach and Nurse, Nature, 290:140 (1981); EP 139,383 published 2 May 1985); *Kluyveromyces* hosts (U.S. Pat. No. 4,943,529; Fleer et al., Bio/Technology, 2:968 975 (1991)) such as, e.g., *K. lactis* (MW98-8C, CBS683, CBS4574; Louvencourt et al., J. Bacteriol., 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus*; *yarrowia* (EP 402,226); *Pichia pastoris* (EP 183,070; Sreckrishna et al., J. Basic Microbiol., 28:265 278 (1988)); *Candida*; *Trichoderma reesia* (EP 244,234); *Neurospora crassa* (Case et al., Proc. Natl. Acad. Sci. USA, 76:5259 5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284 289 (1983); Tilburn et al., Gene, 26:205 221 (1983); Yelton et al., Proc. Natl. Acad. Sci. USA, 81:1470 1474 (1984)) and *A. niger* (Kelly and Hynes, EMBO J., 4:475 479 (1985)). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982). Expression systems for the listed and other yeasts are well known in the art and/or are commercially available.

For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

The methods of the present invention also extend to cultures of prokaryotic host cells. Prokaryotic host cells suitable for expressing antibodies and other proteins to be protected by means of the instant invention include Archaebacteria and Eubacteria, such as Gram-negative or Grampositive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ (nmpc-fepE) degP41 kanR (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Methods for the production, recovery and purification of recombinant proteins from non-mammalian host cell cultures are also well known in the art. If the polypeptide is produced in a non-mammalian cell, e.g., a microorganism such as fungi or *E. coli*, the polypeptide will be recovered inside the cell or in the periplasmic space (Kipriyanov and Little, *Molecular Biotechnology*, 12:173 201 (1999); Skerra and Pluckthun, *Science*, 240:1038 1040 (1988)). Hence, it is necessary to release the protein from the cells to the extracellular medium by extraction such as cell lysis. Such disruption releases the entire contents of the cell into the homogenate, and in addition produces subcellular fragments that are difficult to remove due to their small size. These are generally removed by differential centrifugation or by filtration.

Cell lysis is typically accomplished using mechanical disruption techniques such as homogenization or head milling. While the protein of interest is generally effectively liberated, such techniques have several disadvantages (Engler, *Protein Purification Process Engineering*, Harrison eds., 37 55 (1994)). Temperature increases, which often occur during processing, may result in inactivation of the protein. Moreover, the resulting suspension contains a broad spectrum of contaminating proteins, nucleic acids, and polysaccharides. Nucleic acids and polysaccharides increase solution viscosity, potentially complicating subsequent processing by centrifugation, cross-flow filtration, or chromatography. Complex associations of these contaminants with the protein of interest can complicate the purification process and result in unacceptably low yields. Improved methods for purification of heterologous polypeptides from microbial fermentation broth or homogenate are described, for example, in U.S. Pat. No. 7,169,908, the entire disclosure of which is expressly incorporated herein by reference.

It is emphasized that the fermentation, recovery and purification methods described herein are only for illustration purposes. The methods of the present invention can be combined with any manufacturing process developed for the production, recovery and purification of recombinant proteins.

2. Antibodies

In a preferred embodiment, the methods of the present invention are used to prevent the reduction of inter- and/or intrachain disulfide bonds of antibodies, including therapeutic and diagnostic antibodies. Antibodies within the scope of the present invention include, but are not limited to: anti-HER2 antibodies including Trastuzumab (HERCEPTIN®) (Carter et al., *Proc. Natl. Acad. Sci. USA*, 89:4285-4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108B1, or Tositumomab (BEXXAR®); anti-IL-8 (St John et al., *Chest*, 103:932 (1993), and International Publication No. WO 95/23865); anti-VEGF antibodies including humanized and/or affinity matured anti-VEGF antibodies such as the humanized anti-VEGF antibody huA4.6.1 AVASTIN® (Kim et al., *Growth Factors*, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J. Immunol.* 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (Sec, U.S. Pat. No. 5,672,347 issued Sep. 30, 1997, Lorenz et al., *J. Immunol.* 156(4):1646-1653 (1996), and Dhainaut et al., *Crit. Care Med.* 23(9):1461-1469 (1995)); anti-Tissue Factor (TF) (European Patent No. 0 420 937 B1 granted Nov. 9, 1994); anti-human $α_4β_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al., *Arthritis Rheum* 39(1):52-56 (1996)); anti-CD52 antibodies such as CAMPATH-1H (Riechmann et al., *Nature* 332:323-337 (1988)); anti-Fc receptor antibodies such as the M22 antibody directed against FcγRI as in Graziano et al., *J. Immunol.* 155(10):4996-5002 (1995); anti-carcinoembryonic antigen (CEA) antibodies such as hMN-14 (Sharkey et al., *Cancer Res.* 55(23Suppl):5935s-5945s (1995); antibodies directed against breast epithelial cells including huBrE-3, hu-Mc 3 and CHL6 (Ceriani et al., *Cancer Res.* 55(23): 5852s-5856s (1995); and Richman et al., *Cancer Res.* 55(23 Supp): 5916s-5920s (1995)); antibodies that bind to colon carcinoma cells such as C242 (Litton et al., *Eur J. Immunol.* 26 (1): 1-9 (1996)); anti-CD38 antibodies, e.g. AT 13/5 (Ellis et al., *J. Immunol.* 155 (2): 925-937 (1995)); anti-CD33 antibodies such as Hu M195 (Jurcic et al., *Cancer Res* 55(23 Suppl): 5908s-5910s (1995) and CMA-676 or CDP771; anti-CD22 antibodies such as LL2 or LymphoCide (Juweid et al., *Cancer Res* 55(23 Suppl): 5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Many of these antibodies are widely used in clinical practice to treat various diseases, including cancer.

In certain specific embodiments, the methods of the present invention are used for the production of the following antibodies and recombinant proteins.

Anti-CD20 Antibodies

Rituximab (RITUXAN®) is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). Rituximab is indicated for the treatment of patients with relapsed or refractory low-grade or follicular, CD20-positive, B cell non-Hodgkin's lymphoma. In vitro mechanism of action studies have demonstrated that rituximab binds human complement and lyses lymphoid B cell lines through complement-dependent cytotoxicity (CDC) (Reff et al., *Blood* 83(2):435-445 (1994)). Additionally, it has significant activity in assays for antibody-dependent cellular cytotoxicity (ADCC). More recently, rituximab has been shown to have anti-proliferative effects in tritiated thymidine incorporation assays and to induce apoptosis directly, while other anti-CD19 and CD20 antibodies do not (Maloney et al., *Blood* 88(10):637a (1996)). Synergy between rituximab and chemotherapies and toxins has also been observed experimentally. In particular, rituximab. sensitizes drug-resistant human B cell lymphoma cell lines to the cytotoxic effects of doxorubicin, CDDP, VP-1 6, diphtheria toxin and ricin (Demidem et al., *Cancer Chemotherapy & Radiopharmaceuticals* 12 (3): 177-186 (1997)). In vivo preclinical studies have shown that rituximab depletes B cells from the peripheral blood, lymph nodes, and bone marrow of cynomolgus monkeys, presumably through complement and cell-mediated processes (Reff et al., *Blood* 83(2):435-445 (1994)).

Patents and patent publications concerning CD20 antibodies include U.S. Pat. Nos. 5,776,456, 5,736,137, 6,399,061, and 5,843,439, as well as U.S. patent application Nos. US 2002/0197255A1, US 2003/0021781A1, US 2003/0082172 A1, US 2003/0095963 A1, US 2003/0147885 A1 (Anderson et al.); U.S. Pat. No. 6,455,043B1 and WO00/09160 (Grillo-Lopez, A.); WO00/27428 (Grillo-Lopez and White); WO00/27433 (Grillo-Lopez and Leonard); WO00/44788 (Braslawsky et al.); WO01/10462 (Rastetter, W.); WO01/10461 (Rastetter and White); WO01/10460 (White and Grillo-Lopez); U.S. application No. US2002/0006404 and WO02/04021 (Hanna and Hariharan); U.S. application No. US2002/0012665 A1 and WO01/74388 (Hanna, N.); U.S. application No. US 2002/0058029 A1 (Hanna, N.); U.S. application No. US 2003/0103971 A1 (Hariharan and Hanna); U.S. application No. US2002/0009444A1, and WO01/80884 (Grillo-Lopez, A.); WO01/97858 (White, C.); U.S. application No. US2002/0128488A1 and WO02/34790 (Reff, M.); W)02/060955 (Braslawsky et al.); WO2/096948 (Braslawsky et al.); WO02/079255 (Reff and Davies); U.S. Pat. No. 6,171,586B1, and WO98/56418 (Lam et al.); WO98/58964 (Raju, S.); WO99/22764 (Raju, S.); WO99/51642, U.S. Pat. Nos. 6,194,551B1, 6,242,195B1, 6,528,624B1 and 6,538,124 (Idusogie et al.); WO00/42072 (Presta, L.); WO00/67796 (Curd et al.); WO01/03734 (Grillo-Lopez et al.); U.S. application No. US 2002/0004587A1 and WO01/77342 (Miller and Presta); U.S. application No. US2002/0197256 (Grewal, I.); U.S. application No. US 2003/0157108 A1 (Presta, L.); U.S. Pat. Nos. 6,090,365B1, 6,287,537B1, 6,015,542, 5,843,398, and 5,595,721, (Kaminski et al.); U.S. Pat. Nos. 5,500,362, 5,677,180, 5,721,108, and 6,120,767 (Robinson et al.); U.S. Pat. No. 6,410,391B1 (Raubitschek et al.); U.S. Pat. No. 6,224,866B1 and WO00/20864 (Barbera-Guillem, E.); WO01/13945 (Barbera-Guillem, E.); WO00/67795 (Goldenberg); U.S. application No. US 2003/01339301 A1 and WO00/74718 (Goldenberg and Hansen); WO00/76542 (Golay et al.); WO01/72333 (Wolin and Rosenblatt); U.S. Pat. No. 6,368,596B1 (Ghetie et al.); U.S. application No. US2002/0041847 A1, (Goldenberg, D.); U.S. application No. US2003/0026801A1 (Weiner and Hartmann); WO02/102312 (Engleman, E.); U.S. patent application No. 2003/0068664 (Albitar et al.); WO03/002607 (Leung, S.); WO 03/049694 and US 2003/0185796 A1 (Wolin et al.); WO03/061694 (Sing and Siegall); US 2003/0219818 A1 (Bohen et al.); US 2003/0219433 A1 and WO 03/068821 (Hansen et al.) each of which is expressly incorporated herein by reference. See, also, U.S. Pat. No. 5,849,898 and EP application no. 330,191 (Seed et al.); U.S. Pat. No. 4,861,579 and EP332,865A2 (Meyer and Weiss); U.S. Pat. No. 4,861,579 (Meyer et al.) and WO95/03770 (Bhat et al.).

Publications concerning therapy with Rituximab include: Perotta and Abuel "Response of chronic relapsing ITP of 10 years duration to Rituximab" Abstract #3360 *Blood* 10(1) (part 1-2): p. 88B (1998); Stashi et al., "Rituximab chimeric anti-CD20 monoclonal antibody treatment for adults with chronic idopathic thrombocytopeniaurpura" *Blood* 98(4): 952-957 (2001); Matthews, R. "Medical Heretics" New Scientist (7 Apr. 2001); Leandro et al., "Clinical outcome in 22 patients with rheumatoid arthritis treated with B lymphocyte depletion" *Ann Rheum Dis* 61:833-888 (2002); Leandro et al., "Lymphocyte depletion in rheumatoid arthritis: early evidence for safety, efficacy and dose response. *Arthritis & Rheumatism* 44(9): S370 (2001); Leandro et al., "An open study of B lymphocyte depletion in systemic lupus erythematosus", *Arthritis & Rheumatism* 46(1):2673-2677 (2002); Edwards and Cambridge "Sustained improvement in rheumatoid arthritis following a protocol designed to deplete B lymphocytes" *Rheumatology* 40:205-211 (2001); Edwards et al., "B-lymphocyte depletion therapy in rheumatoid arthritis and other autoimmune disorders" *Biochem. Soc. Trans.* 30(4):824-828 (2002); Edwards et al., "Efficacy and safety of Rituximab, a B-cell targeted chimeric monoclonal antibody: A randomized, placebo controlled trial in patients with rheumatoid arthritis. *Arthritis & Rheumatism* 46(9): S197 (2002); Levine and Pestronk "IgM antibody-related polyneuropathies: B-cell depletion chemotherapy using Rituximab" *Neurology* 52:1701-1704 (1999); De Vita et al., "Efficacy of selective B cell blockade in the treatment of rheumatoid arthritis" *Arthritis & Rheumatism* 46:2029-2033 (2002); Hidashida et al., "Treatment of DMARD-Refractory rheumatoid arthritis with rituximab." Presented at the Annual Scientific Meeting of the American College of *Rheumatology*; October 24-29; New Orleans, La. 2002; Tuscano, J. "Successful treatment of Infliximab-refractory rheumatoid arthritis with rituximab" Presented at the Annual Scientific Meeting of the American College of *Rheumatology*; October 24-29; New Orleans, La. 2002. Sarwal et al., *N. Eng. J. Med.* 349(2):125-138 (Jul. 10, 2003) reports molecular heterogeneity in acute renal allograft rejection identified by DNA microarray profiling.

In various embodiments, the invention provides pharmaceutical compositions comprising humanized 2H7 anti-CD20 antibodies. In specific embodiments, the humanized 2H7 antibody is an antibody listed in Table 2.

TABLE 2

Humanized anti-CD20 Antibody and Variants Thereof

| 2H7 variant | $V_L$ SEQ ID NO. | $V_H$ SEQ ID NO. | Full L chain SEQ ID NO. | Full H chain SEQ ID NO. |
|---|---|---|---|---|
| A | 1 | 2 | 6 | 7 |
| B | 1 | 2 | 6 | 8 |
| C | 3 | 4 | 9 | 10 |
| D | 3 | 4 | 9 | 11 |
| F | 3 | 4 | 9 | 12 |
| G | 3 | 4 | 9 | 13 |
| H | 3 | 5 | 9 | 14 |
| I | 1 | 2 | 6 | 15 |

Each of the antibody variants A, B and I of Table 2 comprises the light chain variable sequence ($V_L$):

(SEQ ID NO: 1)
DIQMTQSPSSLSASVGDRVTITCRASSSVSYMHWYQQKPGKAPKPLIYA

PSNLASGVPSRFSGSGSGTDFTLTISSLQPEDFATYYCQQWSFNPPTFG

QGTKVEIKR;

and
the heavy chain variable sequence ($V_H$):

(SEQ ID NO: 2)
EVQLVESGGGLVQPGGSLRLSCAASGYTFTSYNMHWVRQAPGKGLEWVG

AIYPGNGDTSYNQKFKGRFTISVDKSKNTLYLQMNSLRAEDTAVYYCAR

VVYYSNSYWYFDVWGQGTLVTVSS.

Each of the antibody variants C, D, F and G of Table 2 comprises the light chain variable sequence ($V_L$):

(SEQ ID NO: 3)
DIQMTQSPSSLSASVGDRVTITCRASSSVSYLHWYQQKPGKAPKPLIYA

PSNLASGVPSRFSGSGSGTDFTLTISSLQPEDFATYYCQQWAFNPPTFG

QGTKVEIKR, and
the heavy chain variable sequence ($V_H$):

(SEQ ID NO: 4)
EVQLVESGGGLVQPGGSLRLSCAASGYTFTSYNMHWVRQAPGKGLEWVG

ATYPGNGATSYNQKFKGRFTISVDKSKNTLYLQMNSLRAEDTAVYYCAR

VVYYSASYWYFDVWGQGTLVTVSS.

The antibody variant H of Table 2 comprises the light chain variable sequence ($V_L$) of SEQ ID NO:3 (above) and the heavy chain variable sequence ($V_H$):

(SEQ ID NO: 5)
EVQLVESGGGLVQPGGSLRLSCAASGYTFTSYNMHWVRQAPGKGLEWVG

ATYPGNGATSYNQKFKGRFTISVDKSKNTLYLQMNSLRAEDTAVYYCAR

VVYYSYRYWYFDVWGQGTLVTVSS

Each of the antibody variants A, B and I of Table 2 comprises the full length light chain sequence:

(SEQ ID NO: 6)
DIQMTQSPSSLSASVGDRVTITCRASSSVSYMHWYQQKPGKAPKPLIYA

PSNLASGVPSRFSGSGSGTDFTLTISSLQPEDFATYYCQQWSFNPPTFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC.

Variant A of Table 2 comprises the full length heavy chain sequence:

(SEQ ID NO: 7)
EVQLVESGGGLVQPGGSLRLSCAASGYTFTSYNMHWVRQAPGKGLEWVG
AIYPGNGDTSYNQKFKGRFTISVDKSKNTLYLQMNSLRAEDTAVYYCAR
VVYYSNSYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK.

Variant B of Table 2 comprises the full length
heavy chain sequence:
(SEQ ID NO: 8)
EVQLVESGGGLVQPGGSLRLSCAASGYTFTSYNMHWVRQAPGKGLEWVG
AIYPGNGDTSYNQKFKGRFTISVDKSKNTLYLQMNSLRAEDTAVYYCAR
VVYYSNSYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNATYRVVSVLTVLHQDWLNGKEYKCKVSNKALPAPIAATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK.

Variant I of Table 2 comprises the full length
heavy chain sequence:
(SEQ ID NO: 15)
EVQLVESGGGLVQPGGSLRLSCAASGYTFTSYNMHWVRQAPGKGLEWVG
AIYPGNGDTSYNQKFKGRFTISVDKSKNTLYLQMNSLRAEDTAVYYCAR
VVYYSNSYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNATYRVVSVLTVLHQDWLNGKEYKCKVSNAALPAPIAATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK.

Each of the antibody variants C. D. F. G and H of Table 2 comprises the full length light chain sequence:

(SEQ ID NO: 9)
DIQMTQSPSSLSASVGDRVTITCRASSSVSYLHWYQQKPGKAPKPLIYA
PSNLASGVPSRFSGSGSGTDFILTISSLQPEDFATYYCQQWAFNPPTFG
QGTKVEIKRTVAAPSVFIFPPSDEQLKSGTASVVCLLNNFYPREAKVQW

-continued
KVDNALQSGNSQESVTEQDSKDSTYSLSSTLTLSKADYEKHKVYACEVT
HQGLSSPVTKSFNRGEC.

Variant C of Table 2 comprises the full length
heavy chain sequence:
(SEQ ID NO: 10)
EVQLVESGGGLVQPGGSLRLSCAASGYTFTSYNMHWVRQAPGKGLEWVG
AIYPGNGATSYNQKFKGRFTISVDKSKNTLYLQMNSLRAEDTAVYYCAR
VVYYSASYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNATYRVVSVLTVLHQDWLNGKEYKCKVSNKALPAPIAATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK.

Variant D of Table 2 comprises the full length
heavy chain sequence:
(SEQ ID NO: 11)
EVQLVESGGGLVQPGGSLRLSCAASGYTFTSYNMHWVRQAPGKGLEWVG
AIYPGNGATSYNQKFKGRFTISVDKSKNTLYLQMNSLRAEDTAVYYCAR
VVYYSASYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRIPEVTCVVVDVSHEDPEVKFNWYVDGVEVHNAKT
KPREEQYNATYRVVSVLTVLHQDWLNGKEYKCAVSNKALPAPIEATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK.

Variant F of Table 2 comprises the full length
heavy chain sequence:
(SEQ ID NO: 12)
EVQLVESGGGLVQPGGSLRLSCAASGYTFTSYNMHWVRQAPGKGLEWVG
AIYPGNGATSYNQKFKGRFTISVDKSKNTLYLQMNSLRAEDTAVYYCAR
VVYYSASYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNATYRVVSVLTVLHQDWLNGKEYKCKVSNAALPAPIAATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYT
QKSLSLSPGK.

Variant G of Table 2 comprises the full length
heavy chain sequence:
(SEQ ID NO: 13)
EVQLVESGGGLVQPGGSLRLSCAASGYTFTSYNMHWVRQAPGKGLEWVG
AIYPGNGATSYNQKFKGRFTISVDKSKNTLYLQMNSLRAEDTAVYYCAR
VVYYSASYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNATYRVVSVLIVLHQDWLNGKEYKCKVSNAALPAPIAATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHWHY
TQKSLSLSPGK.

Variant H of Table 2 comprises the full length
heavy chain sequence:
(SEQ ID NO: 14)
EVQLVESGGGLVQPGGSLRLSCAASGYTFTSYNMHWVRQAPGKGLEWVG
AIYPGNGATSYNQKFKGRFTISVDKSKNTLYLQMNSLRAEDTAVYYCAR
VVYYSYRYWYFDVWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKT
KPREEQYNATYRVVSVLTVLHQDWLNGKEYKCKVSNAALPAPIAATISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK.

In certain embodiments, the humanized 2H7 antibody of the invention further comprises amino acid alterations in the IgG Fc and exhibits increased binding affinity for human FcRn over an antibody having wild-type IgG Fc, by at least 60 fold, at least 70 fold, at least 80 fold, more preferably at least 100 fold, preferably at least 125 fold, even more preferably at least 150 fold to about 170 fold.

The N-glycosylation site in IgG is at Asn297 in the $C_H2$ domain. Humanized 2H7 antibody compositions of the present invention include compositions of any of the preceding humanized 2H7 antibodies having a Fc region, wherein about 80-100% (and preferably about 90-99%) of the antibody in the composition comprises a mature core carbohydrate structure which lacks fucose, attached to the Fc region of the glycoprotein. Such compositions were demonstrated herein to exhibit a surprising improvement in binding to Fc(RIIIA (F158), which is not as effective as Fc(RIIIA (V158) in interacting with human IgG. Fc(RIIIA (F158) is more common than Fc(RIIIA (V158) in normal, healthy African Americans and Caucasians. See Lehrnbecher et al., *Blood* 94:4220 (1999). Historically, antibodies produced in Chinese Hamster Ovary Cells (CHO), one of the most commonly used industrial hosts, contain about 2 to 6% in the population that are nonfucosylated. YB2/0 and Lee 13, however, can produce antibodies with 78 to 98% nonfucosylated species. Shinkawa et al., *J Bio. Chem.* 278 (5), 3466-347 (2003), reported that antibodies produced in YB2/0 and Lec13 cells, which have less FUT8 activity, show significantly increased ADCC activity in vitro. The production of antibodies with reduced fucose content are also described in e.g., Li et al., (GlycoFi) "Optimization of humanized IgGs in glycoengineered *Pichia pastoris*" in Nature Biology online publication 22 Jan. 2006; Niwa R. et al., *Cancer Res.* 64(6):2127-2133 (2004); US 2003/0157108 (Presta); U.S. Pat. No. 6,602,684 and US 2003/0175884 (Glycart Biotechnology); US 2004/0093621, US 2004/0110704, US 2004/0132140 (all of Kyowa Hakko Kogyo).

A bispecific humanized 2H7 antibody encompasses an antibody wherein one arm of the antibody has at least the antigen binding region of the H and/or L chain of a humanized 2H7 antibody of the invention, and the other arm has V region binding specificity for a second antigen. In specific embodiments, the second antigen is selected from the group consisting of CD3, CD64, CD32A, CD16, NKG2D or other NK activating ligands.

Anti-HER2 Antibodies

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration (FDA) Sep. 25, 1998 for the treatment of patients with metastatic breast cancer whose tumors overexpress the HER2 protein. In November 2006, the FDA approved Herceptin as part of a treatment regimen containing doxorubicin, cyclophosphamide and paclitaxel, for the adjuvant treatment of patients with HER2-positive, node-positive breast cancer.

In one embodiment, the anti-HER2 antibody comprises the following $V_L$ and $V_H$ domain sequences:

humanized 2C4 version 574 antibody $V_L$ (SEQ ID NO: 16)
DIQMTQSYSSLSASVGDRVTITCKASQDVSICVAWYQQKPGKAPKLLIYS

ASYRYTGVPSRFSGSGSGTDFTLTISSLQPEDFATYYCQQYYIYPYTFGQ

GTKVEIK.

and humanized 2C4 version 574 antibody V$_H$ (SEQ ID NO: 17)
EVQLVESGGGLVQPGGSLRLSCAASGFTFTDYTMDWVRQAPGKGLEWVAD

VNPNSGGSIYNQRFKGRFTLSVDRSKNTLYLQMNSLRAEDTAVYYCARNL

GPSFYFDYWGQGTLVTVSS

In another embodiment, the anti-HER2 antibody comprises the V$_L$ (SEQ ID NO:18) and V$_H$ (SEQ ID NO:19) domain sequences of trastuzumab as shown in FIG. 21 and FIG. 22, respectively.

Other HER2 antibodies with various properties have been described in Tagliabue et al., *Int. J. Cancer* 47:933-937 (1991); Mckenzie et al., *Oncogene* 4:543-548 (1989); Maier et al., *Cancer Res.* 51:5361-5369 (1991); Bacus et al., *Molecular Carcinogenesis* 3:350-362 (1990); Stancovski et al., *PNAS* (USA) 88:8691-8695 (1991); Bacus et al., *Cancer Research* 52:2580-2589 (1992); Xu et al., *Int. J. Cancer* 53:401-408 (1993); WO94/00136; Kasprzyk et al., *Cancer Research* 52:2771-2776 (1992); Hancock et al., *Cancer Res.* 51:4575-4580 (1991); Shawver et al., *Cancer Res.* 54:1367-1373 (1994); Arteaga et al., *Cancer Res.* 54:3758-3765 (1994); Harwerth et al., *J. Biol. Chem.* 267:15160-15167 (1992); U.S. Pat. No. 5,783,186; and Klapper et al., *Oncogene* 14:2099-2109 (1997).

Anti-VEGF Antibodies

The anti-VEGF antibodies may, for example, comprise the following sequences:

In one embodiment, the anti-VEGF antibody comprises the following V$_L$ sequence (SEQ ID NO: 20):
DIQMTQTTSS LSASLGDRVI ISCSASQDIS NYLNWYQQKP

DGTVKVLIYF TSSLHSGVPS RFSGSGSGTD YSLTISNLEP

EDIATYYCQQ YSTVPWTFGG GTKLEIKR;
and the following V$_H$ sequence (SEQ ID NO: 21):
EIQLVQSGPE LKQPGETVRI SCKASGYTFT NYGMNWVKQA

PGKGLKWMGW INTYTGEPTY AADFKRRFTF SLETSASTAY

LQISNLKNDD TATYFCAKYP HYYGSSHWYF DVWGAGTTVT VSS.

In another embodiment, the anti-VEGF antibody comprises the following V$_L$ sequence (SEQ ID NO: 22):
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR;
and the following V$_H$ sequence (SEQ ID NO: 23):
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT VSS.

In a third embodiment, the anti-VEGF antibody comprises the following V$_L$ sequence (SEQ ID NO: 24):
DIQLTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR;

and the following V$_H$ sequence (SEQ ID NO: 25):
EVQLVESGGG LVQPGGSLRL SCAASGYDFT HYGMNWVRQA

PGKGLEWVGW INTYTGEPTY AADFKRRFTF SLDTSKSTAY

LQMNSLRAED TAVYYCAKYP YYYGTSHWYF DVWGQGTLVT VSS.

Anti-CD11a Antibodies

The humanized anti-CD11a antibody efalizumab or Raptiva® (U.S. Pat. No. 6,037,454) received marketing approval from the Food and Drug Administration on Oct. 27, 2003 for the treatment for the treatment of psoriasis. One embodiment provides for an anti-human CD11a antibody comprising the V$_L$ and V$_H$ sequences of HuMHM24 below:

V$_L$ (SEQ ID NO: 26):
DIQMTQSPSSLSASVGDRVTITCRASKTISKYLAWYQQKPGKAPKLLIY
SGSTLQSGVPSRFSGSGSGTDFTLTISSLQPEDFATYYCQQHNEYPLTF
GQGTKVEIKR; and V$_H$ (SEQ ID NO: 27):
EVQLVESGGGLVQPGGSLRLSCAASGYSFTGHWMNWVRQAPGKGLEWVG
MIHPSDSETRYNQKFKDRFTISVDKSKNTLYLQMNSLRAEDTAVYYCAR
GIYFYGTTYFDYWGQGTLVTVSS.

The anti-human CD11a antibody may comprise the V$_H$ of SEQ ID NO:27 and the full length L chain of HuMHM24 having the sequence of:
(SEQ ID NO: 28)
DIQMTQSPSSLSASVGDRVTITCRASKTISKYLAWYQQKPGKAPKLLIY
SGSTLQSGVPSRFSGSGSGTDFTLTISSLQPEDFATYYCQQHNEYPLTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC, or the L chain above with the H chain having the sequence of:
(SEQ ID NO: 29)
EVQLVESGGGLVQPGGSLRLSCAASGYSFTGHWMNWVRQAPGKGLEWVG
MIHPSDSETRYNQKFKDRFTISVDKSKNTLYLQMNSLRAEDTAVYYCAR
GIYFYGTTYFDYWGQGTLVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYT
QKSLSLSPGK.

Antibodies to the DR5 receptor (anti-DR5) antibodies can also be produced in accordance with the present invention. Such anti-DR5 antibodies specifically include all antibody variants disclosed in PCT Publication No. WO 2006/083971, such as the anti-DR5 antibodies designated Apomabs 1.1, 2.1, 3.1, 4.1, 5.1, 5.2, 5.3, 6.1, 6.2, 6.3, 7.1, 7.2, 7.3, 8.1, 8.3, 9.1, 1.2, 2.2, 3.2, 4.2, 5.2, 6.2, 7.2, 8.2, 9.2, 1.3, 2.2, 3.3, 4.3, 5.3, 6.3, 7.3, 8.3, 9.3, and 25.3, especially Apomab 8.3 and Apomab 7.3, preferably Apomab 7.3. The entire content of WO 2006/083971 is hereby expressly incorporated by reference.

3. Other Disulfide-Containing Proteins

In addition to antibodies, the methods of the present invention find utility in the manufacturing of other polypeptides including disulfide bonds. Representative examples of such polypeptides include, without limitation, the following therapeutic proteins: tissue plasminogen activators (t-PAs), such as human tissue plasminogen activator (htPA, alteplase, ACTIVASE®), a thrombolytic agent for the treatment of myocardial infarction; a TNKase™, a ht-PA variant with extended half-life and fibrin specificity for single-bolus administration; recombinant human growth hormone (rhGH, somatropin, NUTROPIN®, PROTROPIN®) for the treatment of growth hormone deficiency in children and adults; and recombinant human deoxyribonuclease I (DNase I) for the treatment of cystic fibrosis (CF).

Examples of disulfide-containing biologically important proteins include growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

4. General Methods for the Recombinant Production of Antibodies

The antibodies and other recombinant proteins herein can be produced by well known techniques of recombinant DNA technology. Thus, aside from the antibodies specifically identified above, the skilled practitioner could generate antibodies directed against an antigen of interest, e.g., using the techniques described below.

Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22, CD34, CD40; members of the ErbB receptor family such as the EGF receptor, HER2, HER3 or HER4 receptor; cell adhesion molecules such as LFA-1, Mac1, p150,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein. Antigens to which the antibodies listed above bind are specifically included within the scope herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, malcimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro.

Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, California USA, and SP-2 or X63-Ag8-653 cells available from the American Type Culture Collection, Rockville, Maryland USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional hybridoma techniques for isolation of monoclonal antibodies.

Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., Nature, 362:255-258 (1993); Bruggermann et al., *Year in Immuno.*, 7:33 (1993); and Duchosal et al., Nature 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al., *Nature Biotech* 14:309 (1996)).

Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv) (see WO 93/16185).

Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$.) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al., *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al., *J. Immunol.* 147:60 (1991).

Immunoadhesins

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ (Ig$G_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

$AC_L$-$AC_L$;

$AC_H$-($AC_H$,$AC_L$-$AC_H$,$AC_L$-$V_H C_H$, or $V_L C_L$-$AC_H$);

$AC_L$-$AC_H$-($AC_L$-$AC_H$,$AC_L$-$V_H C_H$,$V_L C_L$-$AC_H$, or $V_L C_L$-$V_H C_H$) $AC_L$-$V_H C_H$-($AC_H$, or $AC_L$-$V_H C_H$, or $V_L C_L$-$AC_H$);

$V_L C_L$-$AC_H$-($AC_L$-$V_H C_H$, or $V_L C_L$-$AC_H$); and $(A$-$Y)_n$-$(V_L C_L$-$V_H C_H)_2$, wherein each A represents identical or different adhesin amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Virginia.

Example 1

Description of Materials and Methods

The following materials and methods were used in Examples 2-8 below.
Materials
Materials and devices used in the experiments described in the experimental examples include: stainless steel vials (mini-tanks, Flow Components, Dublin, CA; short (50 cc) and tall (55 cc)); dialysis tubing (Spectra/Por, 6-8000 MWCO, cat. #132645), 0.22 µm filter (Millipore Millipak Gamma Gold cat. #MPGL04GH2); phosphate buffered saline (PBS, EMD, cat. #6506); ethylenediaminetetraacetic acid (EDTA, Sigma, cat. #E4884); α-nicotinamide adenine dinucleotide phosphate (NADPH, Calbiochem, cat. #481973); dehydroepiandrosterone (DHEA, TCI, cat. #D0044); cupric sulfate (Sigma, cat. #C8027), glucose-6-phosphate (G6P, Calbiochem, cat. #346764); aurothioglucose (ATG, USP, cat. #1045508); aurothiomalate (ATM, Alfa Aesar, cat. #39740); reduced glutathione (GSH, J. T. Baker, cat. #M770-01); monobromobimane (mBB, Fluka, cat. #69898); histidine (J. T. Baker, cat. #2080-05); sodium sulfate (J. T. Baker, cat. #3897-05); Trx (Sigma, cat. #T8690); TrxR (Sigma, cat. #T9698). All chemicals and reagents were used as received with no further purification. Stock solutions of EDTA (250 mM, pH 7.5), $CuSO_4$ (10 mM), ATG (30 mM), ATM (30 mM), NADPH (75 mM), G6P (300 mM) were prepared for use in the mini-tank time course studies.
Generation of Cell Culture Fluid (CCF)
In order to generate ocrelizumab CCF for the various reduction studies, a representative small-scale fermentation process was utilized similar to the methods described previously (Chaderjian et al., 2005). Briefly, 3 liter glass stirred-tank Applikon® bioreactors fitted with pitched blade impellers were used for the inoculum-train and production cultures with the ocrelizumab media components. The bioreactors were outfitted with calibrated dissolved oxygen (DO), pH and temperature probes. DO, pH, temperature, and agitation rate were controlled using digital control units to the defined parameters of the ocrelizumab manufacturing process. The working volume for both the inoculum-train and production cultures was 1.5 L. Daily samples were analyzed on a NOVA Bioprofile blood gas analyzer to ensure the accuracy of the on-line value for pH and dissolved oxygen as well as to monitor the glucose, lactate, ammonium, glutamine, glutamate, and sodium concentrations in the cultures. Daily samples were also taken to monitor cell growth, viability, and titer. Cell growth was measured both by viable cell counts using a ViCell as well as on a packed cell volume (PCV) basis. Culture viability was determined by trypan blue exclusion on a ViCell instrument. Supernatant samples were assayed by an HPLC-based method to measure ocrelizumab titer values.
Harvested Cell Culture Fluid (HCCF) Preparation
Complete lysis of CCF was achieved by high pressure homogenization using a Microfluidics HC-8000 homogenizer. The pressure regulator of the instrument was set to 4,000-8,000 psi, and the CCF was pulled in through the homogenizer to obtain complete cell lysis (membrane breakage) after a single pass. The CCF homogenate was collected once water was purged through the system. The homogenate was transferred to centrifuge bottles and centrifuged in a Sorval RC-3B rotor centrifuge at 4,500 rpm for 30 minutes at 20° C. The centrate was decanted and then depth filtered followed by 0.22 m sterile filtration using a peristaltic pump with silicon tubing to generate the final HCCF from the homogenized CCF (100% cell lysis). Alternatively, the CCF was centrifuged straight from the fermentor without any homogenization and then the centrate was filtered with a sterile 0.22 m filter to generate the HCCF.
Mini-Tank Handling
A laminar flow hood was used in handling all mini-tanks and all materials used in the HCCF incubation experiments were either autoclaved or rinsed using 70% isopropanol to minimize bacterial contamination.
Lactate Dehydrogenase Assay
For lactate dehydrogenase assay, see Babson & Babson (1973) and Legrand et al., (1992), which are hereby incorporated by reference.
Dialysis Experiment
A dialysis experiment was carried out in order to determine whether the components causing reduction of ocrelizumab were small molecules or macromolecules (i.e. enzymes). A sample of 3 mL of purified and formulated ocrelizumab (30.2 mg/mL) was dialyzed against 1 L of phosphate buffered saline (PBS, 10 mM pH 7.2) for 24 hours and the PBS was changed after 8 hours. The concentration of the ocrelizumab sample was then adjusted to 1 mg/ml using the absorbance at 280 nm. Aliquots were stored at −70° C. prior to use. Dialysis tubing was hydrated overnight in a 0.05% azide solution and rinsed with sterile water prior to use. The HCCF obtained from homogenization of CCF from a 3-L fermentor was thawed and filtered through a 0.22 µm Millipak filter using a peristaltic pump. Six short mini-tanks were filled with 30 mL of HCCF each. To each mini-tank, 500 µL of ocrelizumab sample in sealed dialysis tubing was added. The mini-tanks were sealed and loaded into a bench top mixer (Barnstead Lab-Line MAX Q 4000) operating at 35 rpm and ambient temperature. For each time-point, one mini-tank was removed from the mixer, and aliquots of the HCCF (in the mini-tank) and ocrelizumab sample (in the dialysis bag) were taken and stored at −70° C. until analyzed with the free thiol assay and the Bioanalyzer assay (described below).
Test Inhibitors for Reduction in a Small-Scale In Vitro System
A tall mini-tank was filled with 27 mL of HCCF. Depending on the experiment design, various reagents (NADPH, G6P, inhibitors of G6PD or TrxR) were added to the desired concentration, and the final volume in the mini-tank was brought to 30 mL with PBS (10 mM pH 7.2). The mini-tanks were sealed and loaded into a bench top mixer running at 35 rpm and ambient temperature. At each-time point for sampling, the exteriors of the mini-tanks were sterilized with 70% IPA and opened in a laminar flow hood for the removal of an aliquot. The mini-tanks were then re-sealed and loaded back into the bench top mixer. All aliquots were stored at −70° C. until analyzed with the free thiol assay and Bioanalyzer assay (described below).

In Vitro Trx/TrxRreductase Studies

A commercial TrxR (rat liver) solution (4 µM) was diluted with water to yield a 2.86 µM solution. Lyophilized Trx (human) was reconstituted with PBS (10 mM, pH 7.2) yielding a 500 µM solution. A solution of 20 mM NADPH and 10 mM ATG and ATM solutions were prepared in water.

In a black polypropylene 1.5 mL micro centrifuge tube, 437 µL PBS, 25 L NADPH, 16 µL formulated ocrelizumab solution (30.2 mg/mL) and 5 µL Trx were gently mixed. The reaction was initiated by the addition of 17.5 µL TrxR. The reaction was incubated at room temperature for 24 hours. Aliquots of 20 µL were taken at each sampling time-point and stored at −70° C. until analyzed by the Bioanalyzer assay (see below). Controls were performed to determine if the enzymatic pathway was active when an enzyme was omitted by substituting an equal volume of PBS for either Trx and/or TrxR in the reaction mixture.

Inhibition of the Trx system was demonstrated using the same reaction conditions described above with the addition of 5 µL ATG or ATM. To demonstrate the inhibition of Trx system by $Cu^{2+}$, 2.5 µL of $CuSO_4$ (10 mM) was added to reaction mixture using the same enzymes but a different buffer (10 mM histidine, 10 mM $Na_2SO_4$, 137 mM NaCl, 2.5 mM KCl, pH 7.0) to prevent formation of insoluble $Cu_3(PO_4)_2$.

Free Thiol Assay

A standard curve using GSH was generated in PBS (10 mM, pH 6.0±0.05). From a 110 mM GSH solution, standards were prepared at concentrations of 0, 5.5, 11, 22, 44, 55, 110 and 550 µM through serial dilution. From an acetonitrile stock solution of mBB (10 mM stored at −20° C.), a 100 µM solution of mBB was prepared in PBS (10 mM, pH 10.0±0.05) and stored away from light.

In a black, flat bottomed 96 well plate, 100 µL of mBB was dispensed into each well. For the standard curve, 10 µL of standard GSH solution was added yielding a working pH of 8.0±0.2. For samples, 10 µL of sample was added to the wells. All wells were prepared in triplicate. The plate was incubated at room temperature for 1 hour in the dark then read using a fluorescence plate reader (Molecular Devices SpectraMax® Gemini XS) with an excitation wavelength of 390 nm and an emission wavelength of 490 nm. A linear standard curve was generated using the average result of the three standard wells plotted versus GSH concentration. Free thiol levels in samples were calculated from the linear equation of the standard curve using the average value of the three sample wells.

Bioanalyzer Assay

Capillary electrophoresis measurements were acquired using the Agilent 2100 Bioanalyzer. Sample preparation was carried out as described in the Agilent Protein 230 Assay Protocol (manual part number G2938-90052) with minor changes. HCCF samples were diluted, 1:4 and Protein A samples were diluted to 1.0 g/L with water prior to preparation. For HCCF samples at the denaturing step, 24 µL of a 50 mM iodoacetamide (IAM), 0.5% SDS solution was added in addition to the 2 µL of denaturing solution provided. For Protein A samples, 0.5% SDS with no IAM and 2 µL of denaturing solution were used. Digital gel-like images were generated using Agilent 2100 Expert software.

Stock Solutions for HCCF Hold Time Studies

Three separate stock solutions were used in the lab scale HCCF hold time studies: (1) 250 mM stock solution of EDTA (pH 7.4) prepared using EDTA, disodium dihydrate (Mallinckrodt, cat. #7727-06 or Sigma, cat. #E-5134) and EDTA, tetrasodium dihydrate (Sigma, cat. #E-6511), (2) 50 mM stock solution of cupric sulfate pentahydrate ($CuSO_4$, Sigma, cat. #C-8027), and (3) 1 M acetic acid solution (Mallinckrodt, cat. #V193).

Inhibitor Additions and Cell Culture Fluid (CCF) Blending

A stock solution of either 250 mM EDTA or 50 mM $CuSO_4$ was added to the CCF prior to homogenization to evaluate a range of final concentrations to prevent antibody disulfide reduction. Once the final HCCF was generated from the homogenized CCF, these solutions were then mixed with the HCCF generated from the non-homogenized CCF (also containing EDTA or $CuSO_4$) in order to dilute and decrease the total level of cell lysis to below the 100% maximum. Alternatively, a stock solution of 1 M acetic acid was added to a final blended HCCF solution (homogenized CCF and non-homogenized CCF) to decrease the pH of the solution to prevent antibody disulfide reduction.

Approximately 30-50 mL of each HCCF solution (containing EDTA, $CuSO_4$, acetic acid, or no addition for the control) was held in a 50 mL 316L stainless steel vial. The vial was sealed with a clamp, and the solution was not aerated or agitated. The vial was stored at room temperature (18-22° C.). At pre-determined time points, the solution was removed and purified over a lab scale protein A affinity resin.

Similar results can be obtained with other oxidizing agents, such as, for example, cystine and oxidized glutathione.

Air Sparging

To evaluate air sparging of the HCCF generated from homogenized CCF to prevent antibody disulfide reduction, 3-L glass or 15-L stainless steel vessels were utilized. Approximately 1-5 L of HCCF was 0.22□m sterile filtered into each sterilized vessel. Experimental conditions were maintained at 18-22° C. and 50 (15-L fermentor) or 275 rpm (3-L fermentor) agitation either with or without pH control by the addition of carbon dioxide. Solutions were either sparged with air to increase the dissolved oxygen level to air saturation or with nitrogen (control) to remove any dissolved oxygen in solution. Gas flow to each vessel was variable dependent upon whether a constant aeration rate was used or a minimum level of dissolved oxygen was maintained. At pre-determined time points, 25-50 mL samples were removed from both vessels and purified over a lab scale protein A affinity resin prior to analysis.

Protein A Processing

Antibody in harvested cell culture fluid samples can be captured and purified using a specific affinity chromatography resin. Protein A resin (Millipore, Prosep-vA High Capacity) was selected as the affinity resin for antibody purification. The resin was packed in a 0.66 cm inner diameter glass column (Omnifit®) with a 14 cm bed height resulting in a 4.8 mL final column volume. Chromatography was performed using an AKTA Explorer 100 chromatography system (GE Healthcare).

The resin was exposed to buffers and HCCF at a linear flow rate between 350-560 cm/hr. The resin was equilibrated with 25 mM Tris, 25 mM NaCl, 5 mM EDTA, PH 7.1. For each purification, the resin was loaded between 5-15 mg antibody per mL of resin. The antibody concentration in the HCCF was determined using an immobilized protein A HPLC column (Applied Biosystems, POROS A). After loading, the resin was washed with 25 mM Tris, 25 mM NaCl, 5 mM EDTA, 0.5 M TMAC, pH 7.1, and then the antibody was eluted using 0.1M acetic acid, pH 2.9. Elution pooling was based on UV absorbance at 280 nm measured inline after the column. The purified elution pools were pH-adjusted using 1 M Sodium HEPES to pH 5.0-5.5. After regeneration of the resin with 0.1M phosphoric acid, the same or similar packed resins were used for subsequent purification of other HCCF solutions.

The antibody concentration in the purified protein A pool was measured using UV spectrometry at 280 nm. The purified protein A elution pools were analyzed by the Bioanalyzer assay to quantitate the percentage of intact antibody at 150 kDa molecular weight.

Example 2

Dialysis Experiment

Figure 1:
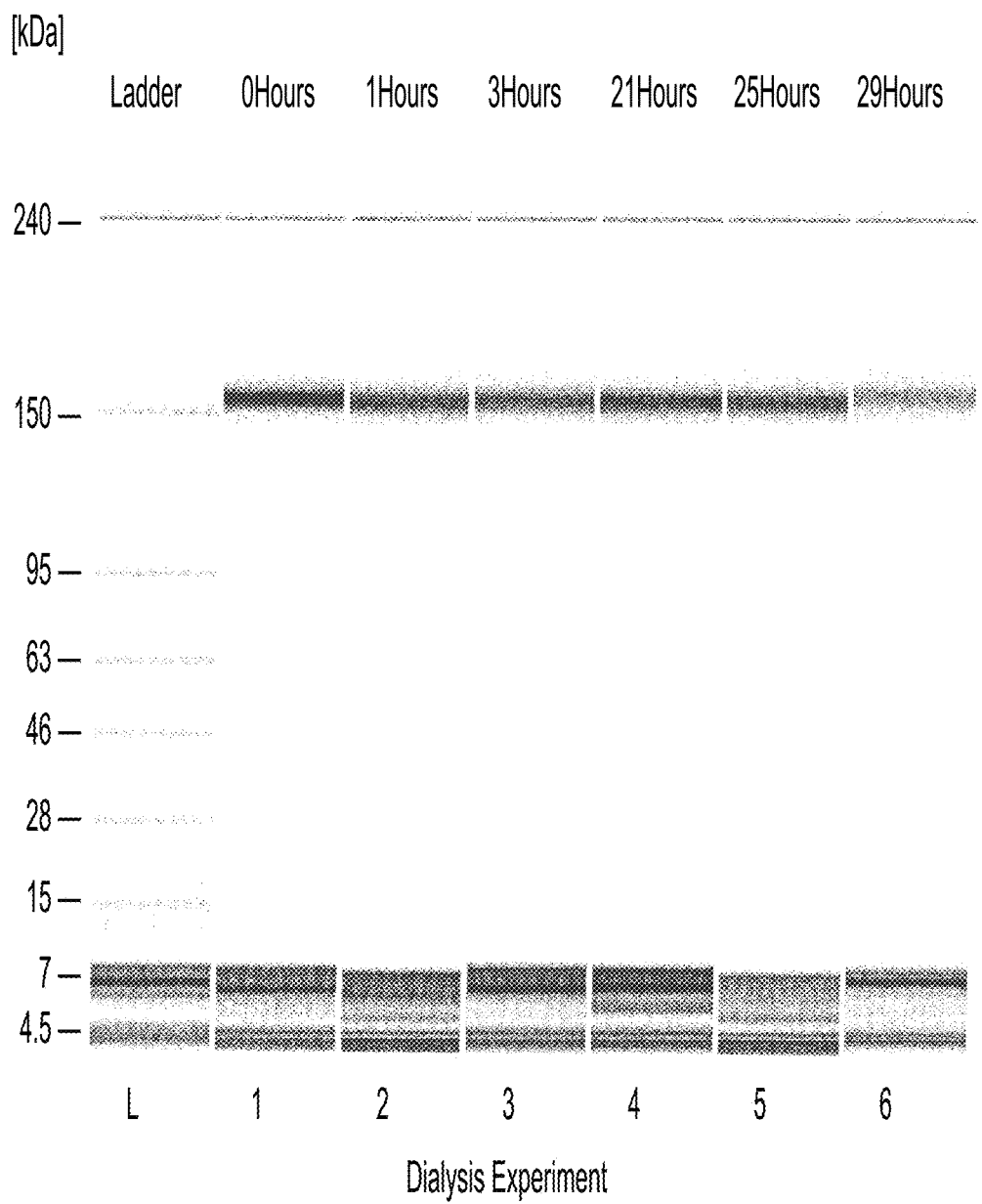
FIG. 1. Dialysis Experiment: Digital gel-like imaging obtained from Bioanalyzer analysis (each lane representing a time point) demonstrating that ocrelizumab (rhuMAb 2H7-Variant A) inside the dialysis bag remained intact during the incubation period.
Figure 2:
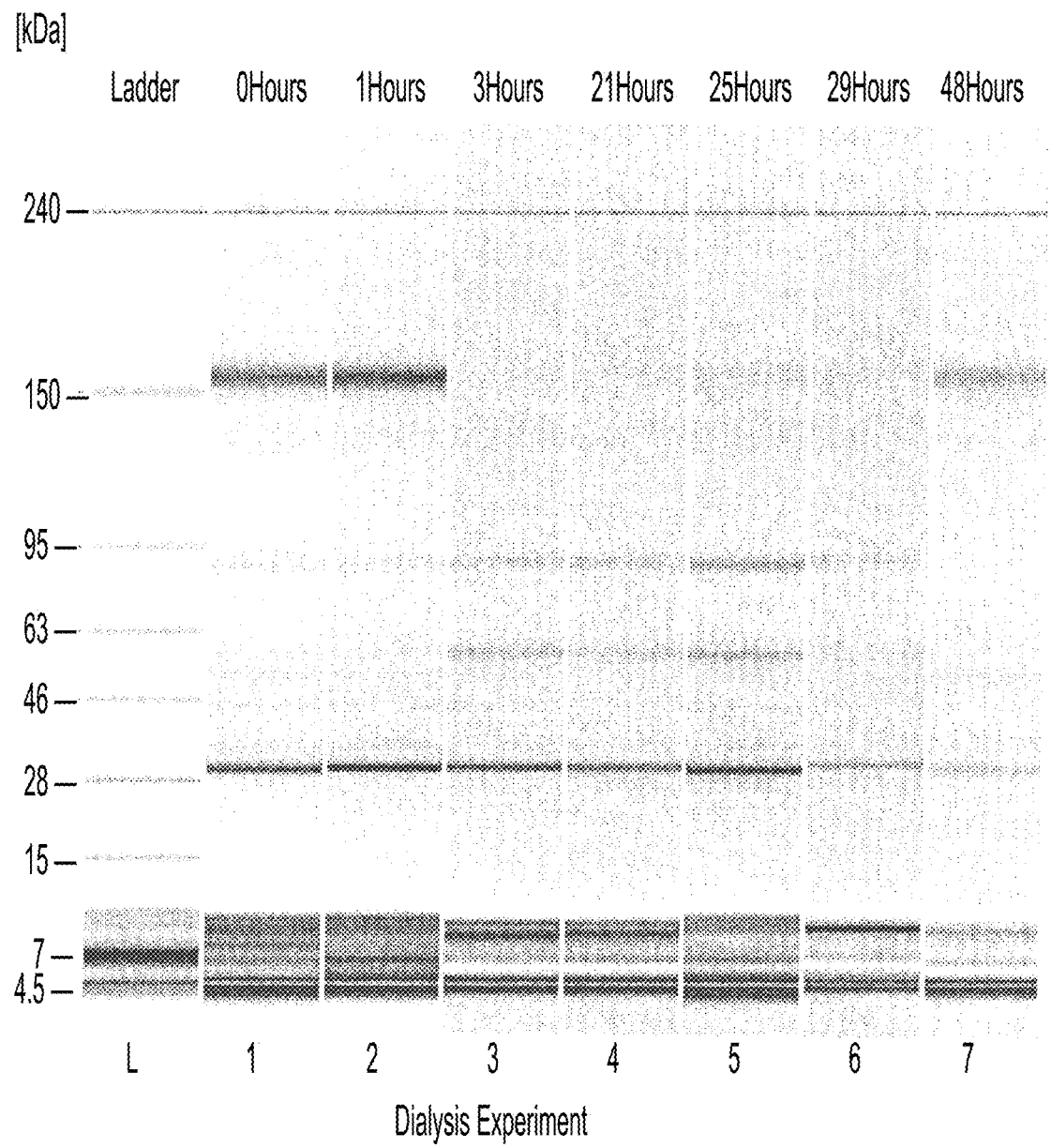
FIG. 2. Dialysis Experiment: Digital gel-like imaging obtained from Bioanalyzer analysis (each lane representing a time point) showing that ocrelizumab outside the dialysis bag was reduced during the incubation period. This is evidenced by the loss of intact antibody (~ 150 kDa) and the formation of antibody fragments depicted in the Figure. At the 48-hour time point (Lane 7), the reduced antibody appeared to be reoxidized, presumably as a result of loosing reduction activity in the Harvested Cell Culture Fluid (HCCF). The band appearing just above the 28 kDa marker arose from the light chain of antibody. There was a significant amount of free light already present in the HCCF before the incubation began. The presence of excess free light chain and dimers of light chain in the HCCF is typical for the cell line producing ocrelizumab.

A dialysis experiment was designed and carried out to determine if the reduction of ocrelizumab was caused by small reducing molecules or macromolecules (e.g., enzymes). In this dialysis experiment, purified intact ocrelizumab was placed in a dialysis bag with a molecular weight cut off (MWCO) of 7000 and incubated the dialysis bag in HCCF containing ocrelizumab in a stainless steel mini-tank. As shown in FIGS. 1 and 2, the ocrelizumab inside the bag was not reduced after the incubation period (FIG. 1), whereas the ocrelizumab outside the bag in the HCCF was significantly reduced soon after the incubation started. This was evidenced by the loss of intact ocrelizumab (~150 kDa) and the formation of ocrelizumab fragments (various combinations of heavy and light chains) (FIG. 2). The mass spectrometry analysis of the ocrelizumab in the protein A elution pools from the reduced manufacturing runs indicated that those observed fragments were formed by reduction of only the inter-chain disulfide bonds.

Figure 3:
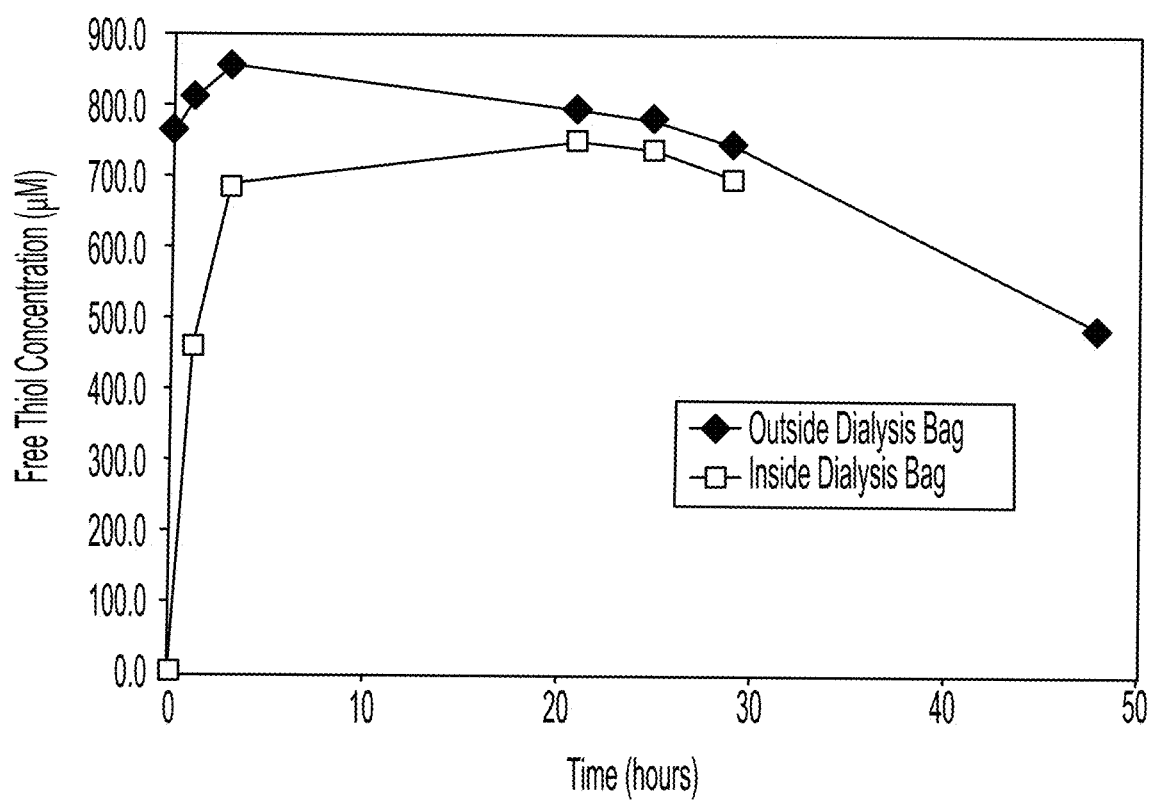
FIG. 3. Free Thiol Levels from Dialysis Experiment: Purified ocrelizumab in phosphate buffered saline (PBS) was inside the dialysis bag and HCCF containing ocrelizumab was outside the bag. Free thiols inside (boxes) and outside (diamonds) the dialysis bag reached comparable levels within a few hours, indicating a good exchange of small molecule components in the HCCF between inside and outside the dialysis bag.

The free thiol measurement showed that no free thiols were present inside the dialysis bag at the beginning of the incubation; however the levels of free thiols inside and outside the dialysis bag become comparable in less than five hours after the incubation started, indicating that the small molecule components in the HCCF are fully equilibrated inside and outside the dialysis bag (FIG. 3). Since the reduction was observed only outside but not inside the dialysis bag with a MWCO of 7000 Da, the molecular weight of the reducing molecule(s) must be greater than 7000 Da. Thus, an enzymatic reaction is responsible for the reduction of ocrelizumab.

Example 3

Reduction of Ocrelizumab (rhuMAb 2H7, Variant A) by Trx/TrxR In Vitro

Figure 5:
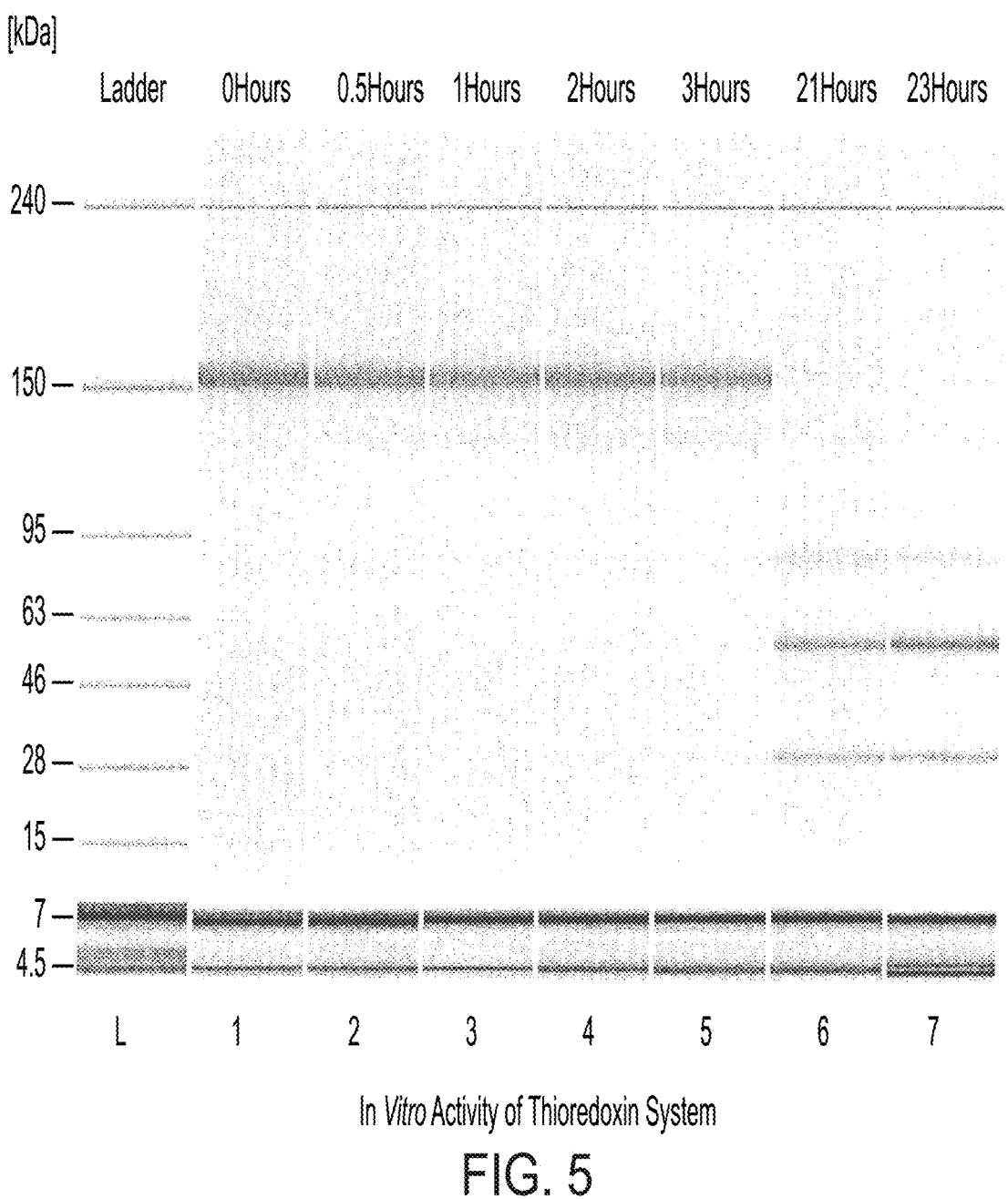
FIG. 5. In Vitro Activity of Thioredoxin System: Digital gel-like image from Bioanalyzer analysis (each lane representing a time point) demonstrating that incubation of intact ocrelizumab (1 mg/mL) with 0.1 mM TrxR (rat liver), 5 mM Trx (human), and 1 mM NADPH in PBS resulted in the complete reduction of ocrelizumab; the ocrelizumab was completely reduced in less than 21 hours.

The Trx system was tested for its ability to reduce ocrelizumab in vitro by incubating intact ocrelizumab with Trx, TrxR, and NADPH. The Bioanalyzer results indicate that ocrelizumab was reduced in vitro by the Trx system (FIG. 5). The rate of reduction in this in vitro system appears to be slower than that in the HCCF (for example when compared to the reduction shown in FIG. 2). This is likely due to lower concentrations of the enzymes (Trx and Trx-R) and/or the buffer system used in the in vitro reaction because reaction rate of Trx system is dependent on both the enzyme concentrations and buffer systems.

Example 4

Figure 8:
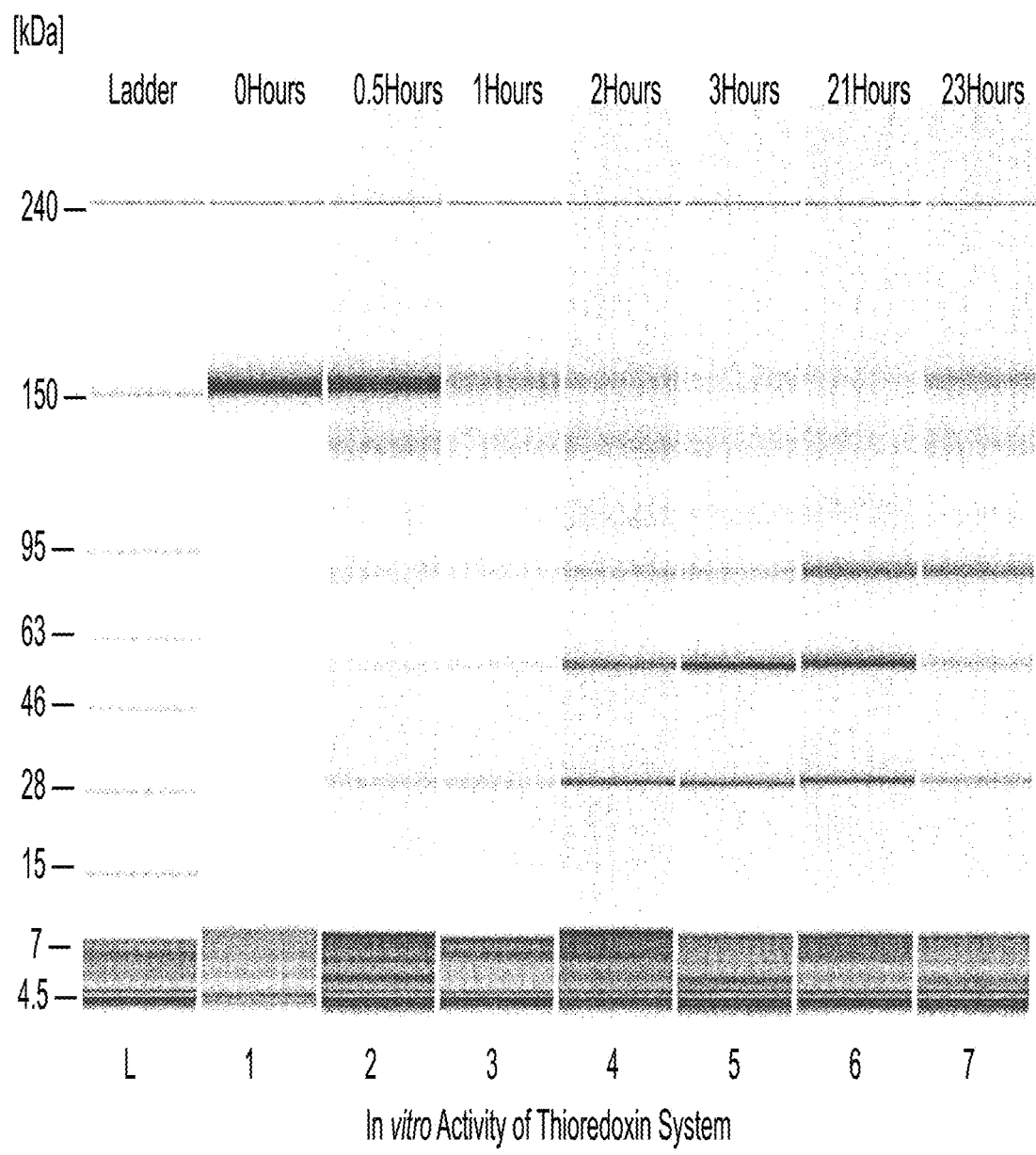
FIG. 8. In Vitro Activity of Thioredoxin System: Digital gel-like image from Bioanalyzer analysis (each lane representing a time point) showing that incubation of intact ocrelizumab (1 mg/mL) with 0.1 mM TrxR (rat liver), 5 mM Trx (human), and 1 mM NADPH in 10 mM histidine sulfate buffer resulted in the reduction of ocrelizumab in less than 1 hour.
Figure 9:
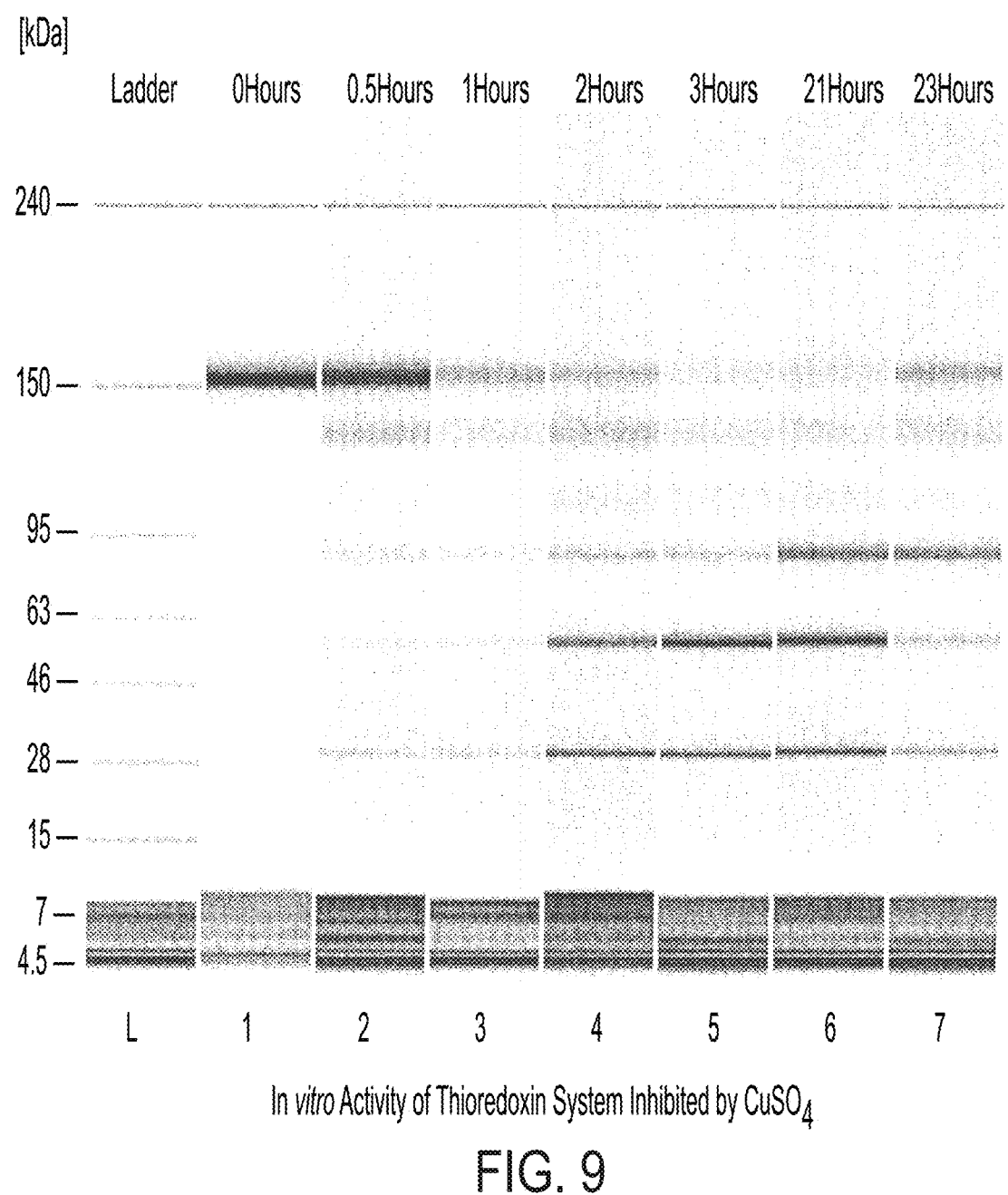
FIG. 9. In vitro Activity of Thioredoxin System Inhibited by $CuSO_4$: The addition of $CuSO_4$ at a concentration of 50 ☐M to the same reaction mixture as described in the caption for FIG. 8 effectively inhibited the ocrelizumab reduction as shown in the digital gel-like image from Bioanalyzer analysis (each lane representing a time point).

Inhibitors of the Trx System
(i) Inhibition of Reduction of Recombinant Antibody by Cupric Sulfate Cupric sulfate is known for its ability to provide oxidizing redox potential and has been used in the cell culture processes to minimize free thiol (i.e., minimize unpaired cysteine) levels in recombinant antibody molecules (Chaderjian et al., 2005, supra). Cupric sulfate was tested for efficacy in inhibiting the Trx system in vitro and the subsequent reduction of ocrelizumab. In this in vitro reduction experiment, the buffer system was changed from PBS to histidine sulfate to avoid the formation of insoluble $Cu^3(PO_4)_2$. FIG. 8 shows that ocrelizumab was readily reduced by the Trx system in the histidine sulfate buffer (even faster than in PBS buffer). The addition of $CuSO_4$ to this reaction clearly inhibits the ocrelizumab reduction (FIG. 9).

(ii) Inhibition of Reduction of Recombinant Antibody in HCCF by ATG and ATM

Figure 6:
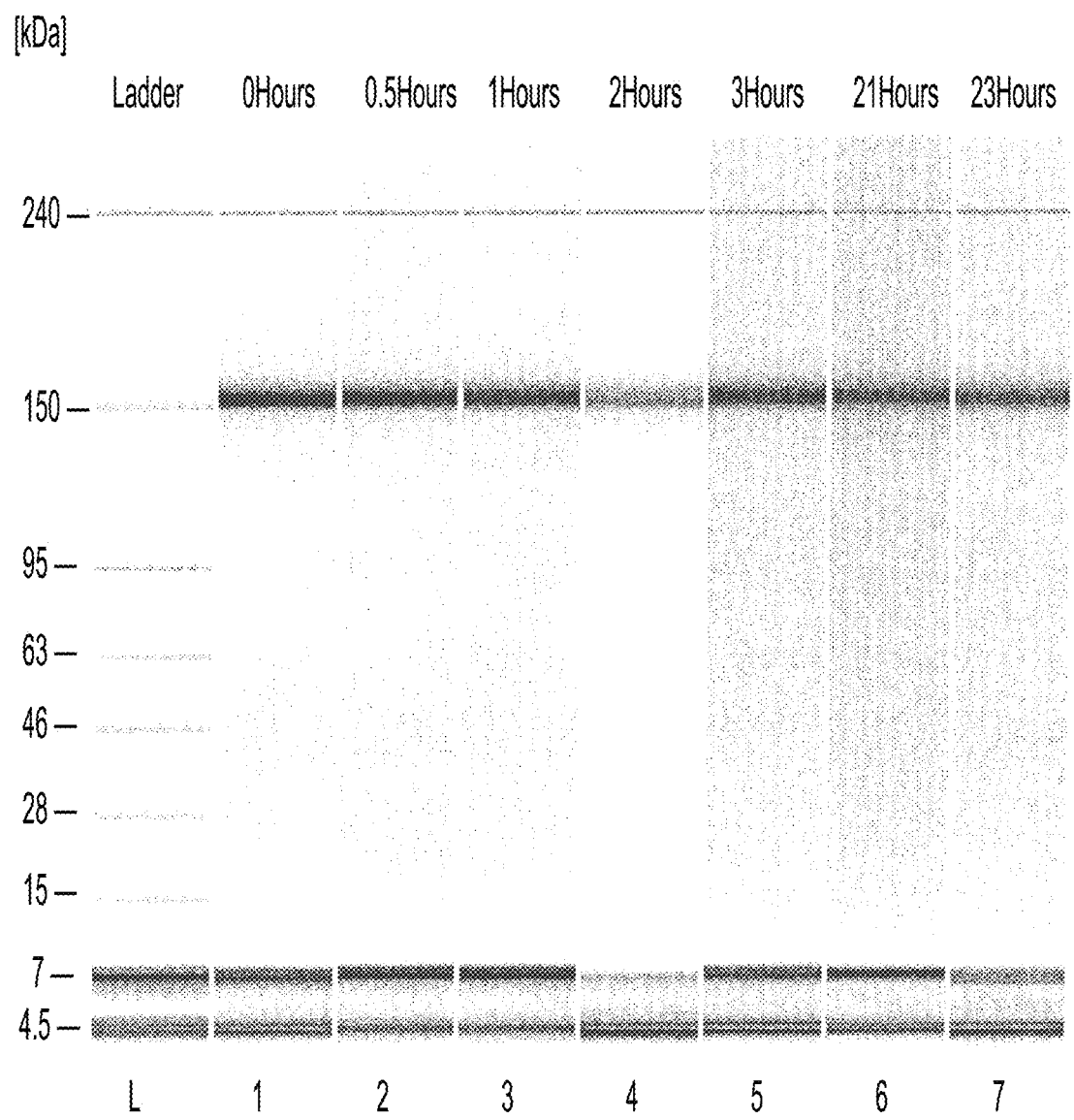
FIG. 6. In Vitro Activity of Thioredoxin System Inhibited by Aurothioglucose: The addition of aurothioglucose (ATG) to the same reaction mixture as described in the caption for FIG. 5, above, effectively inhibited the ocrelizumab reduction. This is seen by the digital gel-like image from Bioanalyzer analysis (each lane representing a time point).
Figure 7:
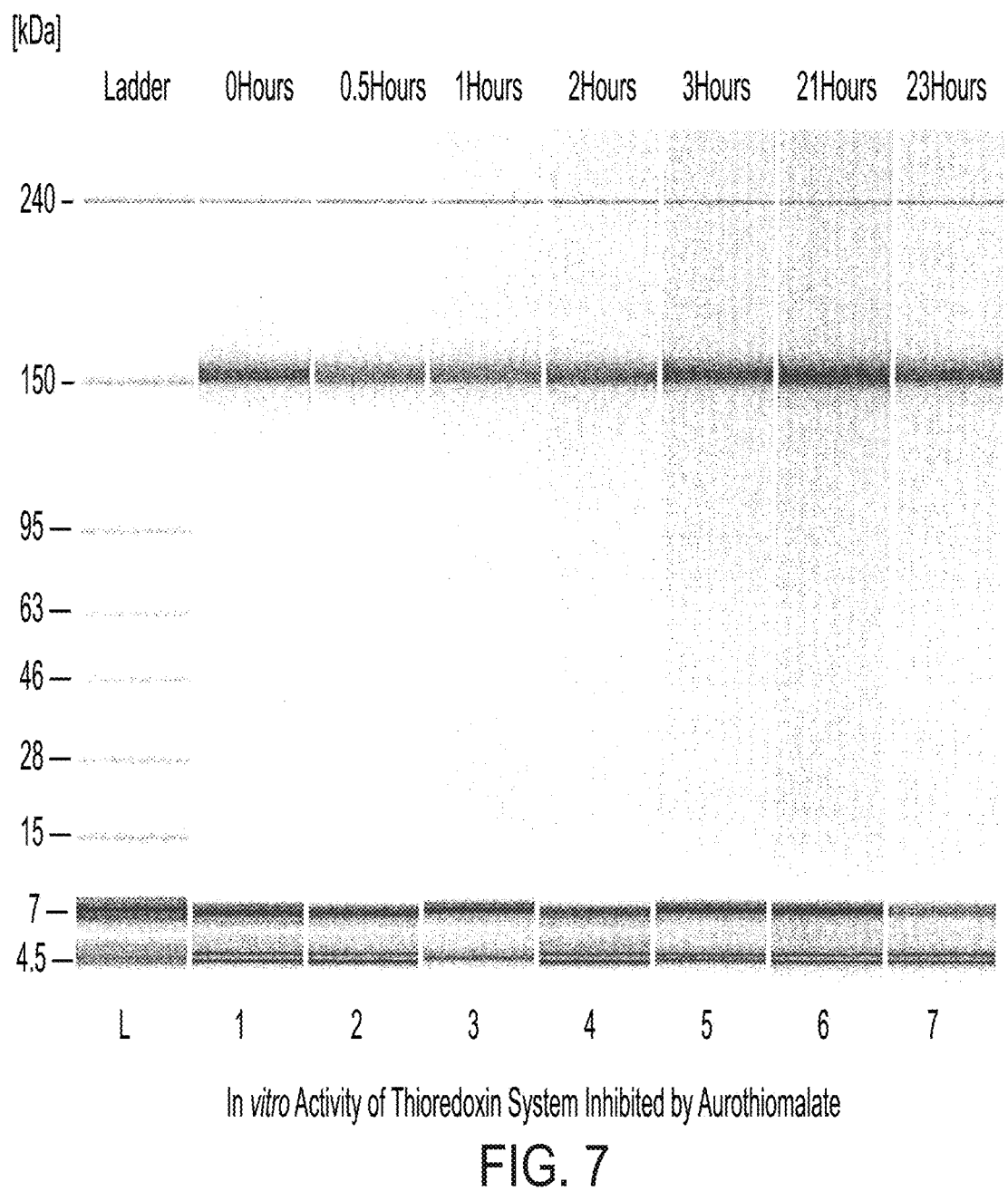
FIG. 7. In vitro Activity of Thioredoxin System Inhibited by Aurothiomalate: The addition of aurothiomalate (ATM) at a concentration of 1 mM to the same reaction mixture as described in the caption for FIG. 5, above, effectively inhibited the ocrelizumab reduction. This is seen by the digital gel-like image from Bioanalyzer analysis (each lane representing a time point).

Two commercially available specific inhibitors of TrxR, aurothioglucose (ATG) and aurothiomalate (ATM), were tested for their ability to inhibit the Trx system in vitro and the reduction of ocrelizumab. Both ATG and ATM can effectively inhibit the reduction of ocrelizumab in the assay described above (see FIGS. 6 and 7). The addition of aurothioglucose or aurothiomalate, at a concentration of 1 mM to the same reaction mixture as described in the caption for FIG. 5 effectively inhibited the ocrelizumab reduction as shown in the digital gel-like image from Bioanalyzer analysis.

Figure 10:
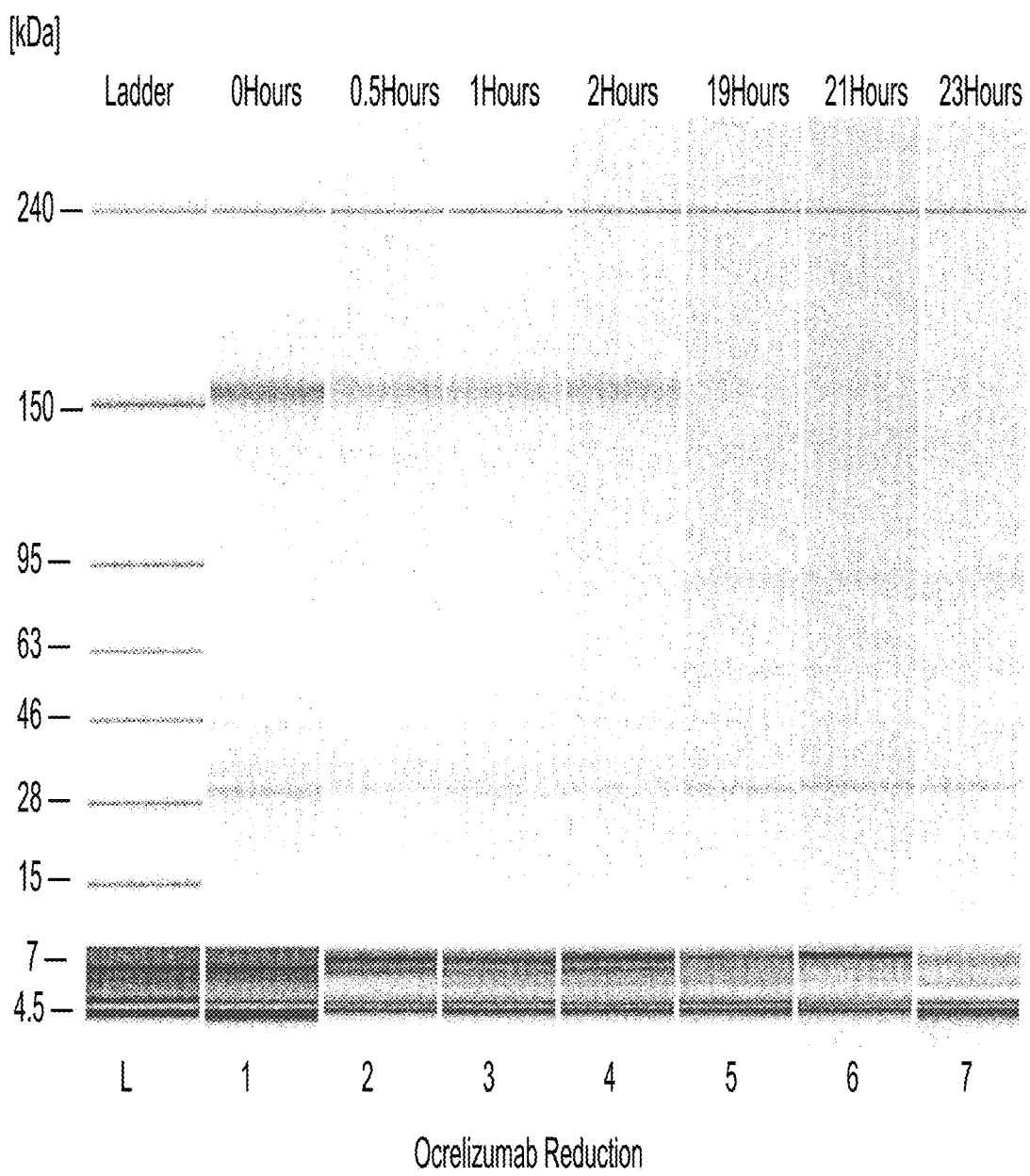
FIG. 10. Ocrelizumab Reduction: Digital gel-like image from Bioanalyzer analysis (each lane representing a time point) showing that ocrelizumab was reduced in an incubation experiment using HCCF from a homogenized CCF generated from a 3-L fermentor.
Figure 11:
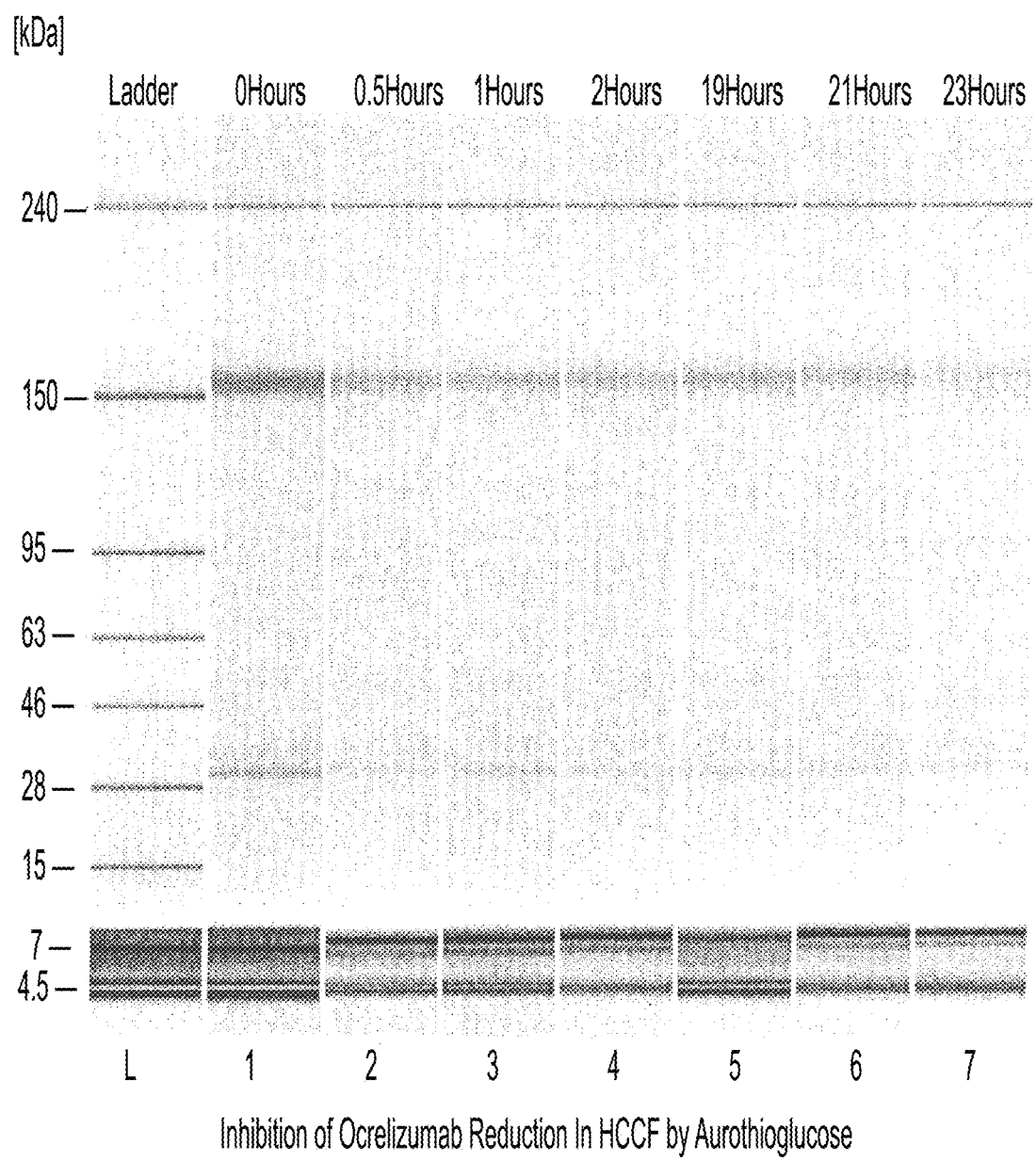
FIG. 11. Inhibition of Ocrelizumab Reduction In HCCF by Aurothioglucose: Digital gel-like image from Bioanalyzer analysis (each lane representing a time point) showing that the addition of 1 mM aurothioglucose to the same HCCF as used for the incubation experiment as shown in FIG. 10 inhibited the reduction of ocrelizumab.
Figure 12:
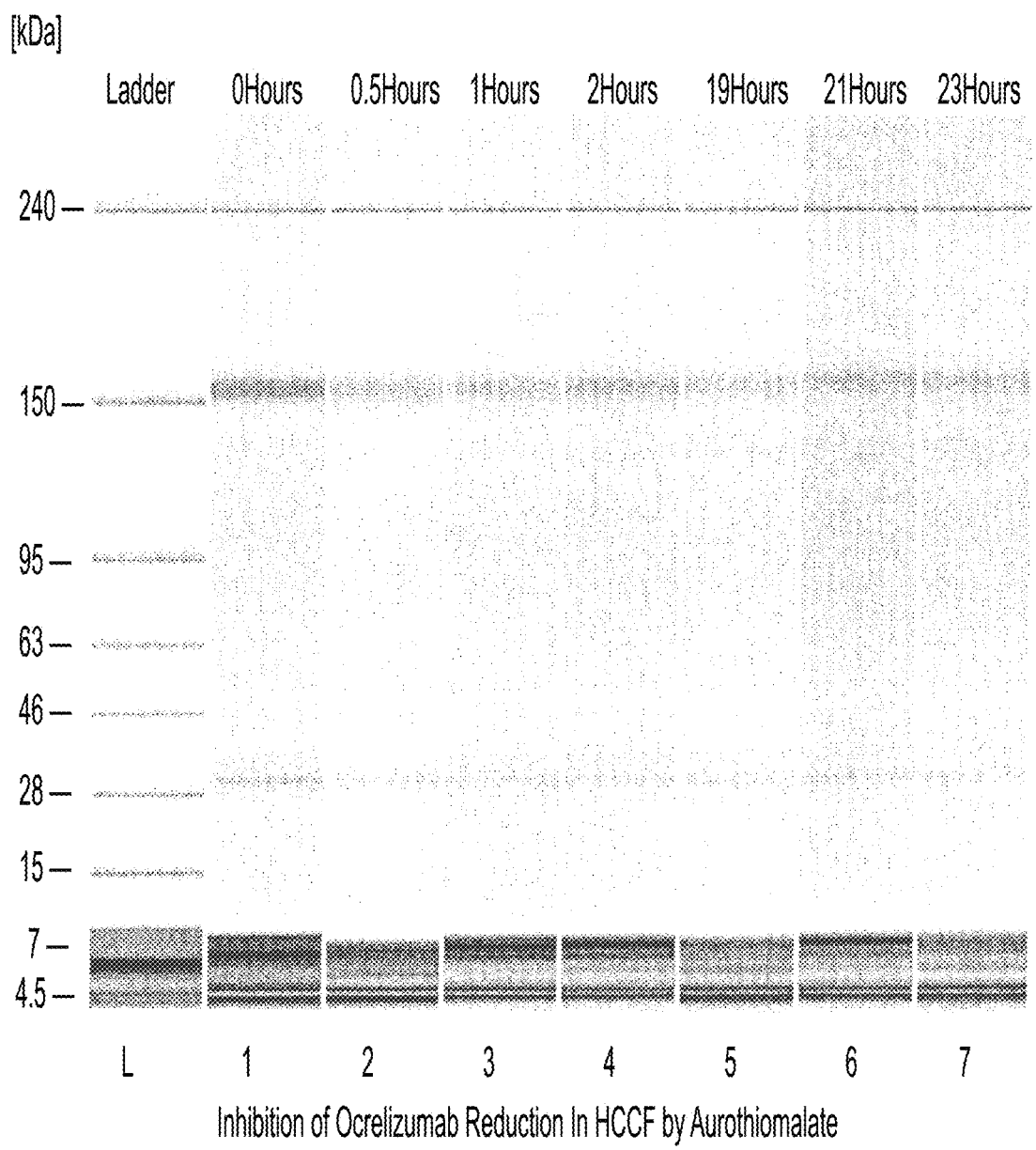
FIG. 12. Inhibition of Ocrelizumab Reduction In HCCF by Aurothiomalate: Digital gel-like image from Bioanalyzer (each lane representing a time point) analysis indicating that the addition of 1 mM aurothiomalate to the same HCCF as used for the incubation experiment shown in FIG. 10 inhibited the reduction of ocrelizumab.

If the Trx system was active in the HCCF and reduced ocrelizumab as observed in the manufacturing runs resulting in reduced antibody molecules or in the lab scale experiments, both gold compounds (ATG and ATM) should be able to inhibit the reduction of ocrelizumab in HCCF. FIG. 10 shows that ocrelizumab was readily reduced in an HCCF from homogenized CCT generated from a 3-L fermentor after a period of incubation. However, the ocrelizumab reduction event was completely inhibited when either 1 mM ATG or ATM was added to the HCCF (FIGS. 11 and 12). These results demonstrated that the Trx system is active in the HCCF and is directly responsible for the reduction of ocrelizumab.

Example 5

Figure 4:
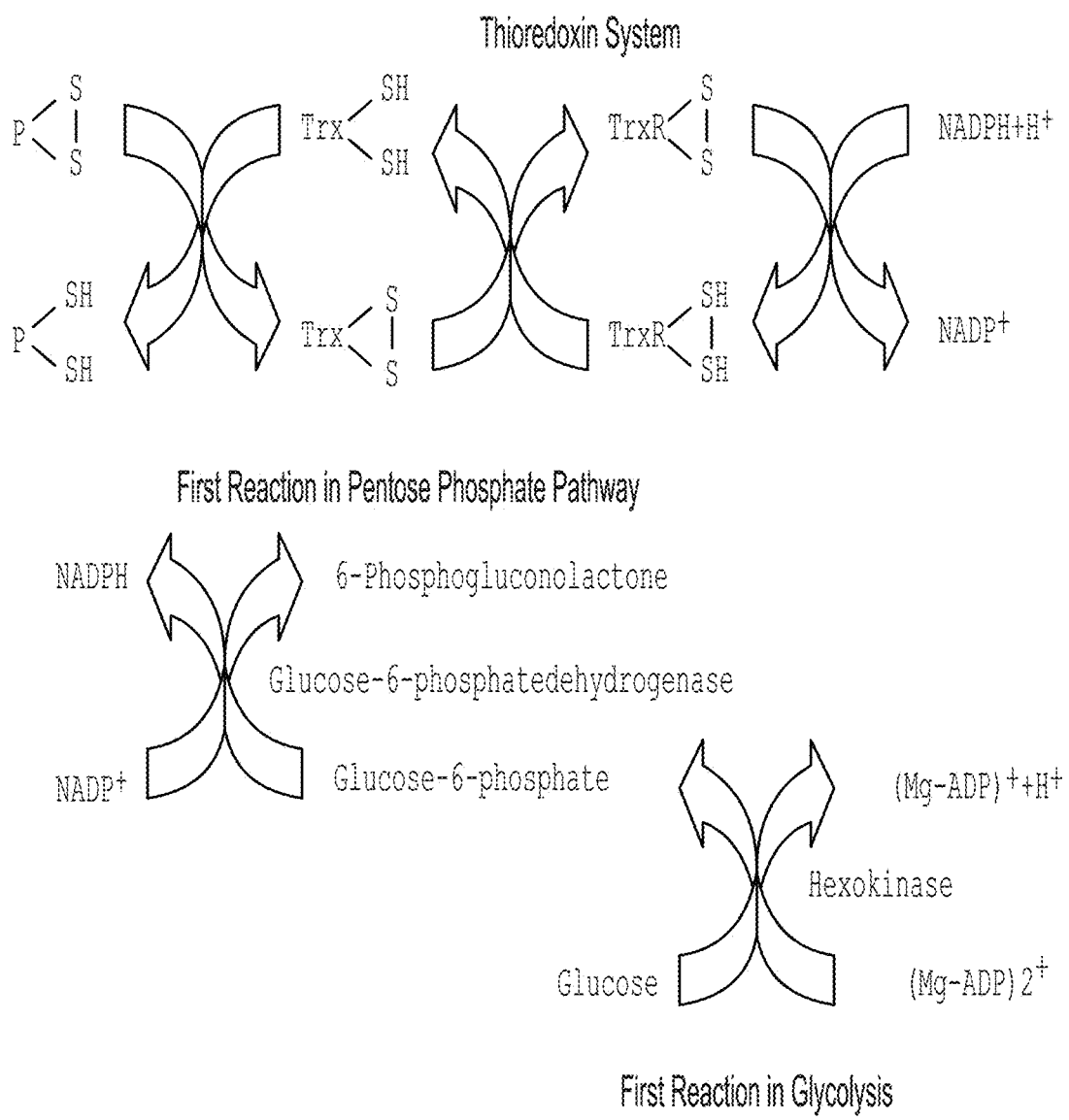
FIG. 4. Thioredoxin System and Other Reactions Involved in Antibody Reduction: The thioredoxin system, comprising thioredoxin (Trx), thioredoxin reductase (TrxR) and NADPH, functions as a hydrogen donor system for reduction of disulfide bonds in proteins. Trx is a small monomeric protein with a CXXC active site motif that catalyzes many redox reactions through thiol-disulfide exchange. The oxidized Trx can be reduced by NADPH via TrxR. The reduced Trx is then able to catalyze the reduction of disulfides in proteins. The NADPH required for thioredoxin system is provided via reactions in pentose phosphate pathway and glycolysis.

The Source of NADPH for Trx System Activity and the Roles of G6P and Glucose in Reduction Mechanism The reduction of disulfides by the Trx system requires the reducing equivalents from NADPH (FIG. 4). The main cellular metabolic pathway that provides NADPH for all reductive biosynthesis reactions is the pentose phosphate pathway. For the antibody reduction event to occur, the enzymes in this pathway must be still active in the HCCF in order to keep the Trx system active. At a minimum, the first step in the pentose phosphate pathway (catalyzed by G6PD) must be active to reduce $NADP^+$ to NADPH while converting G6P to 6-phosphogluconolactone. In addition, G6P is most likely produced from glucose and adenosine 5'-triphosphate (ATP) by the hexokinase activity in HCCF. The overall mechanism of ocrelizumab reduction is summarized in FIG. 4.

The reducing activity in the HCCF appeared to be transitory in some cases and may be inhibited over time under certain storage conditions or after multiple freeze/thaw cycles. HCCF that has fully lost reducing activity provided an opportunity to explore the role of NADPH and G6P in the reduction of ocrelizumab by Trx system.

Figure 13:
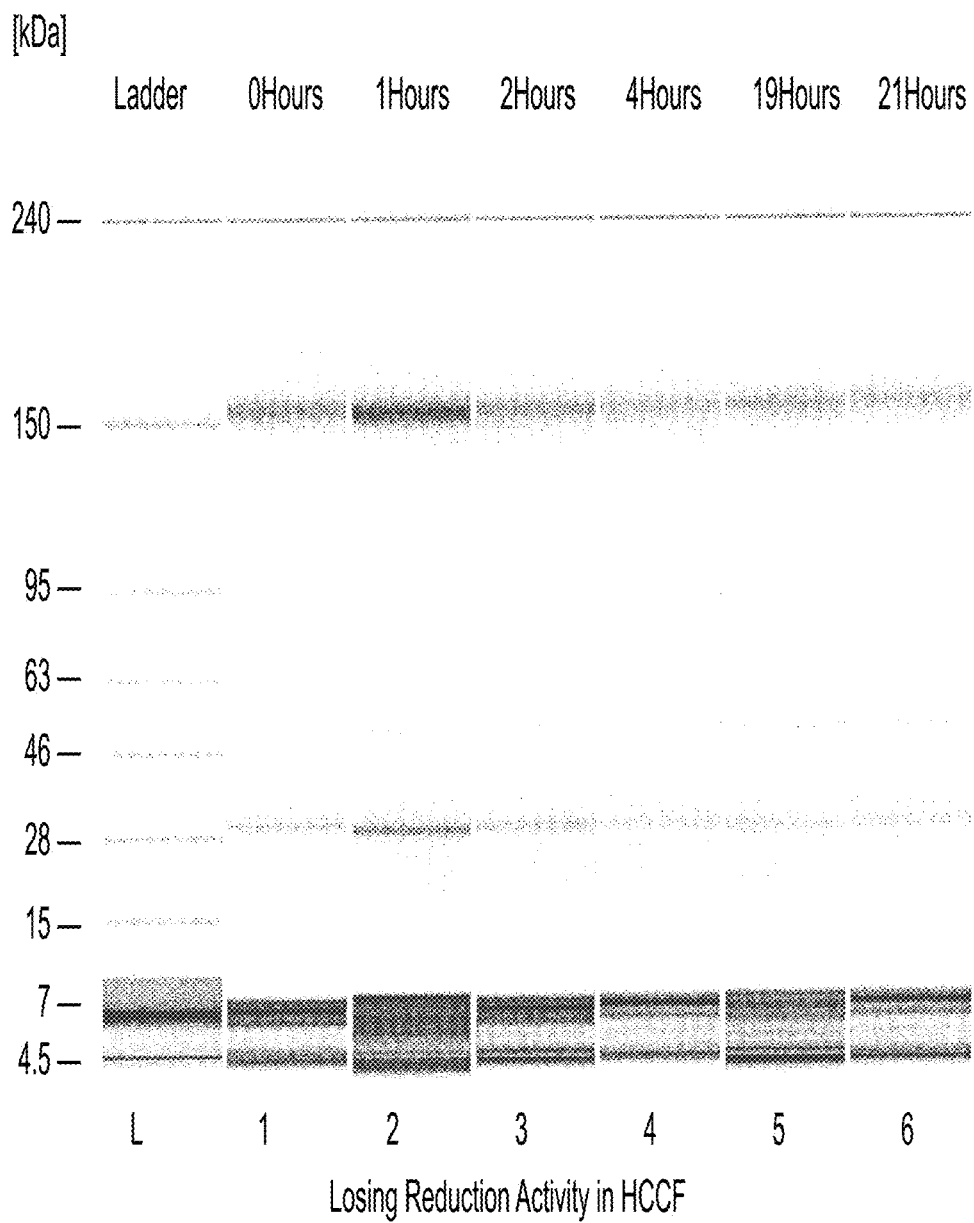
FIG. 13. Losing Reduction Activity in HCCF: The HCCF from one of the large scale manufacturing runs for ocrelizumab (the "beta" run) that was subject to several freeze/thaw cycles demonstrated no ocrelizumab reduction when used in an incubation experiment. This was shown by Bioanalyzer analysis (each lane representing a time point), and can be contrasted to the antibody reduction seen previously in the freshly thawed HCCF from the same fermentation batch.
Figure 14:
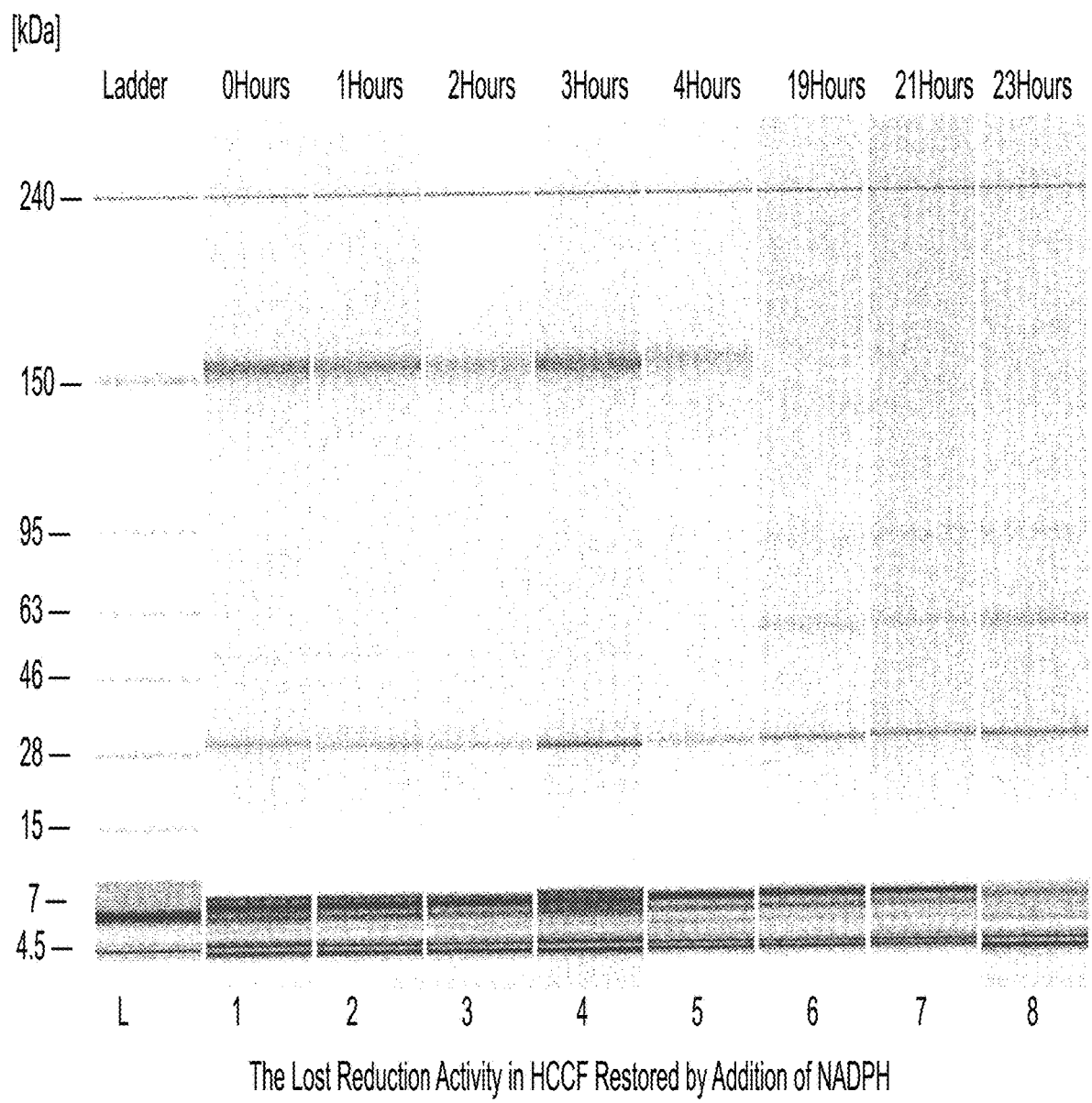
FIG. 14. The Lost Reduction Activity in HCCF Restored by Addition of NADPH: The reduction of ocrelizumab was observed again in the Bioanalyzer assay (each lane representing a time point) after the addition of NADPH at a concentration of 5 mM into the HCCF where the reduction activity has been eliminated under the conditions described above in FIG. 13.
Figure 15:
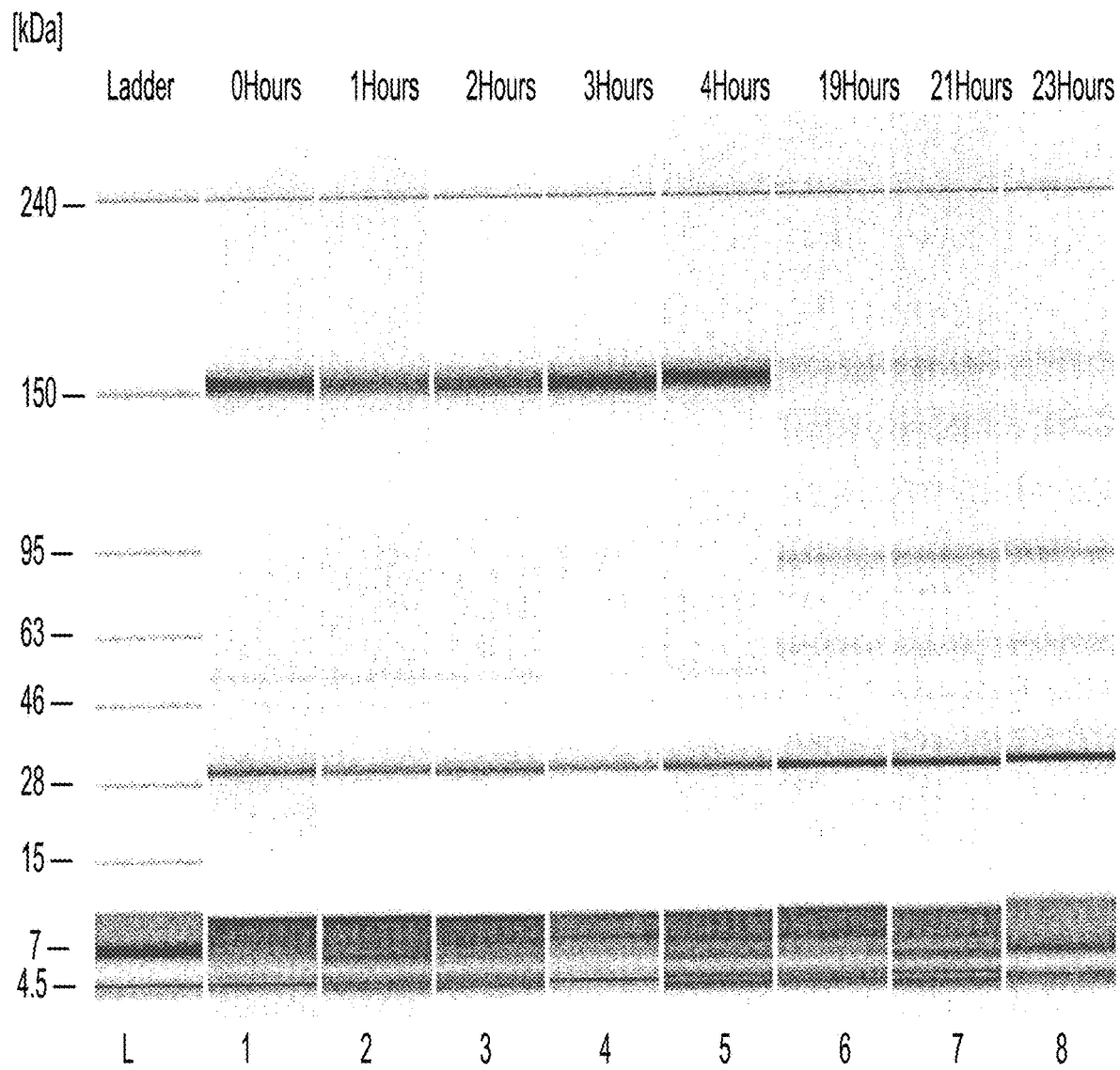
FIG. 15. The Lost Reduction Activity in HCCF Restored by Addition of Glucose-6-Phosphate: The reduction of ocrelizumab was observed again in the Bioanalyzer assay (each lane representing a time point) after the addition of G6P at a concentration of 10 mM into the HCCF where the reduction activity has been eliminated due to the treatment described above in FIG. 13.
Figure 16:
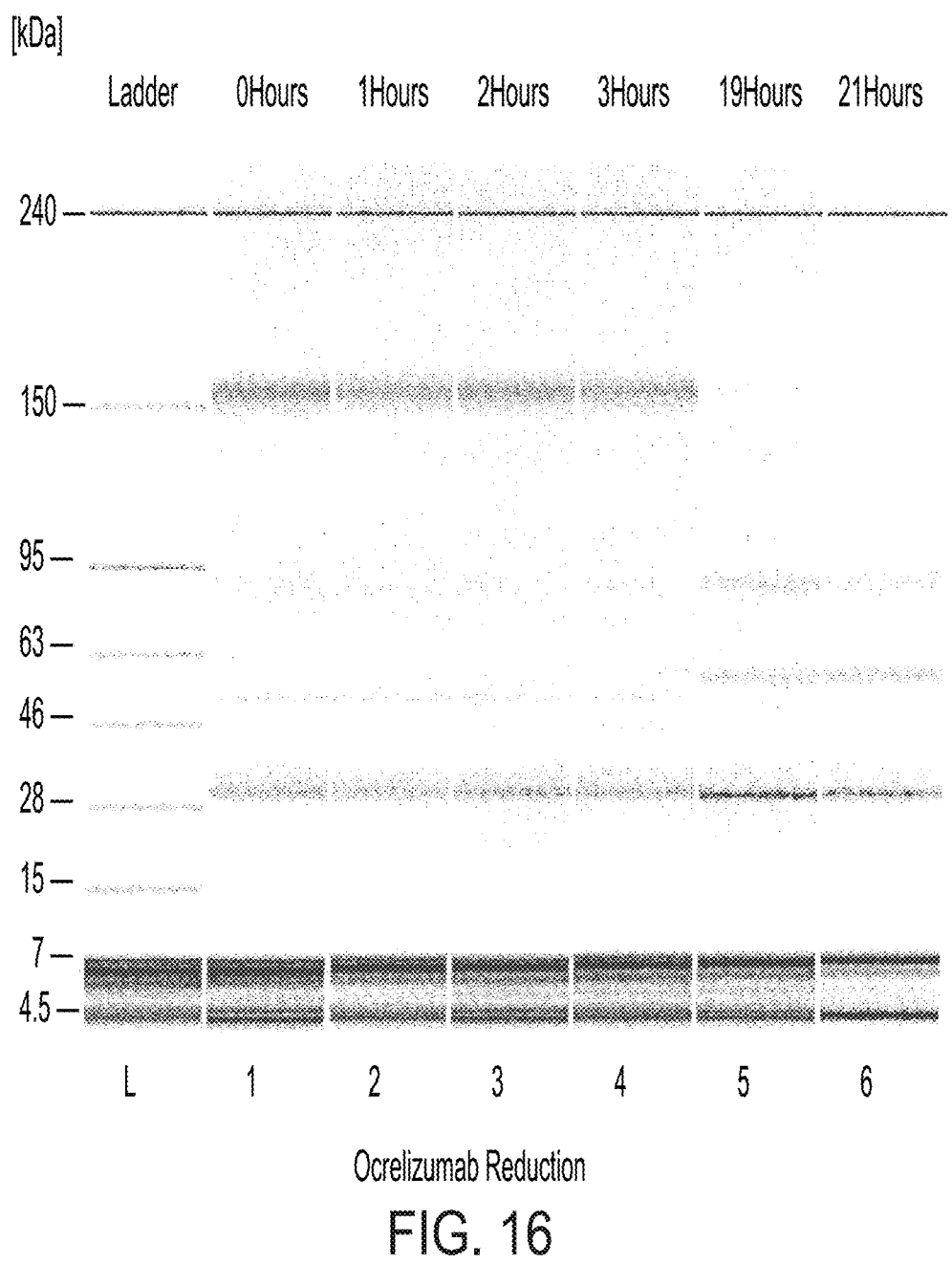
FIG. 16. Ocrelizumab Reduction: A digital gel-like image from Bioanalyzer analysis showing that ocrelizumab was reduced in an incubation experiment using a HCCF from a large scale manufacturing run (the "alpha" run).
Figure 17:
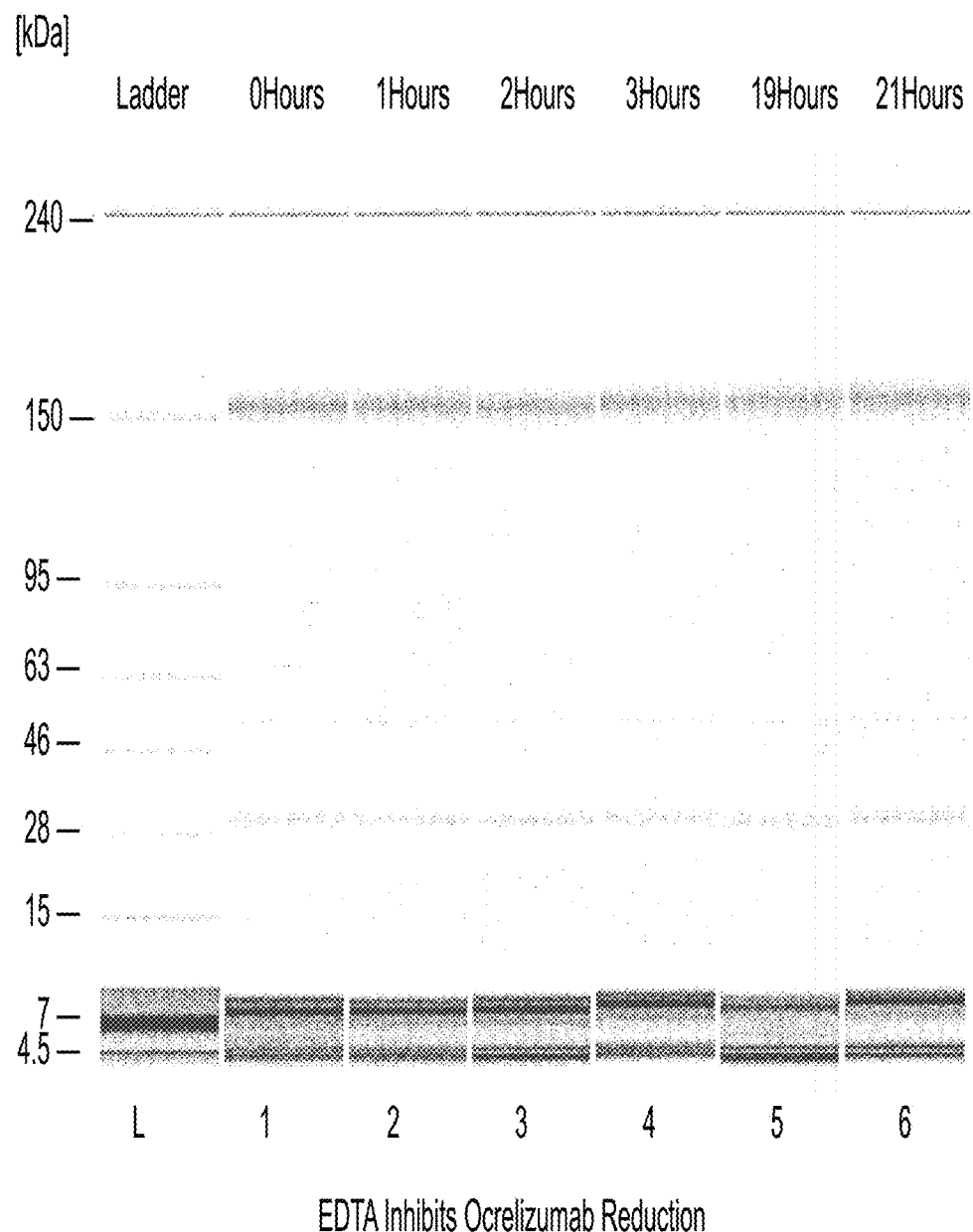
FIG. 17. EDTA Inhibits Ocrelizumab Reduction: Digital gel-like image from Bioanalyzer analysis (each lane representing a time point) showing that the reduction of ocrelizumab was inhibited in an incubation experiment using a HCCF from the alpha run with EDTA added at a concentration of 20 mM to the HCCF whose reducing activity is demonstrated in FIG. 16.
Figure 18:
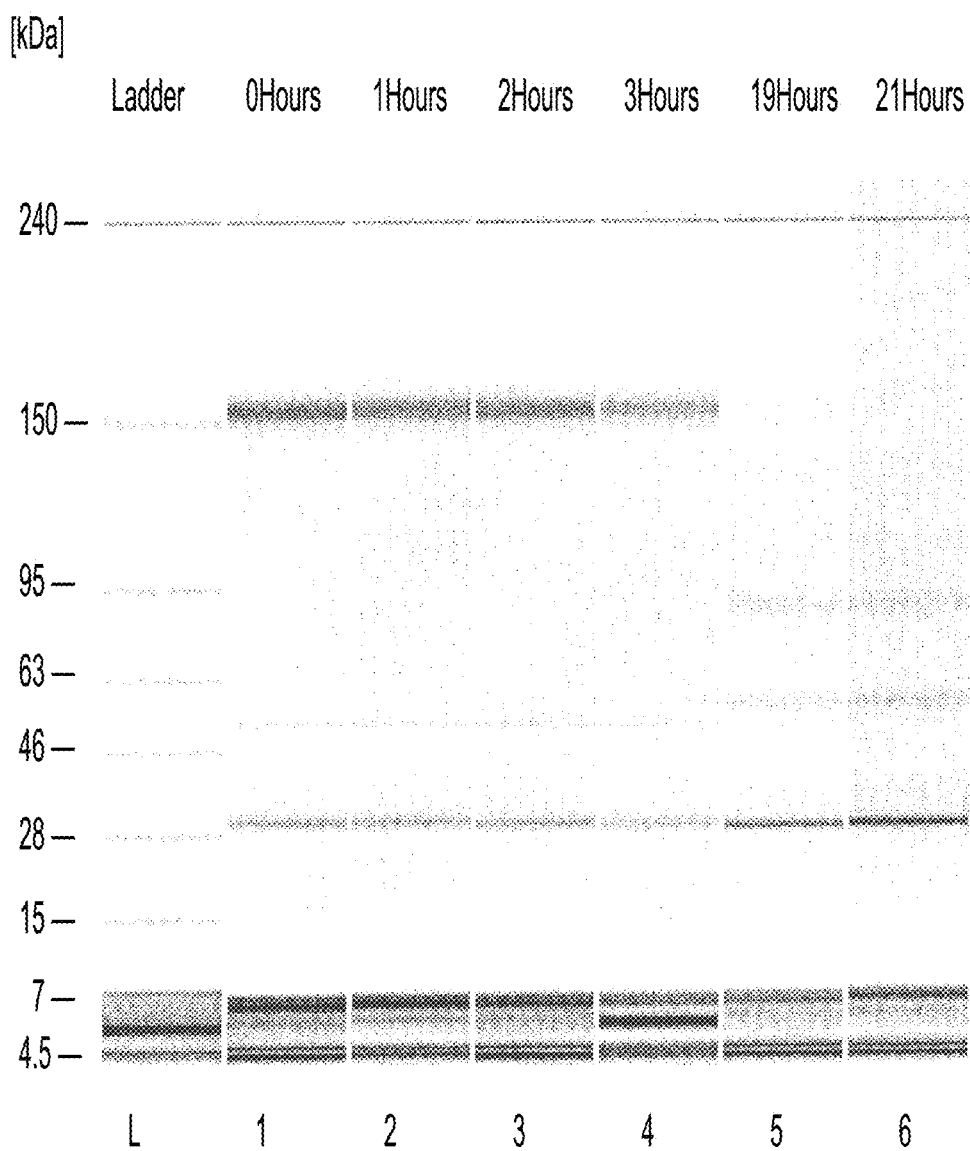
FIG. 18. The Lost Reduction Activity in "Beta Run" HCCF Restored by Addition of Glucose-6-Phosphate but No Inhibition of Reduction by EDTA: The reduction of ocrelizumab was observed in the Bioanalyzer assay (each lane representing a time point) after the addition of G6P at a concentration of 5 mM and 20 mM EDTA into the HCCF whose reduction activity had been lost (see FIG. 13). In contrast to the results shown in FIG. 17, the presence of EDTA did not block the reduction of ocreliumab.
Figure 19:
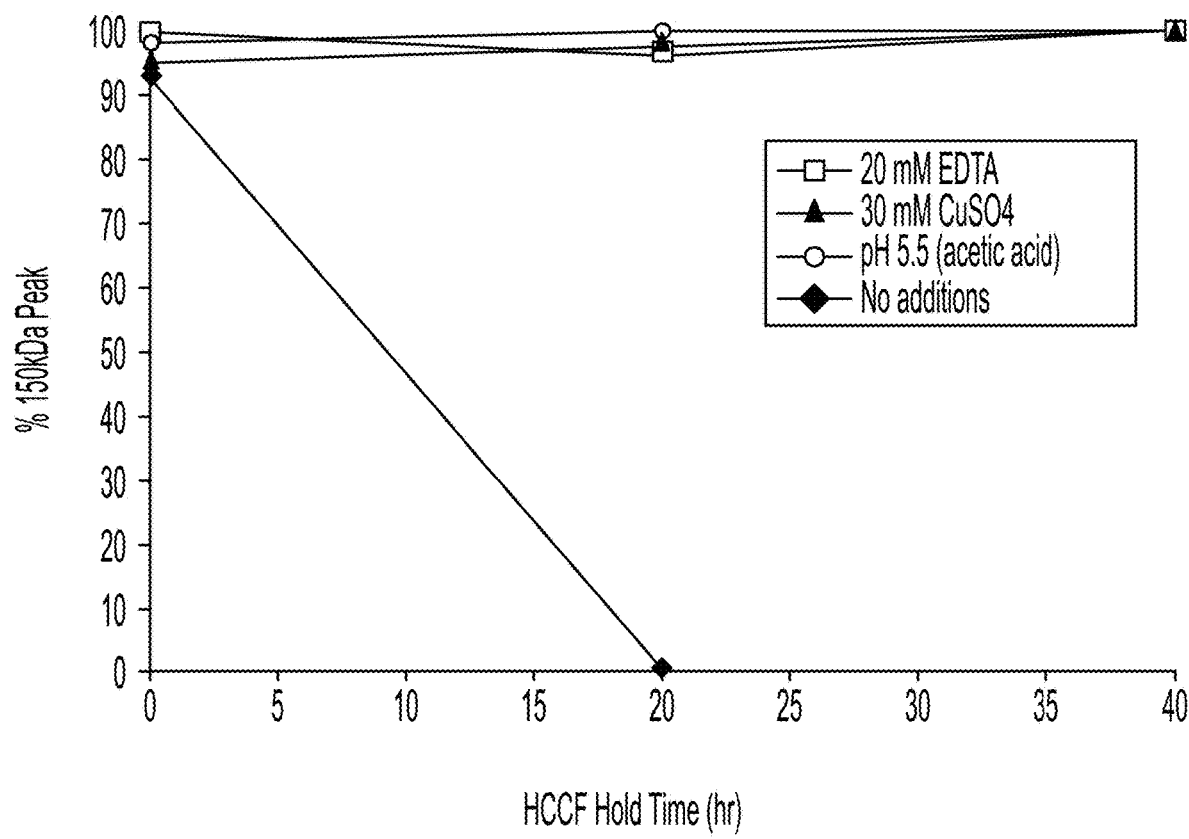
FIG. 19. Inhibition of Ocrelizumab Reduction: by (i) addition of EDTA, (ii) addition of $CuSO_4$, or (iii) adjustment of pH to 5.5. All three different methods, (1) addition of EDTA, (2) addition of $CuSO_4$, and (3) adjustment of pH to 5.5, used independently, were effective in inhibiting ocrelizumab reduction. This was demonstrated by the depicted quantitative Bioanalyzer results that showed that nearly 100% intact (150 kDa) antibody remained in the protein A elution pools. In contrast, ocrelizumab was completely reduced in the control HCCF after 20 hours of HCCF hold time.
Figure 20:
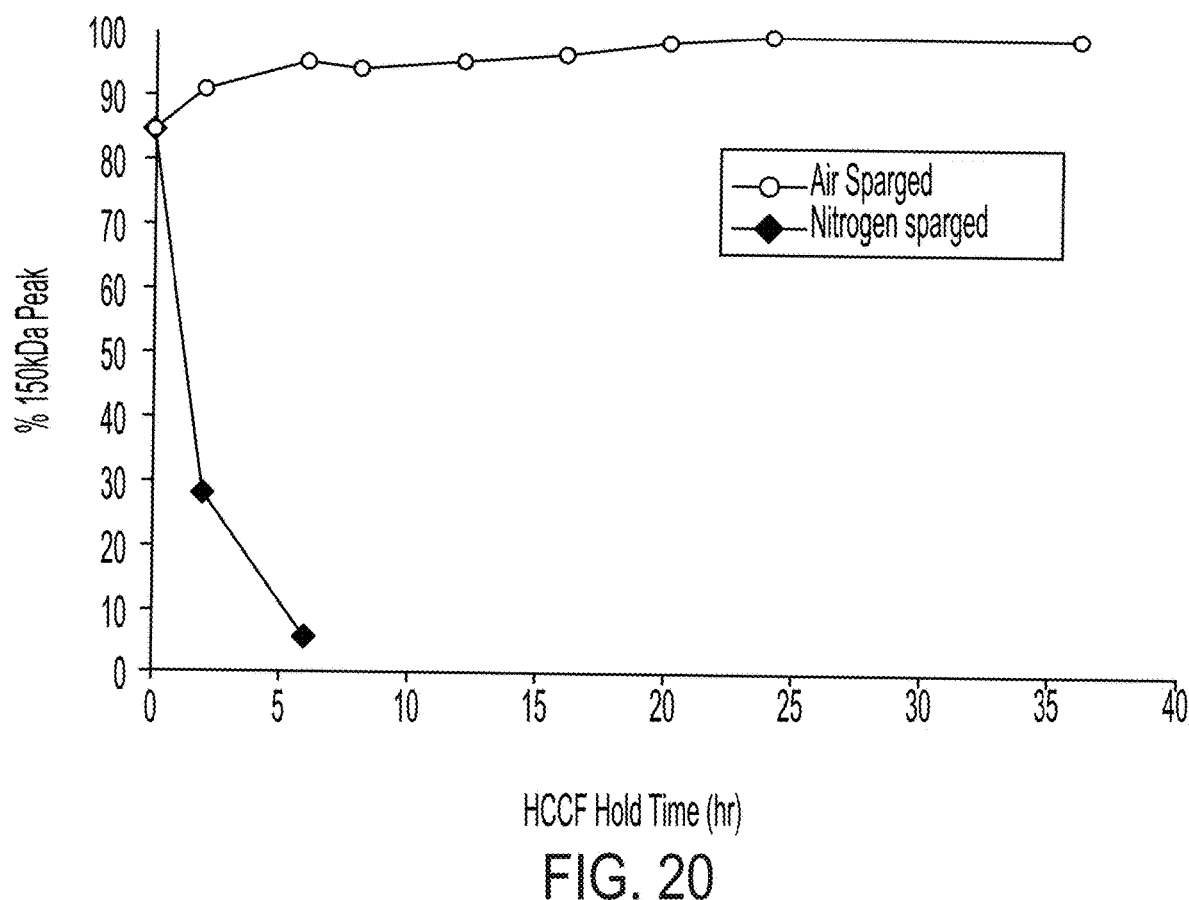
FIG. 20. Inhibition of Ocrelizumab Reduction by Air Sparging: Sparging the HCCF with air was effective in inhibiting ocrelizumab disulfide bond reduction. This was demonstrated by the quantitative Bioanalyzer results showing that nearly 100% intact (150 kDa) antibody remained in the protein A elution pools. In contrast, ocrelizumab was almost completely reduced in the control HCCF after 5 hours of sparging with nitrogen.
Figure 23:
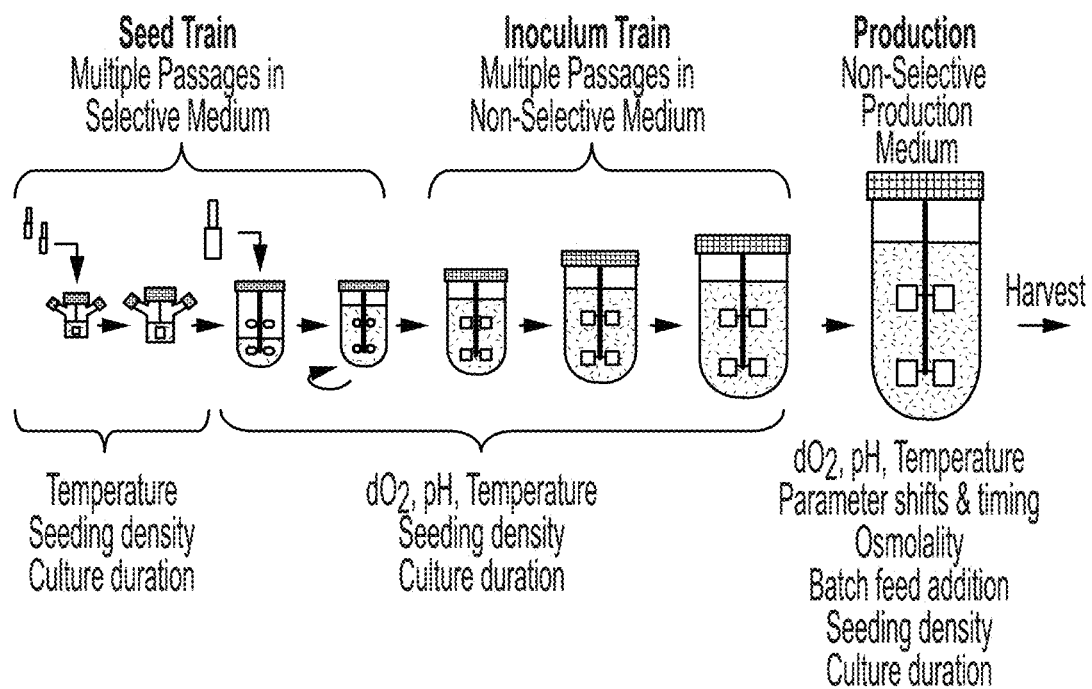
FIG. 23 is a schematic showing some steps of a typical large scale manufacturing process.

An HCCF from a large scale manufacturing run (the "beta" run) was subjected to several freeze/thaw cycles and used in an experiment designed to measure reduction; no ocrelizumab reduction was observed (FIG. 13) despite its ability to bring about antibody reduction seen previously in freshly-thawed HCCF from this same fermentation. NADPH was added to this non-reducing HCCF at a concentration of 5 mM and the reduction event returned (FIG. 14). Therefore, the Trx system is still intact and active in the HCCF where reduction no longer occurs, and capable of reducing protein and/or antibody if supplied with cofactors. Additionally, the reducing activity was lost over time as the NADPH source was depleted (presumably due to the oxidation of NADPH by all of the reductive reactions that compete for NADPH), and not because the Trx system was degraded or inactivated.

This was verified by another experiment. 10 mM G6P was added to a HCCF that had been repeatedly freeze-thawed from the beta run. This G6P addition reactivated the Trx system which subsequently reduced ocrelizumab in the HCCF incubation experiment (FIG. 15). This demonstrated that the reduction of ocrelizumab in the HCCF was caused by the activities of both the Trx system and G6PD. Furthermore, G6PD is still active in a repeatedly freeze/thawed HCCF of the beta run; the loss of reduction activity in this a repeatedly freeze/thawed HCCF beta run appears to be due to the depletion of G6P, which thus eliminated the conversion of $NADP^+$ to NADPH.

In our studies, we have observed that EDTA can effectively inhibit the ocrelizumab reduction in the HCCF incubation experiment. As shown in FIG. 16, the ocrelizumab was reduced after incubating the HCCF from a 12,000 L scale ocrelizumab manufacturing run (not repeatedly freeze/thawed and no loss of reducing activity) at ambient temperature for more than 19 hours. However, the reduction was completely inhibited when 20 mM EDTA was added to the 12 kL HCCF and held in a separate stainless steel minitank (FIG. 17). In the first step of glycolysis, the hexokinase catalyzes the transfer of phosphate group from Mg2+-ATP to glucose, a reaction that requires the complexation of $Mg^{2+}$ with ATP (Hammes & Kochavi, 1962a & 1962b, supra). Since EDTA is a metal ion chelator, especially for Mg2+, it can be an effective inhibitor of hexokinase. The observation that an excess amount of EDTA can effectively block the reduction indicates the involvement of hexokinase (i.e. providing G6P) in the mechanism of ocrelizumab reduction. Without being bound by this, or any other theory, EDTA blocks the reduction of ocrelizumab by eliminating the hexokinase activity and thereby reducing the G6P level available for G6PD, and subsequently the NADPH level available for the Trx system.

Although EDTA is every effective in blocking the reduction of ocrelizumab in fresh HCCF, it was unable to prevent the reduction of ocerlizumab in the beta run HCCF in which the Trx system activity was lost then reactivated by the addition of G6P. For example, the reduction of ocrelizumab was observed in an HCCF incubation experiment in which 5 mM G6P and 20 mM EDTA (final concentrations) were added to the beta run HCCF that had fully lost reducing activity (FIG. 18). However, no reduction was seen in the control incubation experiment in which no G6P and EDTA were added. Without being bound by this or any other theory, the EDTA used in this manner may therefore inhibit neither the Trx system nor the G6PD, and may function as an inhibitor for hexokinase, which produces the G6P for the G6PD. Without G6P, the Trx system would not be supplied with the necessary NADPH for activity.

Example 6

Inhibition of Reduction of Recombinant Antibody by DHEA

Dehydroepiandrosterone (DHEA), as well as other similar G6PD inhibitors, effectively blocks G6PD activity (Gordon et al., 1995, supra). G6PD inhibitors also prevent the reduction of an antibody in HCCF, for example, ocrelizumab, by blocking the generation of NADPH. The ability of DHEA to inhibit the reduction of orcelizumab is demonstrated in an HCCF incubation experiment. Adding DHEA to a HCCF prevents antibody reduction.

DHEA is typically used in the concentration range from about 0.05 mM to about 5 mM. DHEA is also typically used in the concentration range from about 0.1 mM to about 2.5 mM.

Example 7

Inhibition of Reduction of Recombinant Antibody by (i) EDTA, (ii) Cupric Sulfate, and (iii) Acetic Acid Additions Four different HCCFs were stored and held in the stainless steel vials. The solutions were similar in the amount of cell lysis, which were generated by diluting HCCF from homogenized CCF with HCCF from non-homogenized CCF. For example, 150 mL of the first lysed solution was mixed with 50 mL of the second solution, respectively. The four HCCF mixtures evaluated in this study contained either: (1) 20 mM EDTA, (2) 30 □M $CuSO_4$, (3) 15 mM acetic acid (pH 5.5), and (4) no chemical inhibitor was added for the control solution. The ocrelizumab antibody from all four mixtures was purified immediately (t=0 hr) using protein A chromatography and then again after 20 hr and 40 hr of storage in the stainless steel vials. Purified protein A elution pools were analyzed by the Bioanalyzer assay to quantitate the percentage of intact antibody (150 kDa). The results showed that greater than 90% intact antibody was present in all four mixtures at the initial time point (FIG. 19). However, at the 20 hr time point, intact antibody was not detected in the control mixture (without any addition) indicating reduction of the antibody disulfide bonds. In the three other mixtures, over 90% intact antibody was still detected at both 20 hr and 40 hr time points, demonstrating the prevention of disulfide bond reduction by all three inhibitors tested.

Example 8

Inhibition of Reduction of Recombinant Antibody by Air Sparging the HCCF

One HCCF mixture generated from homogenized CCF was stored and held in two separate 10 L stainless steel fermentors. One vessel was sparged with air while the other vessel was sparged with nitrogen gas. The ocrelizumab antibody was purified immediately (t=0 hr) from the initial mixture using protein A chromatography. At selected time points, 50 mL samples were removed from each vessel and the antibody was purified using protein A chromatography. Purified protein A elution pools were then analyzed by the Bioanalyzer assay to quantitate the percentage of intact antibody at 150 kDa. The results showed that approximately 85% intact antibody was present in the initial solution (FIG. 20), indicating some early reduction of the antibody disulfide bonds prior to exposure to oxygen (i.e. sparged air in the fermentor). Once the mixture was sparged with air for two hours, greater than 90% intact antibody was measured for the remainder of the 36 hr study. In contrast, when the mixture was sparged with nitrogen gas, the antibody reduction event continued as measured at 2 hr (28% 150 kDa peak) and 6 hr (5% 150 kDa peak). These results demonstrated the prevention of disulfide bond reduction in the antibody when the HCCF mixture generated from homogenized CCF was exposed to oxygen.

Example 9

Design of Targeted siRNA or Antisense Nucleotide Trx Inhibitors

The design of targeted siRNAs or antisense nucleotides to the genes as found in CHO cells may be done by using publicly available sequences such as those for *E. coli* thioredoxin TrxA (SEQ ID NO:30), *E. coli* thioredoxin reductase TrxB (SEQ ID NO:31); mouse thioredoxin 1 (SEQ ID NO: 32), mouse thioreodoxin 2 (SEQ ID NO:33), mouse thioredoxin reductase 1 (SEQ ID NO: 34), and mouse thioredoxin reductase 2 (SEQ ID NO:35). One of ordinary skill in the art can use these sequences to select sequences to design Trx inhibitors for targeting enzymes in different organisms and/or cells, such as CHO cells.

The sequence of *E. coli* Thioredoxin TrxA is:
(SEQ ID NO: 30)
```
ATG TTA CAC CAA CAA CGA AAC CAA CAC GCC AGG CTT ATT CCT GTG GAG TTA
TAT ATG AGC GAT AAA ATT ATT CAC CTG ACT GAC GAC AGT TTT GAC ACG GAT
GTA CTC AAA GCG GAC GGG GCG ATC CTC GTC GAT TTC TGG GCA GAG TGG TGC
GGT CCG TGC AAA ATG ATC GCC CCG ATT CTG GAT GAA ATC GCT GAC GAA TAT
CAG GGC AAA CTG ACC GTT GCA AAA CTG AAC ATC GAT CAA AAC CCT GGC ACT
GCG CCG AAA TAT GGC ATC CGT GGT ATC CCG ACT CTG CTG CTG TTC AAA AAC
GGT GAA GTG GCG GCA ACC AAA GTG GGT GCA CTG TCT AAA GGT CAG TTG AAA
GAG TTC CTC GAC GCT AAC CTG GCG TAA.
```

The sequence of *E. coli* Thioredoxin TrxB is:
(SEQ ID NO: 31)
```
ATG GGC ACG ACC AAA CAC AGT AAA CTG CTT ATC CTG GGT TCA GGC CCG GCG
GGA TAC ACC GCT GCT GTC TAC GCG GCG CGC GCC AAC CTG CAA CCT GTG CTG
ATT ACC GGC ATG GAA AAA GGC GGC CAA CTG ACC ACC ACC ACG GAA GTG GAA
AAC TGG CCT GGC GAT CCA AAC GAT CTG ACC GGT CCG TTA TTA ATG GAG CGC
ATG CAC GAA CAT GCC ACC AAG TTT GAA ACT GAG ATC ATT TTT GAT CAT ATC
AAC AAG GTG GAT CTG CAA AAC CGT CCG TTC CGT CTG AAT GGC GAT AAC GGC
GAA TAC ACT TGC GAC GCG CTG ATT ATT GCC ACC GGA GCT TCT GCA CGC TAT
CTC GGC CTG CCC TCT GAA GAA GCC TTT AAA GGC CGT GGG GTT TCT GCT TGT
GCA ACC TGC GAC GGT TTC TTC TAT CGC AAC CAG AAA GTT GCG GTC ATC GGC
GGC GGC AAT ACC GCG GTT GAA GAG GCG TTG TAT CTG TCT AAC ATC GCT TCG
GAA GTG CAT CTG ATT CAC CGC CGT GAC GGT TTC CGC GCG GAA AAA ATC CTC
ATT AAG CGC CTG ATG GAT AAA GTG GAG AAC GGC AAC ATC ATT CTG CAC ACC
AAC CGT ACG CTG GAA GAA GTG ACC GGC GAT CAA ATG GGT GTC ACT GGC GTT
CGT CTG CGC GAT ACG CAA AAC AGC GAT AAC ATC GAG TCA CTC GAC GTT GCC
GGT CTG TTT GTT GCT ATC GGT CAC AGC CCG AAT ACT GCG ATT TTC GAA GGG
CAG CTG GAA CTG GAA AAC GGC TAC ATC AAA GTA CAG TCG GGT ATT CAT GGT
AAT GCC ACC CAG ACC AGC ATT CCT GGC GTC TTT GCC GCA GGC GAC GTG ATG
GAT CAC ATT TAT CGC CAG GCC ATT ACT TCG GCC GGT ACA GGC TGC ATG GCA
GCA CTT GAT GCG GAA CGC TAC CTC GAT GGT TTA GCT GAC GCA AAA TAA.
```

The sequence of mouse thioredoxin 1 is:
(SEQ ID NO: 32)
```
ATGGTGAAGCTGATCGAGAGCAAGGAAGCTTTTCAGGAGGCCCTGGCCGCCGCGGGA
GACAAGCTTGTCGTGGTGGACTTCTCTGCTACGTGGTGTGGACCTTGCAAAATGATCA
AGCCCTTCTTCCATTCCCTCTGTGACAAGTATTCCAATGTGGTGTTCCTTGAAGTGGAT
GTGGATGACTGCCAGGATGTTGCTGCAGACTGTGAAGTCAAATGCATGCCGACCTTCC
```

AGTTTTATAAAAAGGGTCAAAAGGTGGGGGAGTTCTCCGGTGCTAACAAGGAAAAGC

TTGAAGCCTCTATTACTGAATATGCCTAA.

The sequence of mouse thioreodoxin 2 is:
(SEQ ID NO: 33)
ATGGCTCAGCGGCTCCTCCTGGGGAGGTTCCTGACCTCAGTCATCTCCAGGAAGCCTC

CTCAGGGTGTGTGGGCTTCCCTCACCTCTAAGACCCTGCAGACCCCTCAGTACAATGCT

GGTGGTCTAACAGTAATGCCCAGCCCAGCCCGGACAGTACACACCACCAGAGTCTGTT

TGACGACCTTTAACGTCCAGGATGGACCTGACTTTCAAGACAGAGTTGTCAACAGTGA

GACACCAGTTGTTGTGGACTTTCATGCACAGTGGTGTGGCCCCTGCAAGATCCTAGGA

CCGCGGCTAGAGAAGATGGTCGCCAAGCAGCACGGGAAGGTGGTCATGGCCAAAGTG

GACATTGACGATCACACAGACCTTGCCATTGAATATGAGGTGTCAGCTGTGCCTACCG

TGCTAGCCATCAAGAACGGGGACGTGGTGGACAAGTTTGTGGGGATCAAGGACGAGG

ACCAGCTAGAAGCCTTCCTGAAGAAGCTGATTGGCTGA.

The sequence of mouse thioredoxin reductase 1 is:
(SEQ ID NO: 34)
ATGAATGGCTCCAAAGATCCCCCTGGGTCCTATGACTTCGACCTGATCATCATTGGAG

GAGGCTCAGGAGGACTGGCAGCAGCTAAGGAGGCAGCCAAATTTGACAAGAAAGTGC

TGGTCTTGGATTTTGTCACACCGACTCCTCTTGGGACCAGATGGGGTCTCGGAGGAAC

GTGTGTGAATGTGGGTTGCATACCTAAGAAGCTGATGCACCAGGCAGCTTTGCTCGGA

CAAGCTCTGAAAGACTCGCGCAACTATGGCTGGAAAGTCGAAGACACAGTGAAGCAT

GACTGGGAGAAAATGACGGAATCTGTGCAGAGTCACATCGGCTCGCTGAACTGGGGC

TACCGCGTAGCTCTCCGGGAGAAAAAGGTCGTCTATGAGAATGCTTACGGGAGGTTCA

TTGGTCCTCACAGGATTGTGGCGACAAATAACAAAGGTAAAGAAAAAATCTATTCAGC

AGAGCGTTCCTCATCGCCACAGGTGAGAGGCCCCGCTACCTGGGCATCCCTGGAGAC

AAAGAGTACTGCATCAGCAGTGATGATCTTTTCTCCTTGCCTTACTGCCCGGGGAAGA

CCCTAGTAGTTGGTGCATCCTATGTCGCCTTGGAATGTGCAGGATTTCTGGCTGGTATC

GGCTTAGACGTCACTGTAATGGTGCGGTCCATTCTCCTTAGAGGATTTGACCAAGACA

TGGCCAACAAAATCGGTGAACACATGGAAGAACATGGTATCAAGTTTATAAGGCAGTT

CGTCCCAACGAAAATTGAACAGATCGAAGCAGGAACACCAGGCCGACTCAGGGTGAC

TGCTCAATCCACAAACAGCGAGGAGACCATAGAGGGCGAATTTAACACAGTGTTGCTG

GCGGTAGGAAGAGATTCTTGTACGAGAACTATTGGCTTAGAGACCGTGGGCGTGAAG

ATAAACGAAAAAACCGGAAAGATACCCGTCACGGATGAAGAGCAGACCAATGTGCCT

TACATCTACGCCATCGGTGACATCCTGGAGGGGAAGCTAGAGCTGACTCCCGTAGCCA

TCCAGGCGGGAGATTGCTGGCTCAGAGGCTGTATGGAGGCTCCAATGTCAAATGTGA

CTATGACAATGTCCCAACGACTGTATTTACTCCTTTGGAATATGGCTGTTGTGGCCTCT

CTGAAGAAAAGCCGTAGAGAAATTTGGGGAAGAAAATATTGAAGTTTACCATAGTTT

CTTTTGGCCATTGGAATGGACAGTCCCATCCCGGGATAACAACAAATGTTATGCAAAA

ATAATCTGCAACCTTAAAGACGATGAACGTGTCGTGGGCTTCCACGTGCTGGGTCCAA

ACGCTGGAGAGGTGACGCAGGGCTTTGCGGCTGCGCTCAAGTGTGGGCTGACTAAGCA

GCAGCTGGACAGCACCATCGGCATCCACCCGGTCTGTGCAGAGATATTCACAACGTTG

TCAGTGACGAAGCGCTCTGGGGGAGACATCCTCCAGTCTGGCTGCTGA

-continued

The sequence of mouse thioredoxin reductase 2 is:
(SEQ ID NO: 35)
ATGGCGGCGATGGTGGCGGCGATGGTGGCGGCGCTGCGTGGACCCAGCAGGCGCTTC

CGGCCGCGGACACGGGCTCTGACACGCGGGACAAGGGGCGCGGCGAGTGCAGCGGGA

GGGCAGCAGAGCTTTGATCTCTTGGTGATCGGTGGGGATCCGGTGGCCTAGCTTGTG

CCAAGGAAGCTGCTCAGCTGGGAAGAAGGTGGCTGTGGCTGACTATGTGGAACCTTC

TCCCCGAGGCACCAAGTGGGGCCTTGGTGGCACCTGTGTCAACGTGGGTTGCATACCC

AAGAAGCTGATGCATCAGGCTGCACTGCTGGGGGCATGATCAGAGATGCTCACCACT

ATGGCTGGGAGGTGGCCCAGCCTGTCCAACACAACTGGAAGACAATGGCAGAAGCCG

TGCAAAACCATGTGAAATCCTTGAACTGGGTCATCGCGTCCAACTGCAGGACAGGAA

AGTCAAGTACTTTAACATCAAAGCCAGCTTTGTGGATGAGCACACAGTTCGCGGTGTG

GACAAAGGCGGGAAGGCGACTCTGCTTTCAGCTGAGCACATTGTCATTGCTACAGGAG

GACGGCCAAGGTACCCCACACAAGTCAAAGGAGCCCTGGAATATGGAATCACAAGTG

ACGACATCTTCTGGCTGAAGGAGTCCCCTGGGAAAACGTTGGTGGTTGGAGCCAGCTA

TGTGGCCCTAGAGTGTGCTGGCTTCCTCACTGGAATTGGACTGGATACCACTGTCATGA

TGCGCAGCATCCCTCTCCGAGGCTTTGACCAGCAAATGTCATCTTTGGTCACAGAGCA

CATGGAGTCTCATGGCACCCAGTTCCTGAAAGGCTGTGTCCCCTCCCACATCAAAAAA

CTCCCAACTAACCAGCTGCAGGTCACTTGGGAGGATCATGCTTCTGGCAAGGAAGACA

CAGGCACCTTTGACACTGTCCTGTGGGCCATAGGGCGAGTTCCAGAAACCAGGACTTT

GAATCTGGAGAAGGCTGGCATCAGTACCAACCCTAAGAATCAGAAGATTATTGTGGAT

GCCCAGGAGGCTACCTCTGTTCCCCACATCTATGCCATTGGAGATGTTGCTGAGGGGC

GGCCTGAGCTGACGCCCACAGCTATCAAGGCAGGAAAGCTTCTGGCTCAGCGGCTCTT

TGGGAAATCCTCAACCTTAATGGATTACAGCAATGTTCCCACAACTGTCTTTACACCAC

TGGAGTATGGCTGTGTGGGGCTGTCTGAGGAGGAGGCTGTGGCTCTCCATGGCCAGGA

GCATGTAGAGGTTTACCATGCATATTATAAGCCCCTAGAGTTCACGGTGGCGGATAGG

GATGCATCACAGTGCTACATAAAGATGGTATGCATGAGGGAGCCCCCACAACTGGTGC

TGGGCCTGCACTTCCTTGGCCCCAACGCTGGAGAAGTCACCCAAGGATTTGCTCTTGG

GATCAAGTGTGGGGCTTCATATGCACAGGTGATGCAGACAGTAGGGATCCATCCCACC

TGCTCTGAGGAGGTGGTCAAGCTGCACATCTCCAAGCGCTCCGGCCTGGAGCCTACTG

TGACTGGTTGCTGA.

Example 10

In Vitro Trx/Trx Reductase Studies

Materials and Methods

A commercial TrxR (rat liver) solution (4 μM) was diluted with water to yield a 2.86 μM solution. Lyophilized Trx (human) was reconstituted with PBS (10 mM, pH 7.2) yielding a 500 μM solution. A solution of 20 mM NADPH and 10 mM ATG and ATM solutions were prepared in water.

In a black polypropylene 1.5 mL micro centrifuge tube, 437 μL reaction buffer (10 mM histidine, 10 mM Na2SO4, 137 mM NaCl, 2.5 mM KCl, pH 7.0), 25 μL NADPH, 16 UL formulated ocrelizumab solution (30.2 mg/mL) and 5 UL Trx were gently mixed. The reaction was initiated by the addition of 17.5 μL TrxR. The reaction was incubated at room temperature for 24 hours. Aliquots of 20 μL were taken at each sampling time-point and stored at −70° C. until analyzed by the Bioanalyzer assay.

Inhibition of the Trx system was demonstrated using the same reaction conditions described above with the addition of various inhibitors.

1. In Vitro Activity of Thioredoxin System

Figure 24:
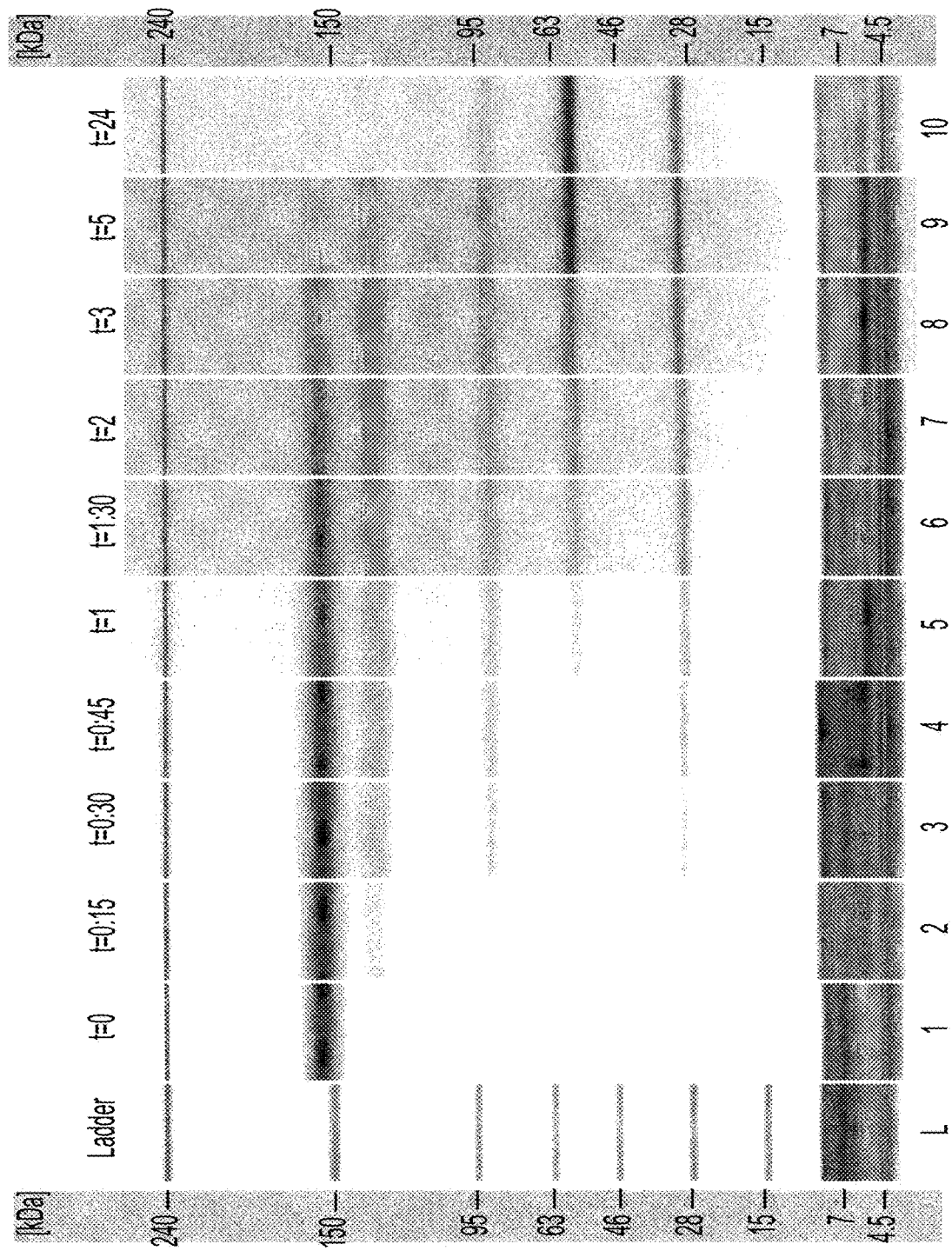
FIG. 24 is a digital gel-like image from Bioanalyzer analysis: 2H7 (Variant A)+1 mM NADPH+5 µM thioredoxin+0.1 µM thioredoxin reductase (recombinant) in 10 mM histidine sulfate.

FIG. 24 shows a digital gel-like image from Bioanalyzer analysis (each lane representing a time point) showing that incubation of intact ocrelizumab ("2H7," a humanized anti-CD20 antibody, referred to as "Variant A" above) (1 mg/mL) with 0.1 μM TrxR (rat liver), 5 μM Trx (human) and 1 mM NADPH in 10 mM histidine sulfate buffer results in the reduction of ocrelizumab in

2. In Vitro Activity of Thioredoxin System Inhibited by Aurothioglucose

Aurothioglucose (ATG) was added to the ocrelizumab mixture described above, at the following concentrations: 1 mM; 0.6 µM (6:1 ATG:TrxR); 0.4 µM (4:1 ATG:TrxR); and 0.2 µM (2:1 ATG:TrxR).

Figure 25:
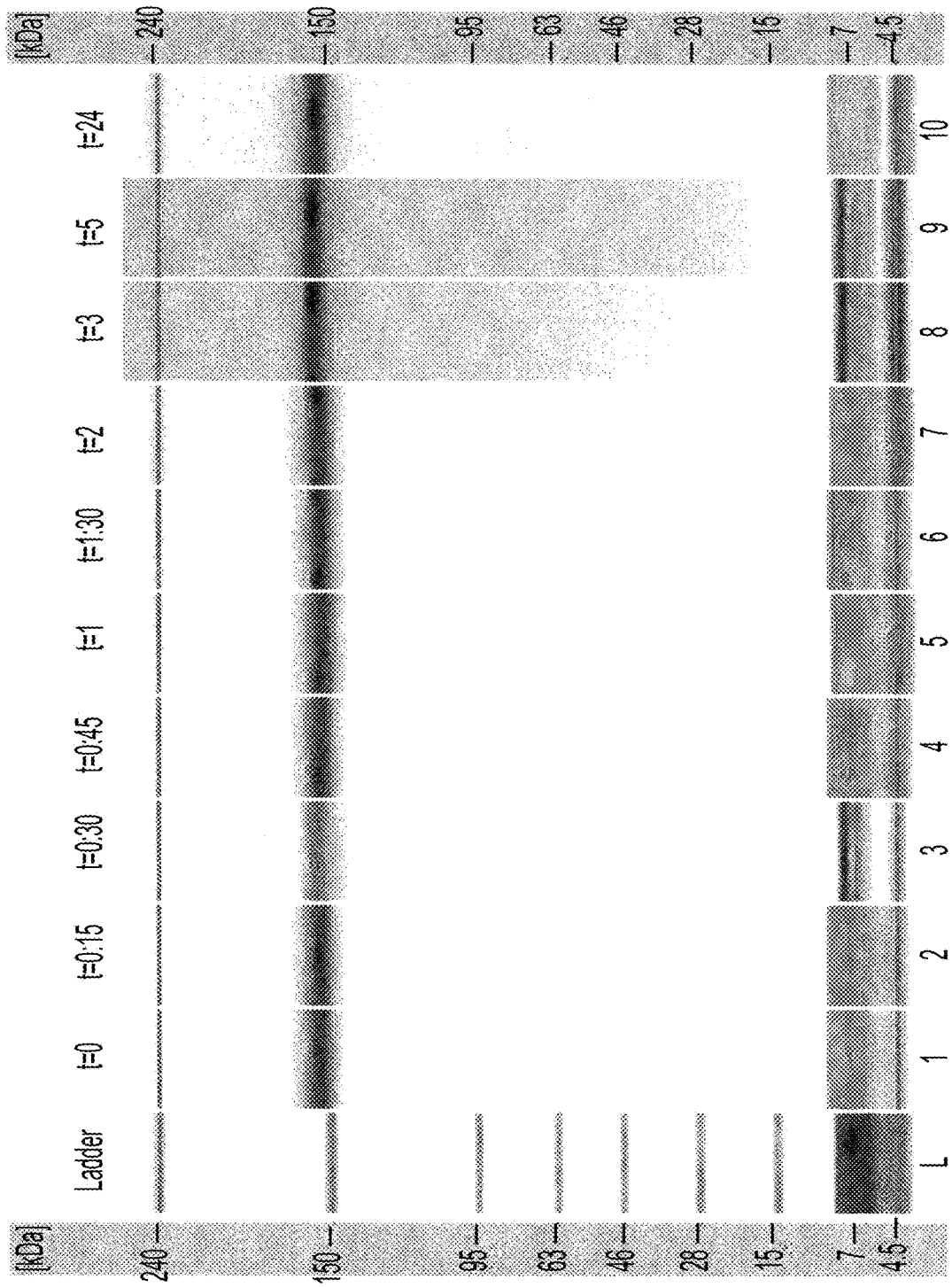
FIG. 25 is a digital gel-like image from Bioanalyzer analysis: 2H7 (Variant A)+1 mM NADPH+5 µM thioredoxin+0.1 µM thioredoxin reductase (recombinant) in 1 mM histidine sulfate+1 mM ATG.
Figure 26:
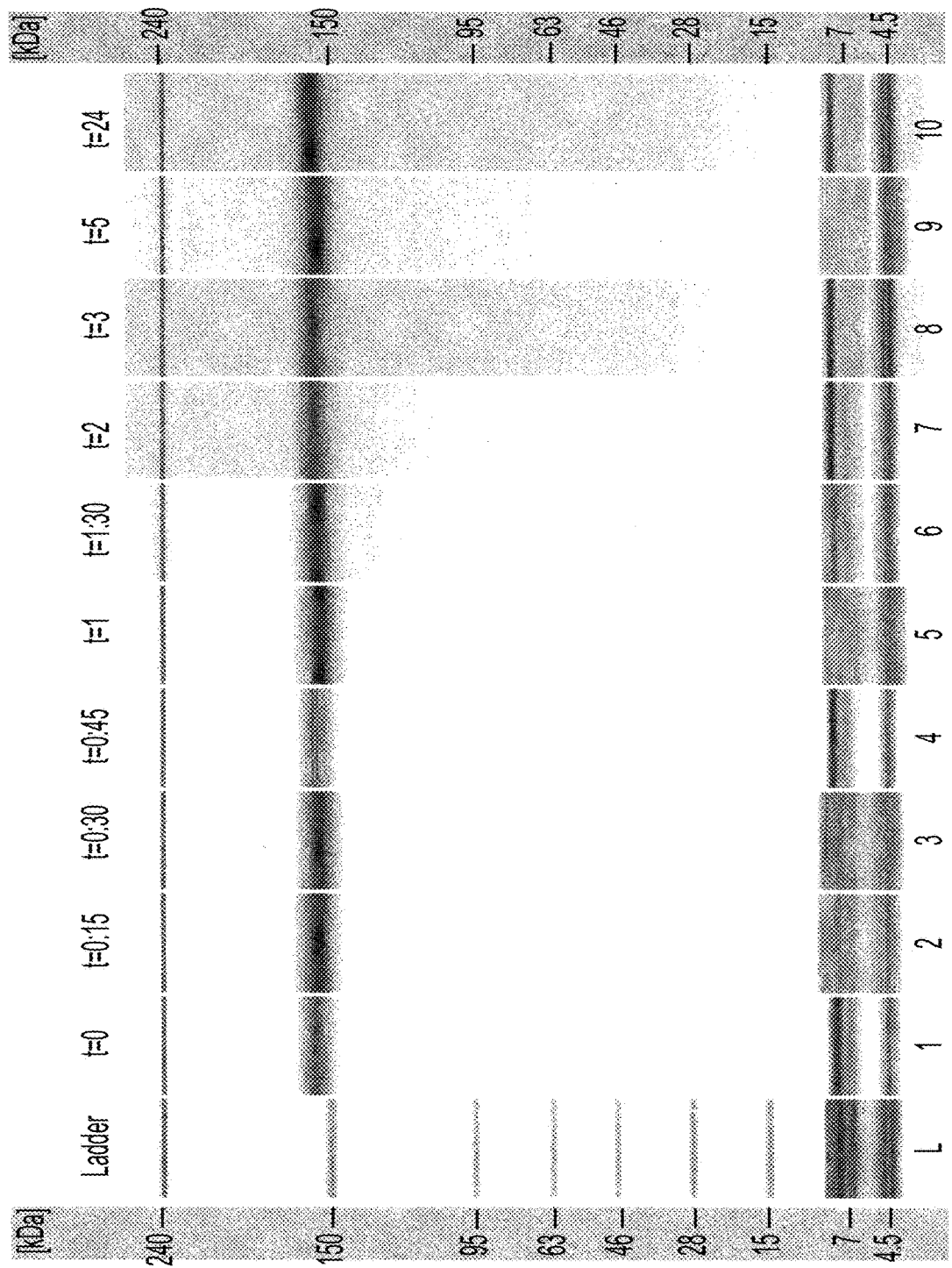
FIG. 26 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+0.6 µM ATG (6:1 ATG:TrxR).
Figure 27:
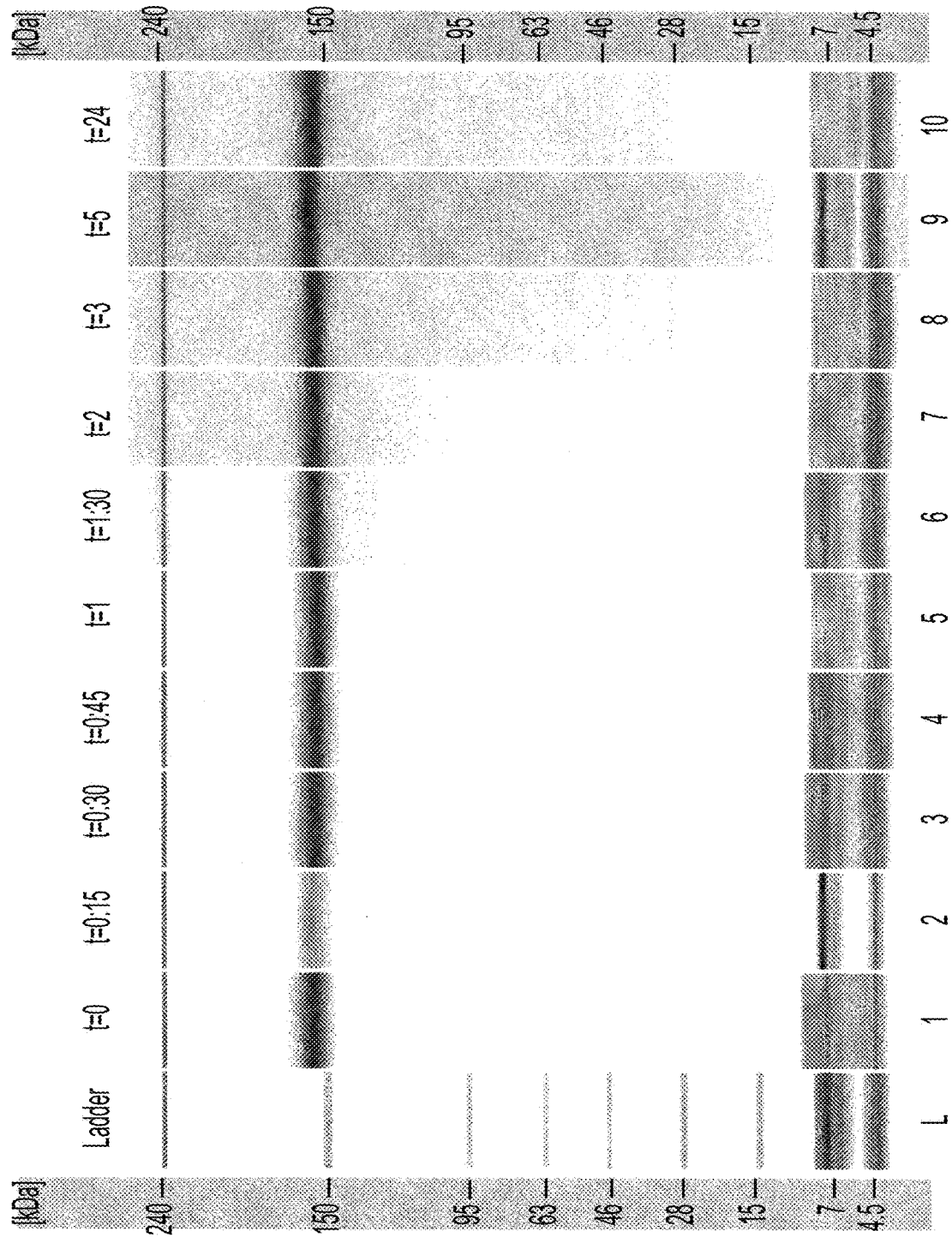
FIG. 27 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+0.4 µM ATG (4:1 ATG:TrxR).
Figure 28:
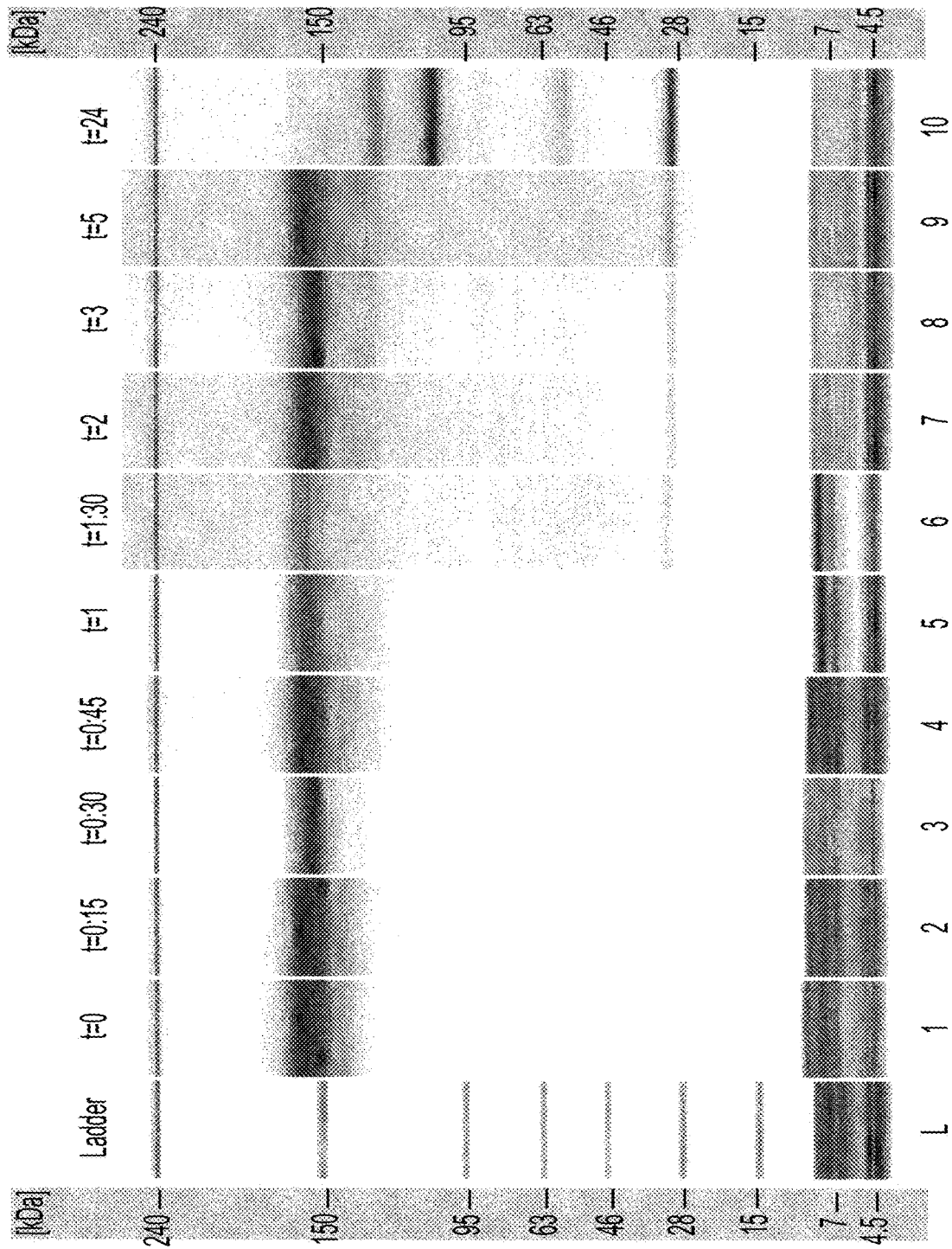
FIG. 28 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+0.2 µM ATG (2:1 ATG:TrxR).

As attested by the digital gel-like images from Bioanalyzer analysis shown in FIGS. 25-27, aurothioglucose added at concentrations 1 mM, 0.6 µM, and 0.4 µM effectively inhibits the reduction of ocrelizumab by the thioredoxin system. However, as shown in FIG. 28, under these experimental conditions aurothioglucose added at a concentration of 0.2 µM cannot inhibit ocrelizumab reduction after 24 hours.

3. In Vitro Activity of Thioredoxin System Inhibited by Aurothiomalate

Figure 29:
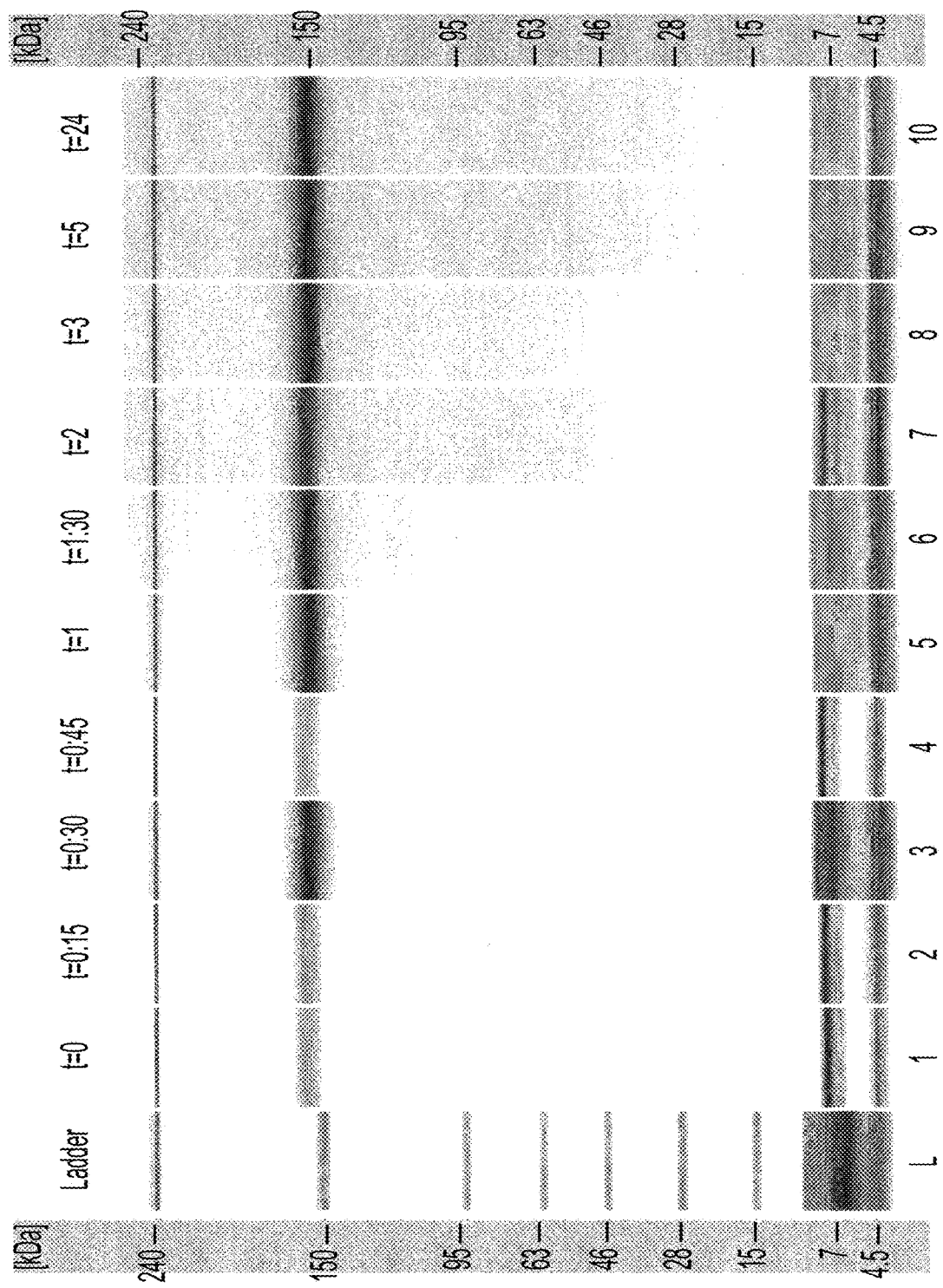
FIG. 29 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+0.1 mM autothiomalate (ATM).
Figure 30:
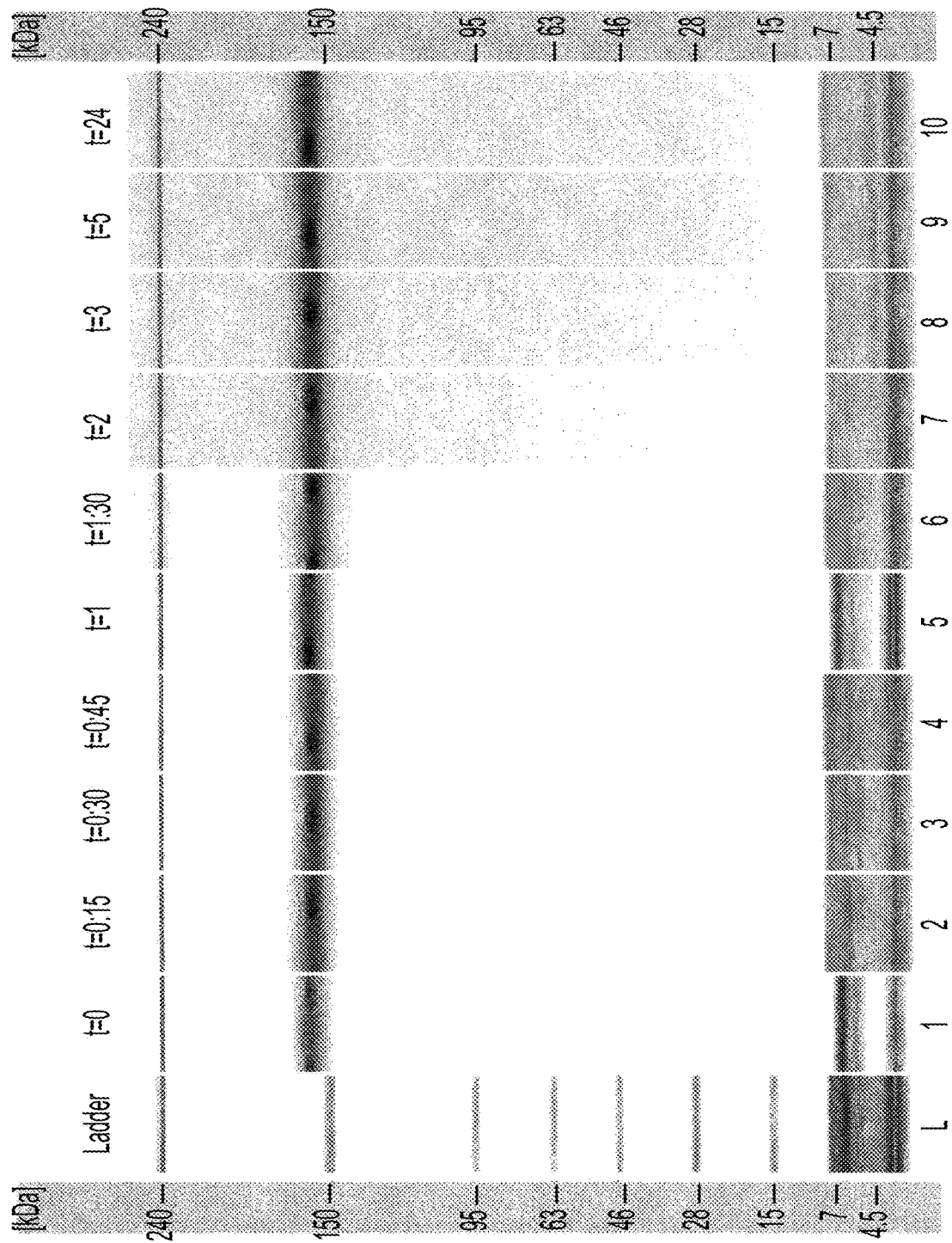
FIG. 30 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+0.01 mM autothiomalate (ATM).

Aurothiomalate (ATM) was added to the ocrelizumab mixture described above, at concentrations of 0.1 mM and 0.01 mM. As attested by the digital gel-like images from Bioanalyzer analysis shown in FIGS. 29 and 30, ATM effectively inhibits the reduction of ocrelizumab by the thioredoxin system at both concentrations tested.

Figure 31:
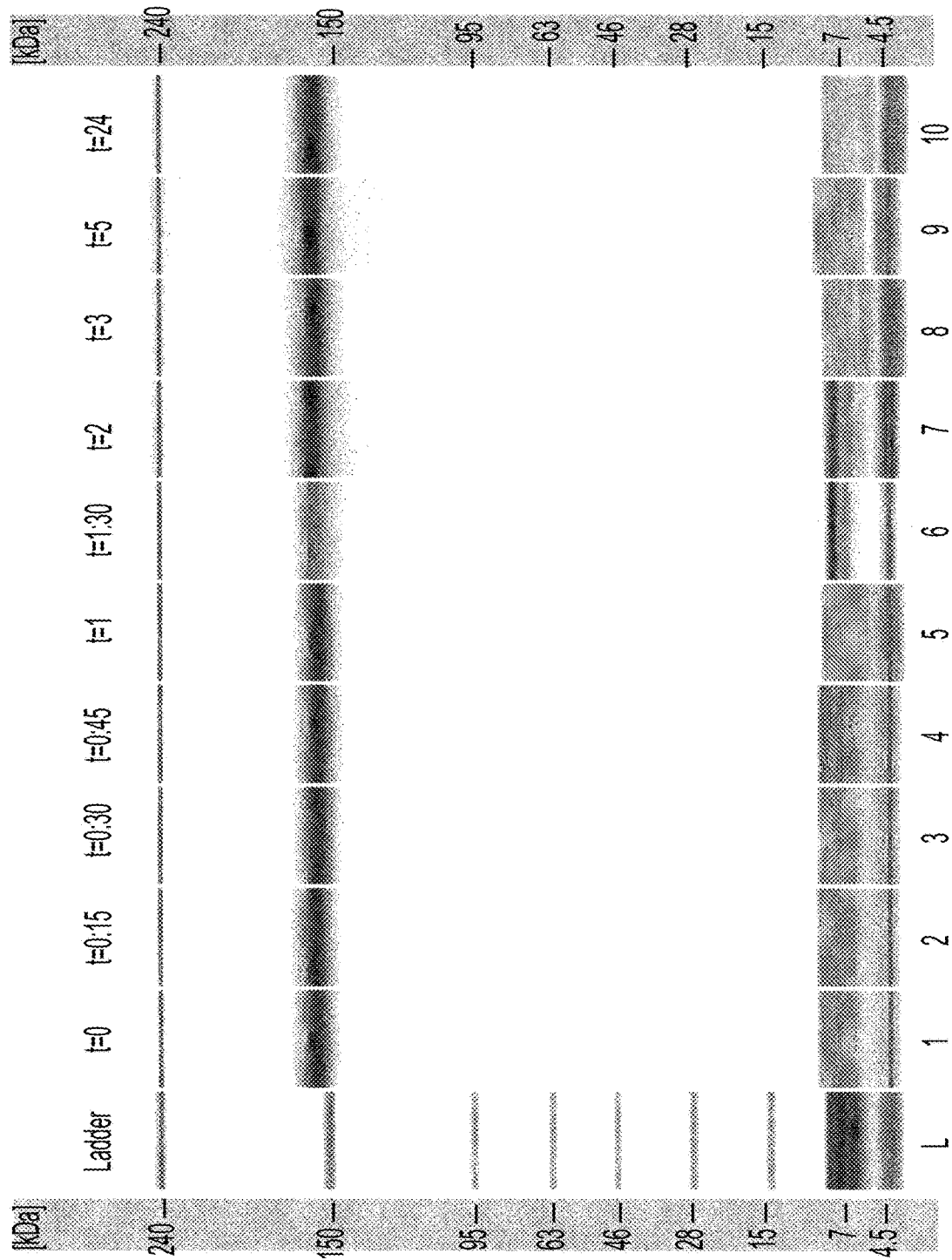
FIG. 31 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+20 µM $CuSO_4$ (4:1 $Cu^{2+}$:Trx).
Figure 32:
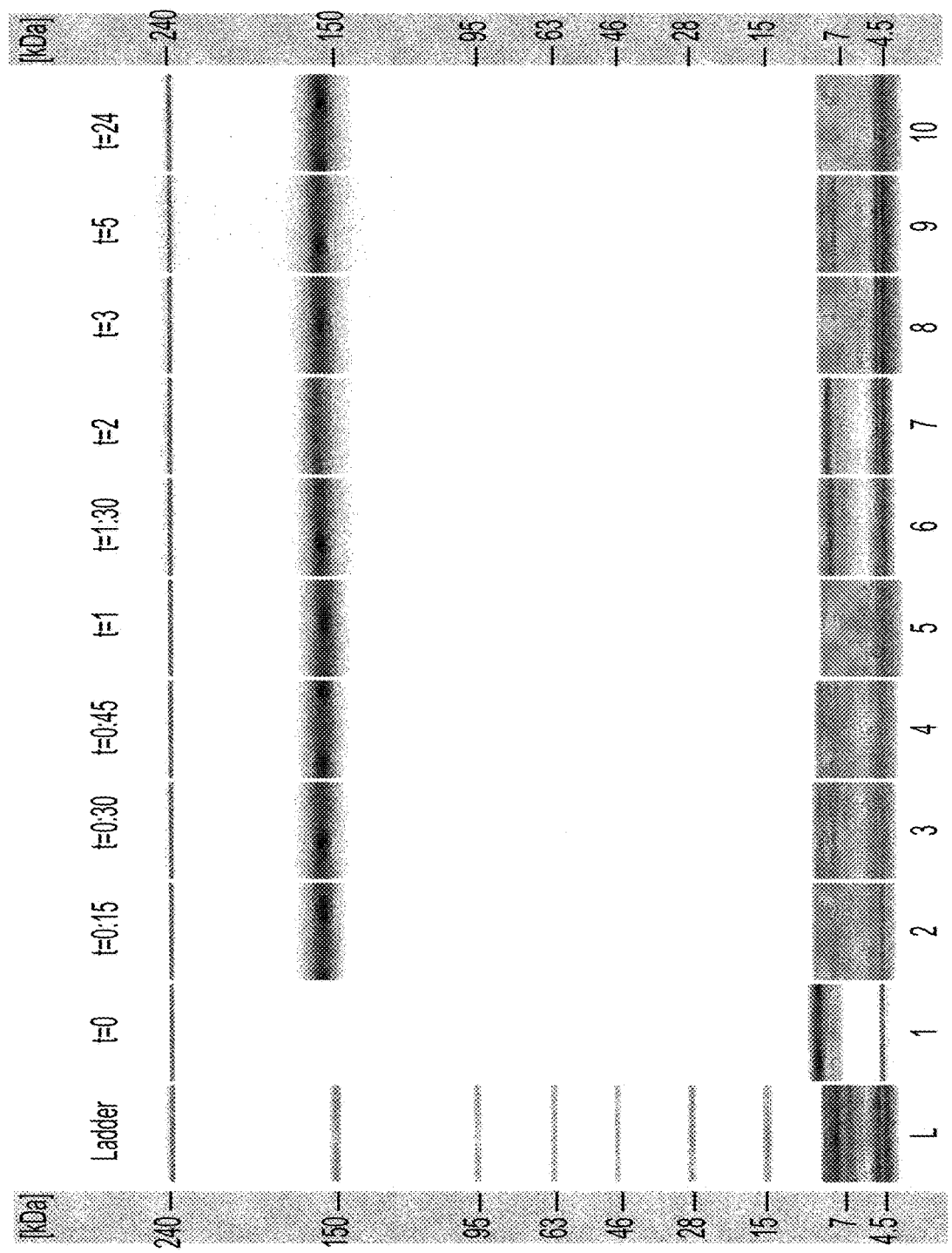
FIG. 32 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+10 µM $CuSO_4$ (2:1 $Cu^{2+}$:Trx).
Figure 33:
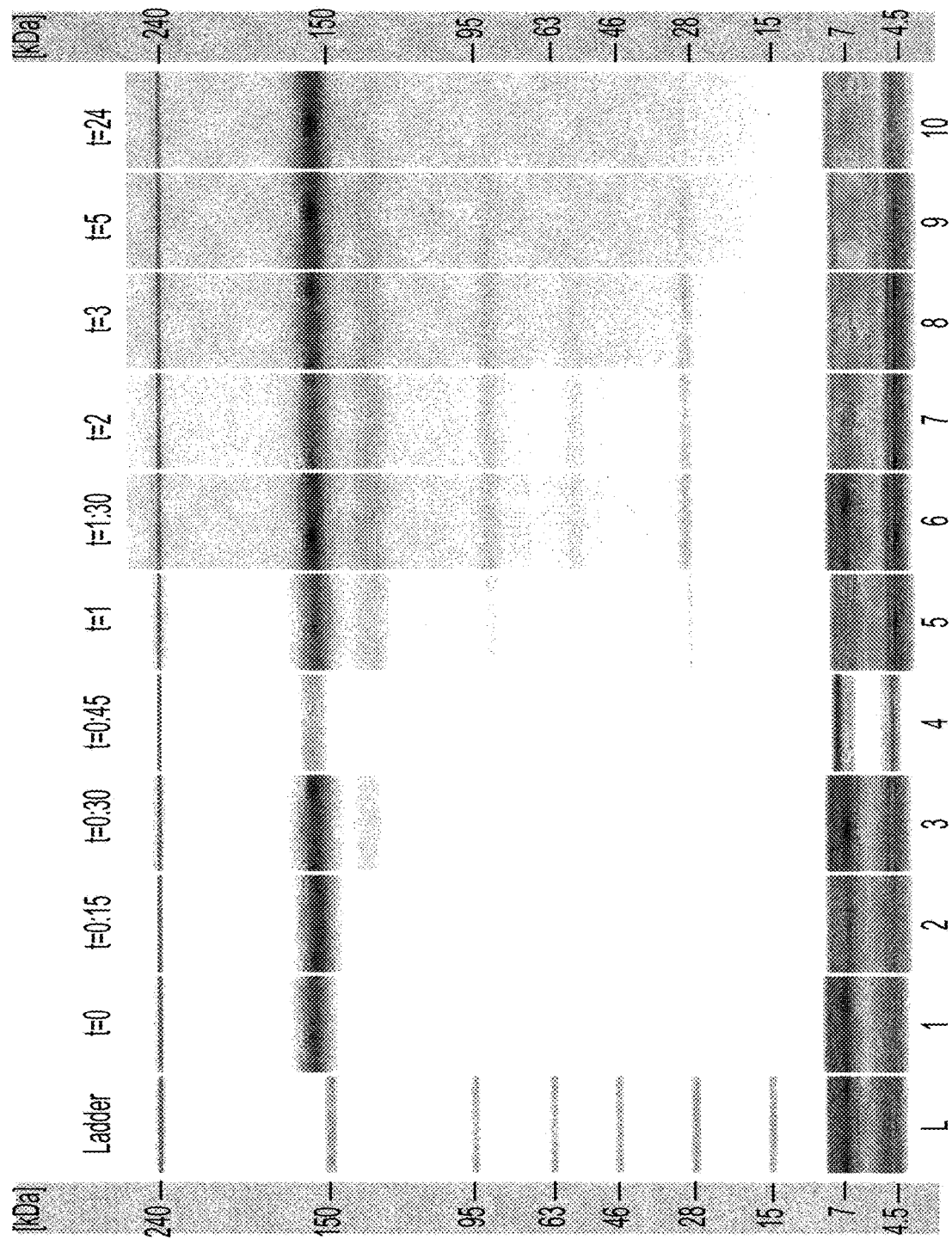
FIG. 33 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+5 µM $CuSO_4$ (1:1 $Cu^{2+}$:Trx).
Figure 34:
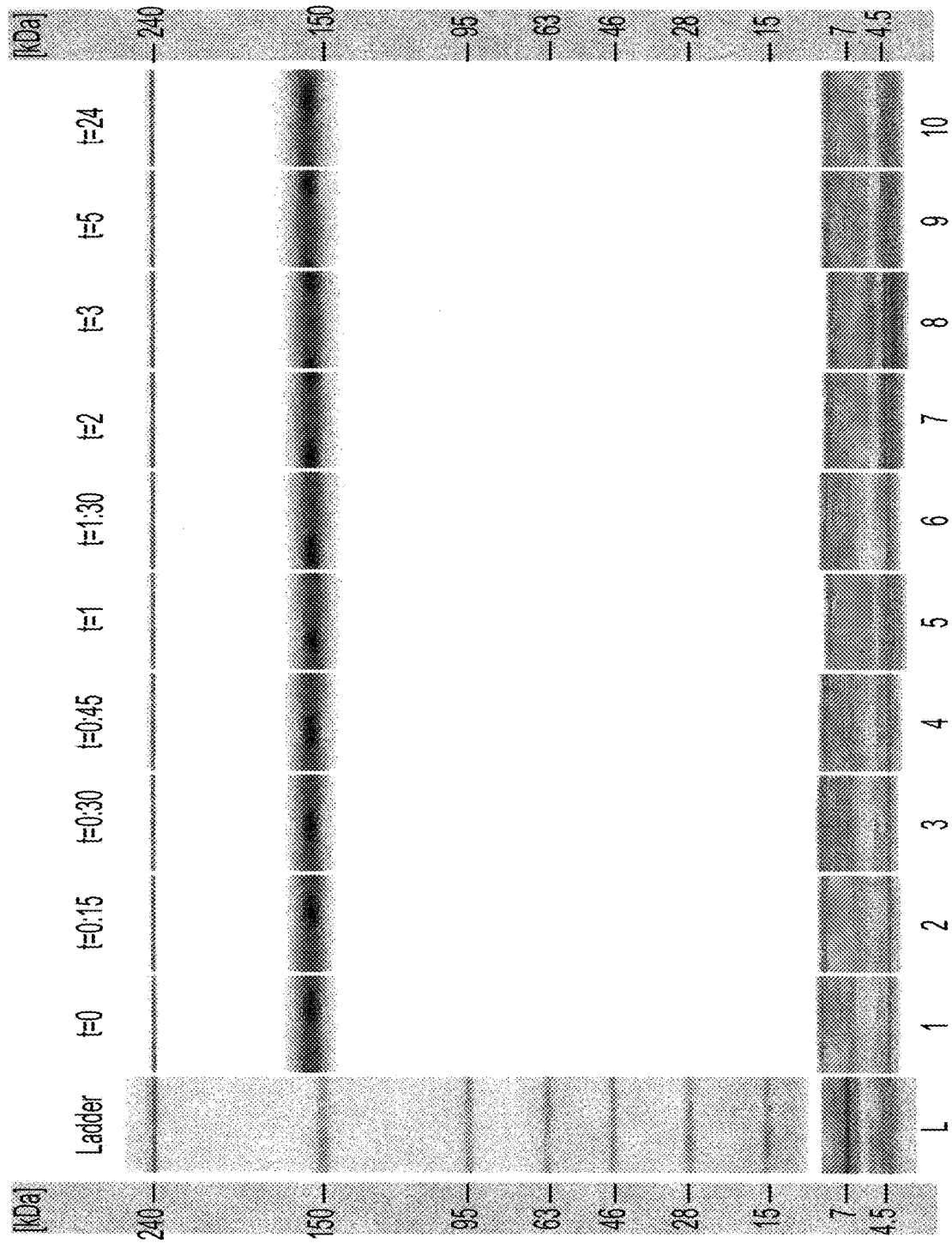
FIG. 34 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+532 µM cystamine (20:1 cystamine:2H7 disulfide).
Figure 35:
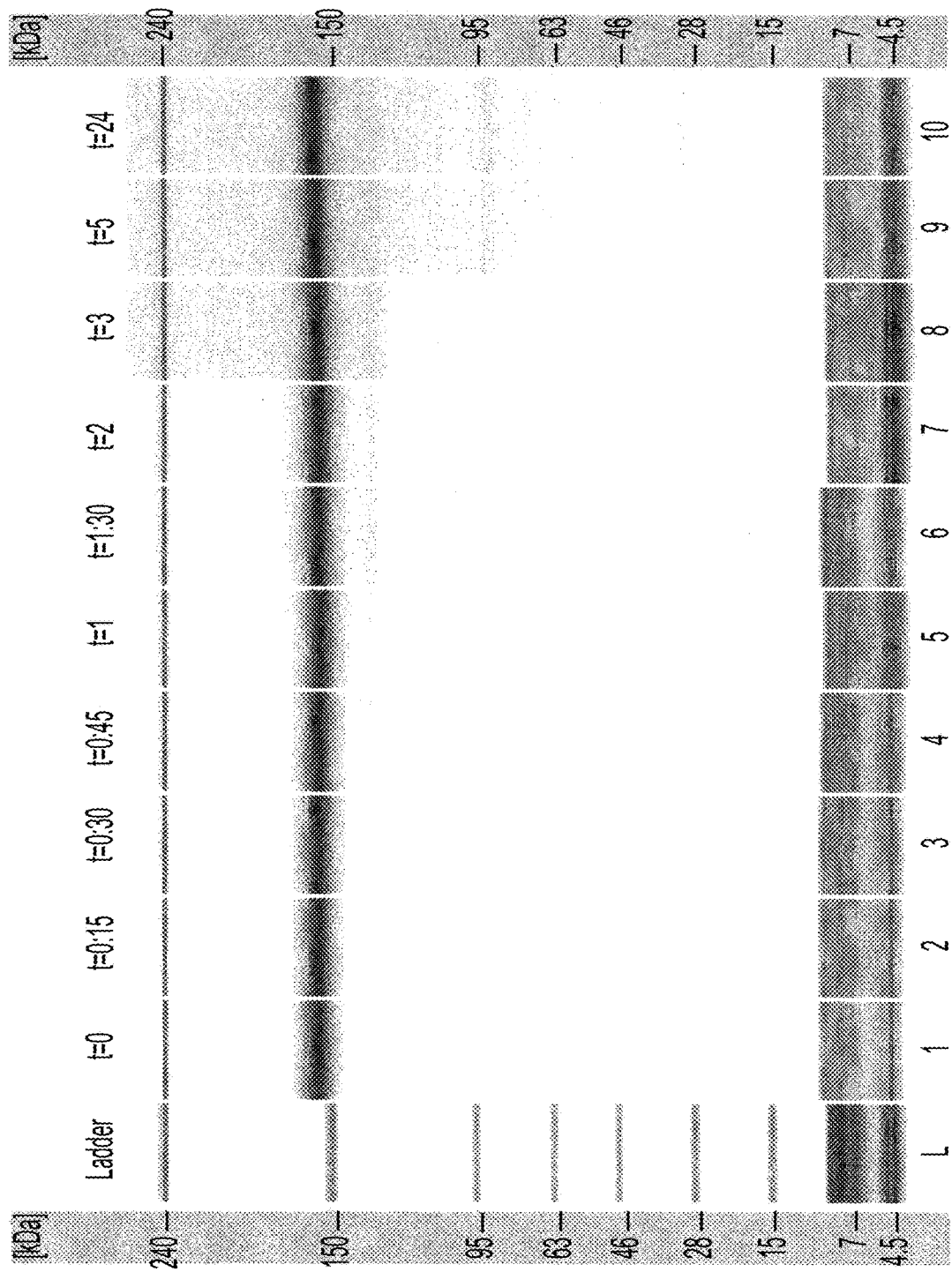
FIG. 35 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+266 µM cystamine (10:1 cystamine:2H7 disulfide).

4. In Vitro Activity of Thioredoxin System Inhibited by $CuSO_4$ $CuSO_4$ was added to the ocrelizumab mixture described above, at concentrations of 20 µM (4:1 $Cu^{2+}$:Trx); 10 µm (2:1 $Cu^{2+}$:Trx); and 5 µM (1:1 $Cu^{2+}$:Trx). As shown in FIGS. 31-33, $CuSO_4$ effectively inhibits thioredoxin-induced reduction of ocrelizumab at concentrations of 20 µM and 10 µM (FIGS. 31 and 32), but the 5 µM concentration is insufficient to result in a complete inhibition of reduction (FIG. 33).

5. In Vitro Activity of Thioredoxin System Inhibited by Cystamine

Figure 36:
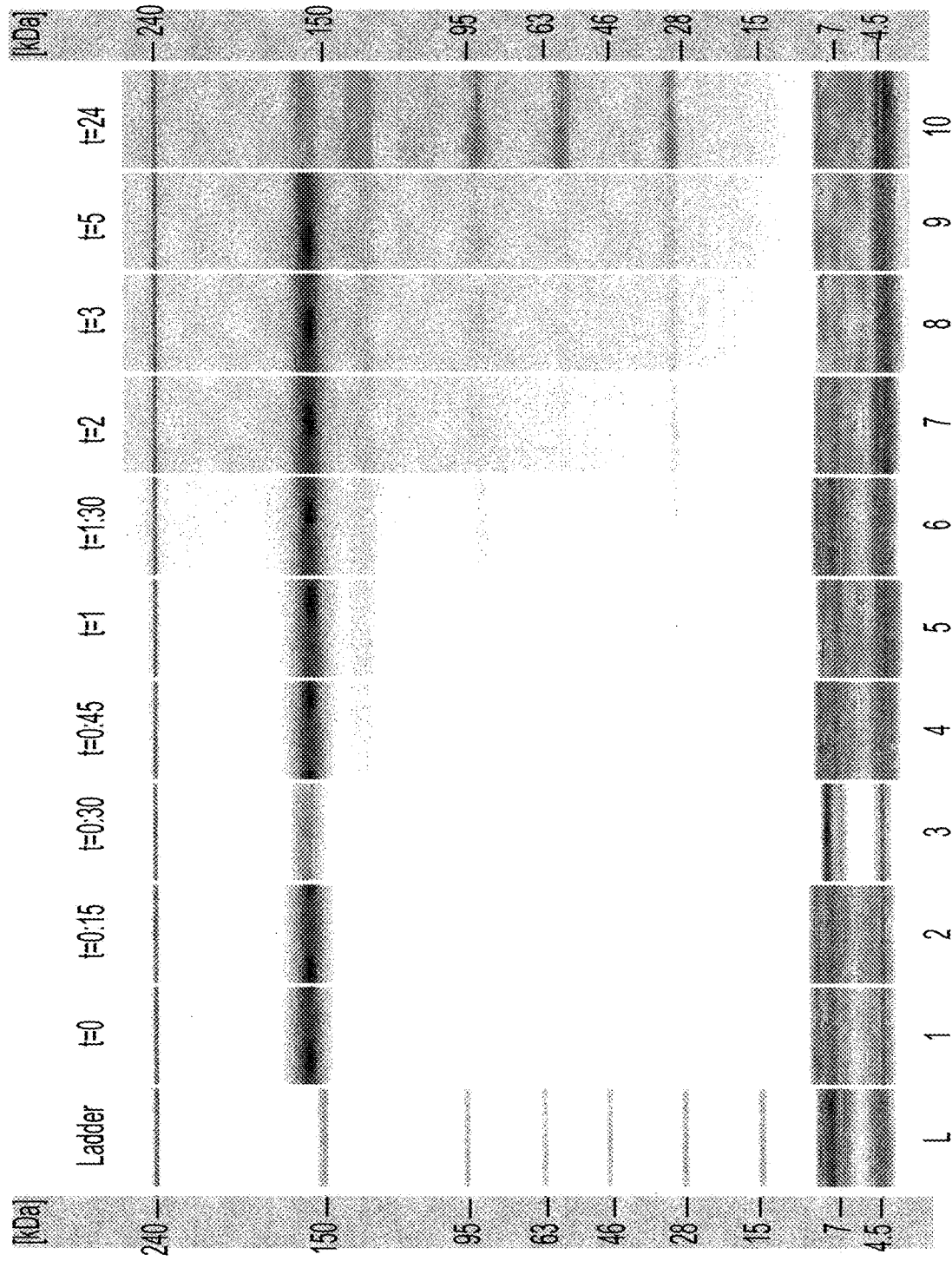
FIG. 36 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+133 µM cystamine (5:1 cystamine:2H7 disulfide).
Figure 37:
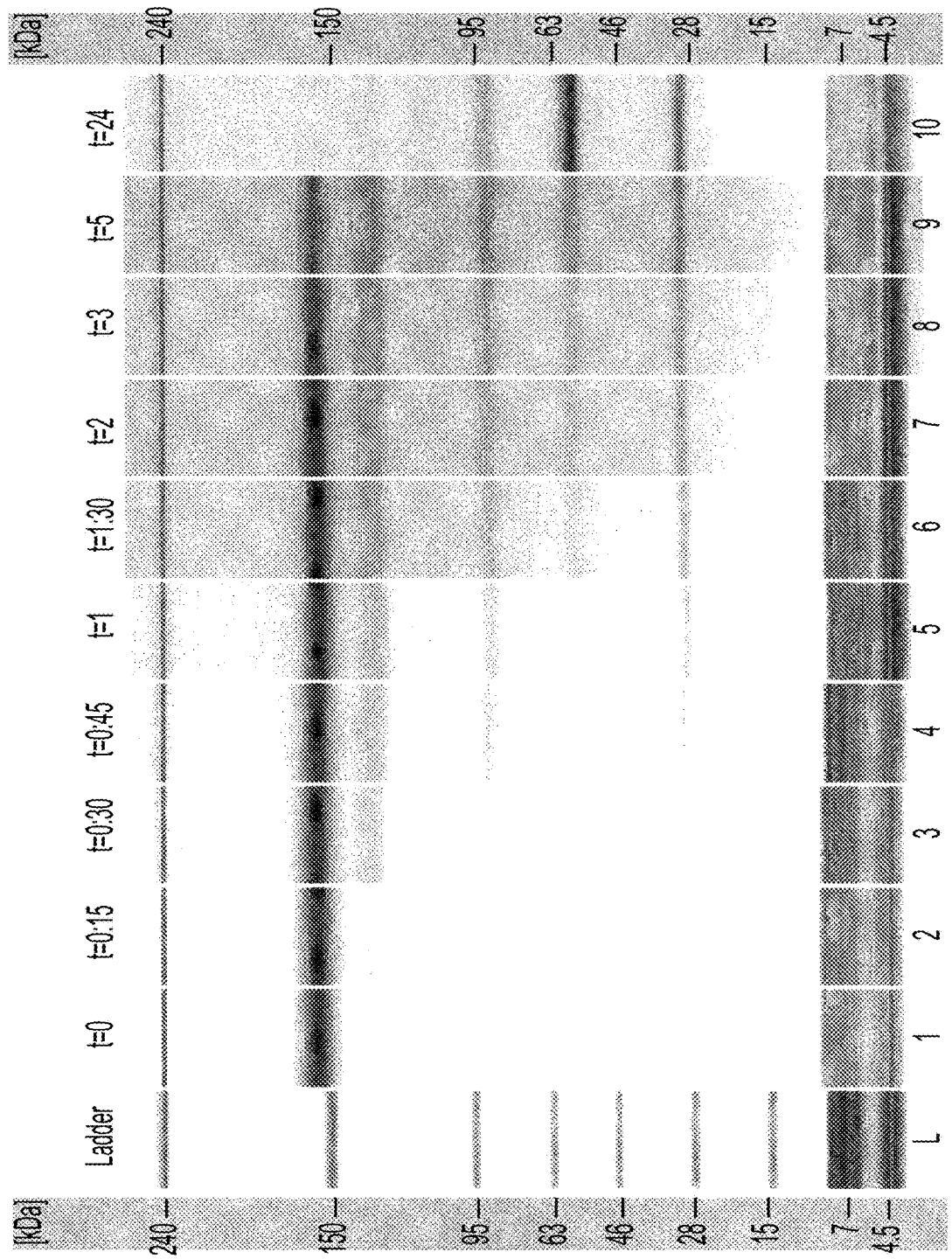
FIG. 37 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+26.6 µM cystamine (1:1 cystamine:2H7 disulfide).

Cystamine was added to the ocrelizumab mixture describe above at the following concentrations: 532 µM (20:1 cystamine:2H7 (Variant A) disulfide); 266 µM (10:1 cystamine:2H7 (Variant A) disulfide); 133 µM (5:1 cystamine:2H7 disulfide); and 26.6 µM (1:1 cystamine:2H7 (Variant A) disulfide). As shown in FIGS. 34-37, cystamine effectively inhibits thioredoxin-induced reduction of ocrelizumab at concentrations of 532 µM (20:1 cystamine:2H7 (Variant A) disulfide) and 266 µM (10:1 cystamine:2H7 (Variant A)) (FIGS. 34 and 35) but the 133 µM (5:1 cystamine:2H7 (Variant A) disulfide) and 26.6 µM (1:1 cystamine:2H7 (Variant A) disulfide) concentrations are insufficient to inhibit the reduction of ocrelizumab after 24 hours (FIGS. 36 and 37).

6. In Vitro Activity of Thioredoxin System Inhibited by Cystine

Figure 38:
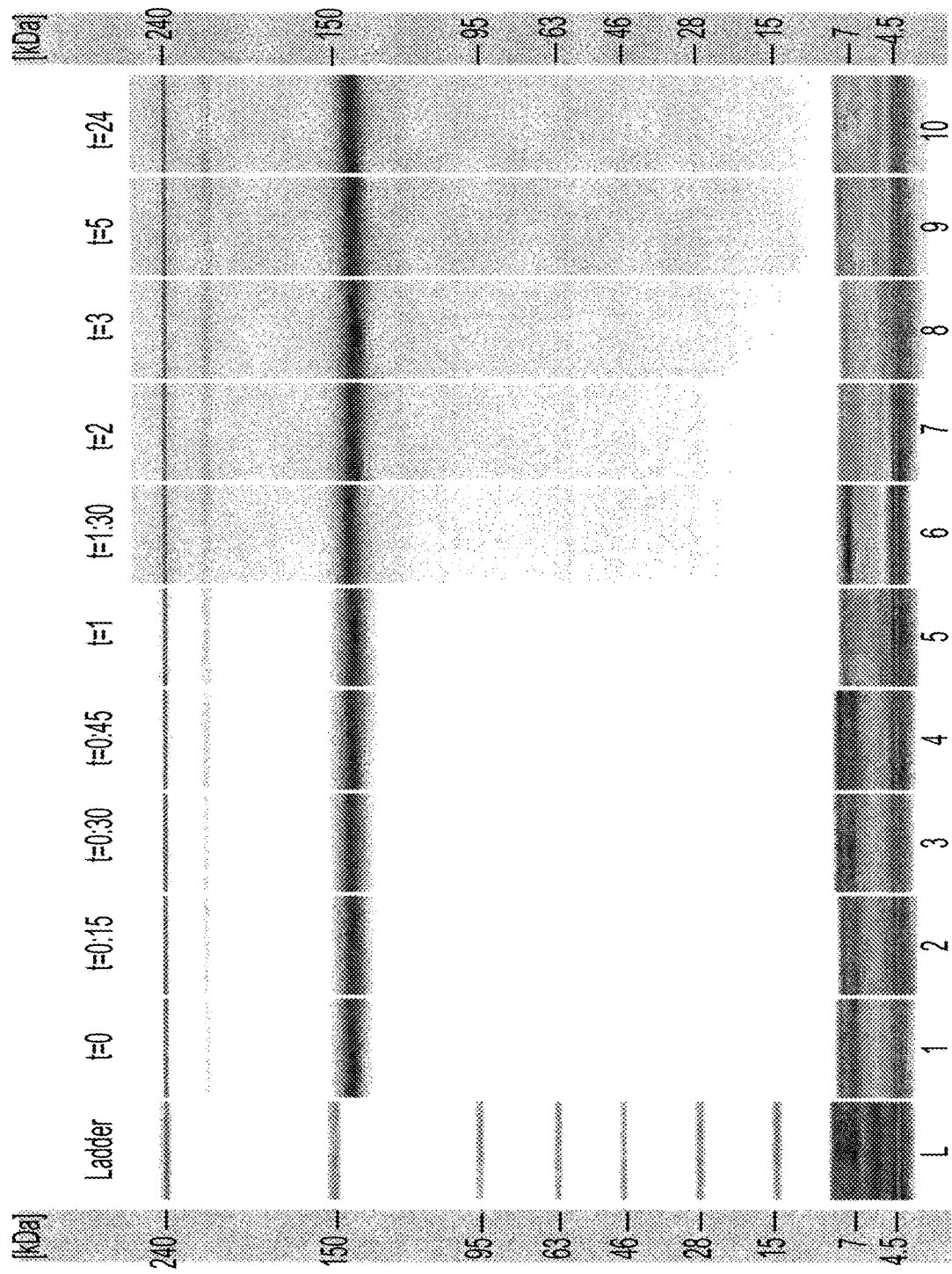
FIG. 38 is a digital gel-like image from Bioanalyzer analysis: 2H7 (Variant A)+1 mM NADPH+5 µM thioredoxin+0.1 µM thioredoxin reductase (recombinant) in 10 mM histidine sulfate (pH=7.6)+2.6 mM cystine.

Cystine was added to the ocrelizumab mixture described above at a concentration of 2.6 mM. As shown in FIG. 38, at this concentration cystine effectively inhibits reduction of ocrelizumab by the thioredoxin system. It is noted that the minimum effective concentration of cystine (just as the effective minimum concentration of other inhibitors) depends on the actual circumstances, and might be different for different proteins, such as antibodies, and might vary depending on the timing of addition. Thus, for example, if cystine is added pre-lysis, the minimum effective concentration for antibody 2H7 (Variant A) is about 1.3 mM, for Apomab about 1 mM and for antibody Variant C about 4.5 mM. When cystine is added in the cell culture medium, the minimum effective concentration typically is somewhat higher, and is about 5.2 mM for 2H7 (Variant A), 6 mM for Apomab and 9 mM for antibody Variant C. Usually, for cystine, cystamine and oxidized glutathione (see below) the minimum effective inhibitory concentration is about 40× of the antibody concentration (in µM).

7. In Vitro Activity of Thioredoxin System Inhibited by Oxidized Glutathione (GSSG)

Figure 39:
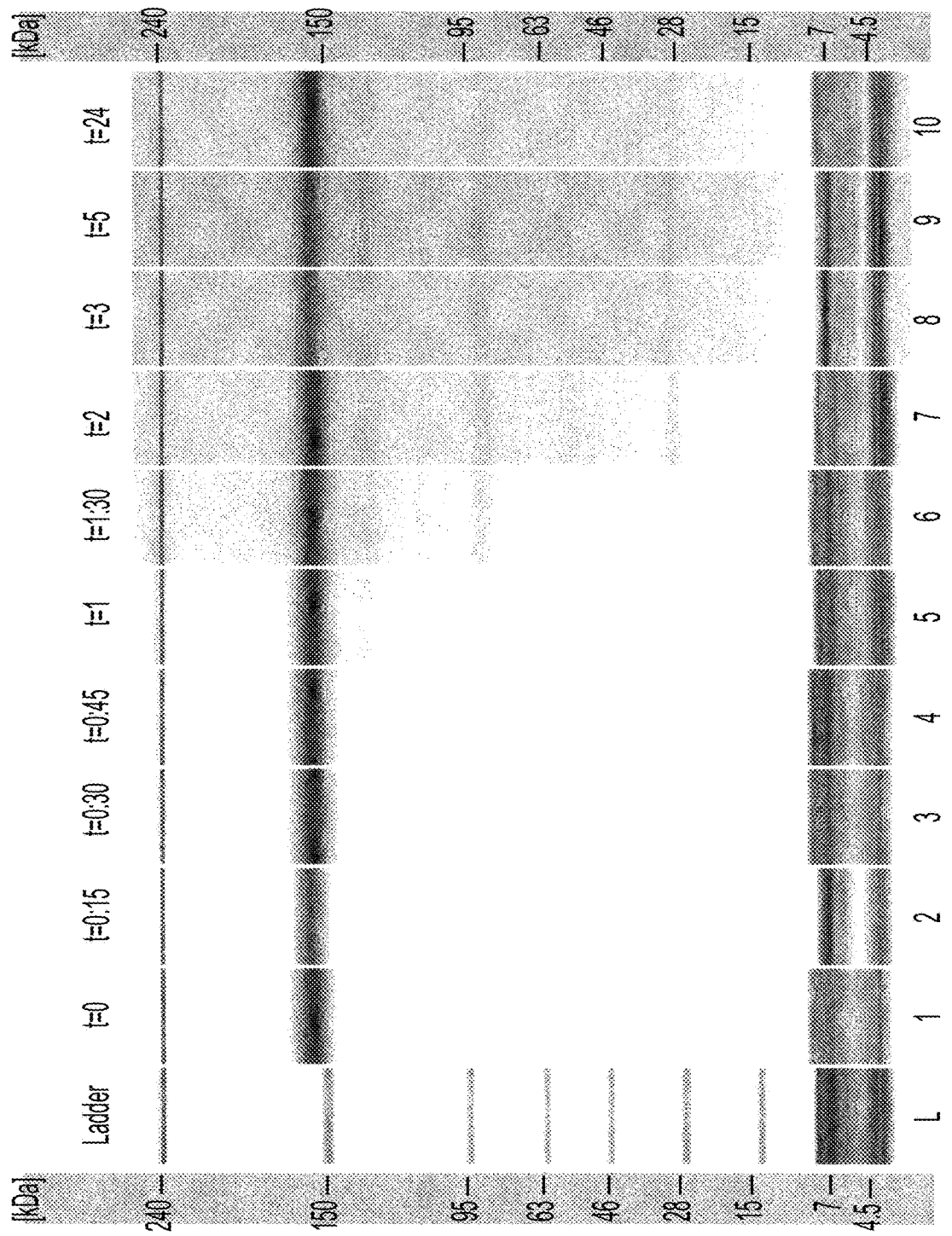
FIG. 39 is a digital gel-like image from Bioanalyzer analysis: 2H7 (Variant A)+1 mM NADPH+5 µM thioredoxin+0.1 µM thioredoxin reductase (recombinant) in 10 mM histidine sulfate+2.6 mM GSSG (oxidized glutathione).

GSSG was added to the ocrelizumab mixture described above at a concentration of 2.6 mM. As shown in FIG. 39, at this concentration GSSG effectively inhibits reduction of ocrelizumab by the thioredoxin system. It is noted, however, that the minimum effective concentration of oxidize glutathione (just as that of the other inhibitors) depends on the actual circumstances, such as, for example, on the nature of the protein (e.g. antibody) produced and the timing of addition. For example, for antibody 2H7 (Variant A) the minimum effective concentration is about 1.3 mM for addition prior to lysis.

8. In Vitro Activity of Enzymatic Reduction System

Figure 40:
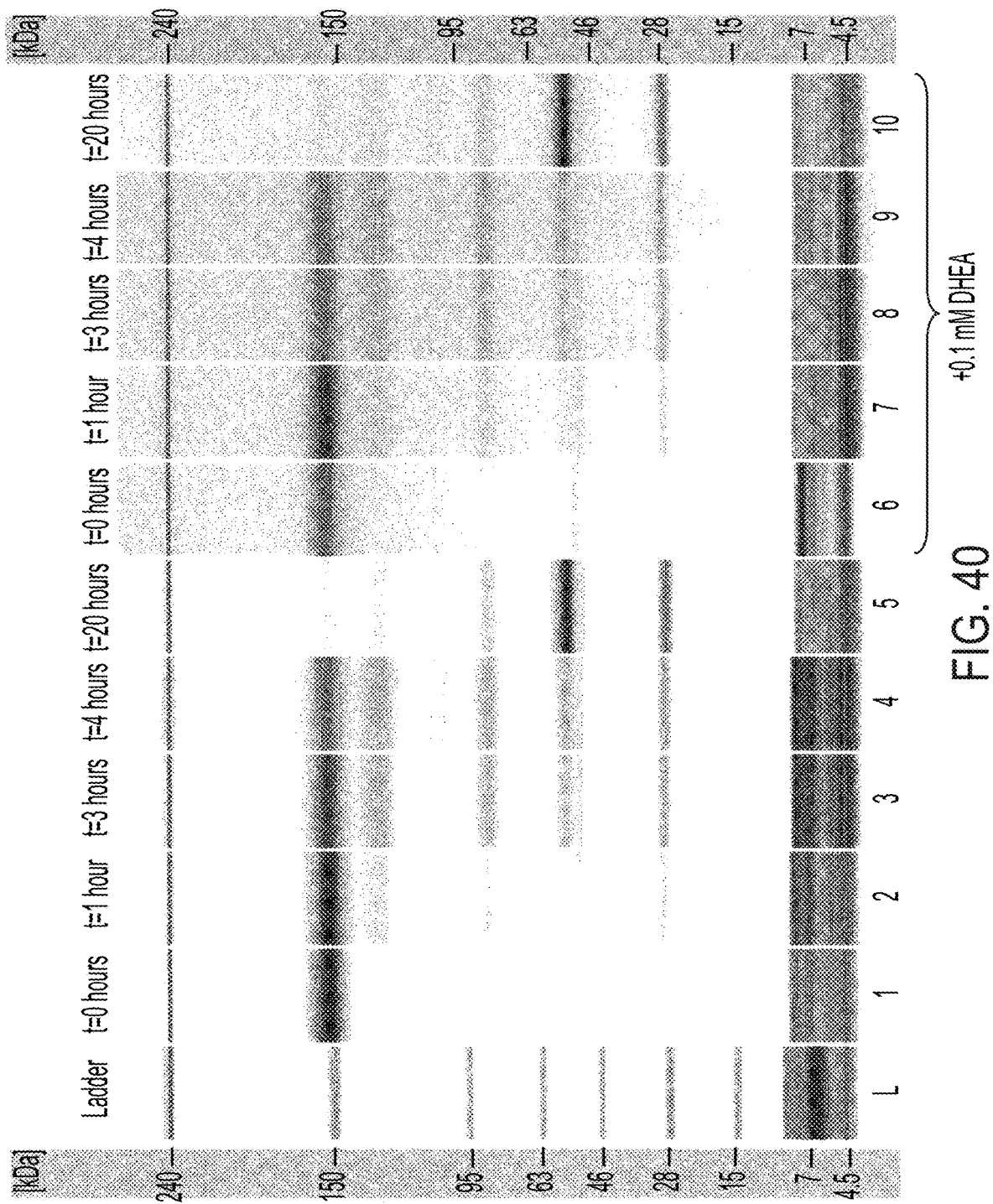
FIG. 40 Reconstructed enzymatic reduction system. 1 mg/ml 2H7 (Variant A)+10 µg/mL hexokinase, 50 µg/mL glucose-6-phosphate dehydrogenase, 5 µM thioredoxin, 0.1

FIG. 40 shows a digital gel-like image from Bioanalyzer analysis (each lane representing a time point) showing that incubation of intact ocrelizumab ("2H7," a humanized anti-CD20 antibody, Variant A) (1 mg/mL) with 10 µg/mL hexokinase, 50 g/mL glucose-6-phosphate dehydrogenase, 5 µM thioredoxin, 0.1 µM thoredoxin reductase, 2 mM glucose, 0.6 mM ATP, 2 mM $Mg^{2+}$, and 2 mM NADP in 50 mM histidine sulfate buffered at pH 7.38 results in the reduction of ocrelizumab in about one hour. Addition of 0.1 mM HDEA, a known glucose-6-phosphate dehydrogenase inhibitor does not inhibit the reduction.

9. In Vitro Activity of Enzymatic Reduction System Requires NADPH

As shown in the digital gel-like image from Bioanalyzer analysis of FIG. 41, incubation of intact ocrelizumab (1 mg/mL) with 5 µM thioredoxin, 0.1 µM thioredoxin reductase, and 2 mM NADP in 50 mM histidine sulfate buffer at pH 7.38 does not result in the reduction of the ocrelizumab antibody. Reduction of ocrelizumab could not occur without hexokinase and glucose-6-phosphate dehydrogenase and their substrates to generate NADPH.

The invention illustratively described herein can suitably be practiced in the absence of any element or elements, limitation or limitations that is not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalent of the invention shown or portion thereof, but it is recognized that various modifications are possible within the scope of the invention claimed. Thus, it should be understood that although the present invention has been specifically disclosed by preferred embodiments and optional features, modifications and variations of the inventions embodied herein disclosed can be readily made by those skilled in the art, and that such modifications and variations are considered to be within the scope of the inventions disclosed herein. The inventions have been described broadly and generically herein. Each of the narrower species and subgeneric groupings falling within the generic disclosure also form the part of these inventions. This includes within the generic description of each of the inventions a proviso or negative limitation that will allow removing any subject matter from the genus, regardless or whether or not the material to be removed was specifically recited. In addition, where features or aspects of an invention are described in terms of the Markush group, those schooled in the art will recognize that the invention is also thereby described in terms of any individual member or subgroup of members of the Markush group. Further, when a reference to an aspect of the invention lists a range of individual members, as for example, 'SEQ ID NO: 1 to SEQ ID NO: 100, inclusive,' it is intended to be equivalent to listing every member of the list individually, and additionally it should be understood that every individual member may be excluded or included in the claim individually.

The steps depicted and/or used in methods herein may be performed in a different order than as depicted and/or stated. The steps are merely exemplary of the order these steps may occur. The steps may occur in any order that is desired such that it still performs the goals of the claimed invention.

From the description of the invention herein, it is manifest that various equivalents can be used to implement the concepts of the present invention without departing from its scope. Moreover, while the invention has been described with specific reference to certain embodiments, a person of ordinary skill in the art would recognize that changes can be made in form and detail without departing from the spirit and the scope of the invention. The described embodiments are considered in all respects as illustrative and not restrictive. It should also be understood that the invention is not limited to the particular embodiments described herein, but is capable of many equivalents, rearrangements, modifications, and substitutions without departing from the scope of the invention. Thus, additional embodiments are within the scope of the invention and within the following claims.

All U.S. patents and applications; foreign patents and applications; scientific articles; books; and publications mentioned herein are hereby incorporated by reference in their entirety as if each individual patent or publication was specifically and individually indicated to be incorporated by reference, including any drawings, figures and tables, as though set forth in full.

What is claimed:

1. A method for the prevention of the reduction of a disulfide bond in an IgG1 monoclonal antibody that binds to HER2 expressed by a recombinant Chinese Hamster Ovary (CHO) host cell, comprising supplementing pre-harvest cell culture fluid or harvested cell culture fluid of the recombinant CHO host cell with a thioredoxin inhibitor, wherein the thioredoxin inhibitor is added in an amount effective to prevent disulfide bond reduction of the antibody that binds to HER2 following completion of a cell culture process, and wherein the antibody that binds to HER2 comprises a light chain variable domain amino acid sequence set forth in SEQ ID NO: 16 and a heavy chain variable domain amino acid sequence set forth in SEQ ID NO: 17.

2. The method of claim 1, wherein the thioredoxin inhibitor is added to the pre-harvest cell culture fluid.

3. The method of claim 1, wherein the thioredoxin inhibitor is added to the harvested cell culture fluid.

4. The method of claim 1, wherein mechanical cell lysis during harvest operations is about 30% to about 70% of total cell lysis.

5. The method of claim 1, wherein the recombinant CHO host cell is cultured in a stirred tank bioreactor system with fed batch culture procedure.

6. The method of claim 1, further comprising the step of recovering the antibody that binds to HER2 from the harvested cell culture fluid.

7. The method of claim 6, further comprising the step of purifying the antibody that binds to HER2 from the harvested cell culture fluid.

8. The method of claim 1, wherein the antibody that binds to HER2 is produced at a scale of greater than 5,000 L.

9. The method of claim 7, further comprising measuring greater than 90% intact antibody that binds HER2 is recovered and purified from the harvested cell culture fluid.

10. A method for the prevention of the reduction of a disulfide bond in an IgG1 monoclonal antibody that binds to HER2 expressed by a recombinant Chinese Hamster Ovary (CHO) host cell, comprising:
   a. supplementing pre-harvest cell culture fluid or harvested cell culture fluid of the recombinant CHO host cell with a thioredoxin inhibitor, wherein the thioredoxin inhibitor is added in an amount effective to prevent disulfide bond reduction of the antibody that binds to HER2 following completion of a cell culture process, and wherein the antibody that binds to HER2 comprises a light chain variable domain amino acid sequence set forth in SEQ ID NO: 16 and a heavy chain variable domain amino acid sequence set forth in SEQ ID NO: 17; and
   b. recovering and purifying the antibody that binds HER2 from the harvested cell culture fluid, and measuring greater than 90% intact antibody that binds HER2 in the purified preparation.

\* \* \* \* \*

```
                              SEQUENCE LISTING

Sequence total quantity: 35
SEQ ID NO: 1            moltype = AA  length = 107
FEATURE                 Location/Qualifiers
REGION                  1..107
                        note = Synthetic Construct
source                  1..107
                        mol_type = protein
                        organism = synthetic construct
SEQUENCE: 1
DIQMTQSPSS LSASVGDRVT ITCRASSSVS YMHWYQQKPG KAPKPLIYAP SNLASGVPSR   60
FSGSGSGTDF TLTISSLQPE DFATYYCQQW SFNPPTFGQG TKVEIKR                107

SEQ ID NO: 2            moltype = AA  length = 122
FEATURE                 Location/Qualifiers
REGION                  1..122
                        note = Synthetic Construct
source                  1..122
                        mol_type = protein
                        organism = synthetic construct
SEQUENCE: 2
EVQLVESGGG LVQPGGSLRL SCAASGYTFT SYNMHWVRQA PGKGLEWVGA IYPGNGDTSY   60
NQKFKGRFTI SVDKSKNTLY LQMNSLRAED TAVYYCARVV YYSNSYWYFD VWGQGTLVTV  120
SS                                                                 122

SEQ ID NO: 3            moltype = AA  length = 107
FEATURE                 Location/Qualifiers
REGION                  1..107
                        note = Synthetic Construct
source                  1..107
                        mol_type = protein
                        organism = synthetic construct
SEQUENCE: 3
DIQMTQSPSS LSASVGDRVT ITCRASSSVS YLHWYQQKPG KAPKPLIYAP SNLASGVPSR   60
FSGSGSGTDF TLTISSLQPE DFATYYCQQW AFNPPTFGQG TKVEIKR                107

SEQ ID NO: 4            moltype = AA  length = 122
FEATURE                 Location/Qualifiers
REGION                  1..122
                        note = Synthetic Construct
source                  1..122
                        mol_type = protein
                        organism = synthetic construct
SEQUENCE: 4
EVQLVESGGG LVQPGGSLRL SCAASGYTFT SYNMHWVRQA PGKGLEWVGA IYPGNGATSY   60
NQKFKGRFTI SVDKSKNTLY LQMNSLRAED TAVYYCARVV YYSASYWYFD VWGQGTLVTV  120
SS                                                                 122

SEQ ID NO: 5            moltype = AA  length = 122
FEATURE                 Location/Qualifiers
REGION                  1..122
                        note = Synthetic Construct
source                  1..122
                        mol_type = protein
                        organism = synthetic construct
SEQUENCE: 5
EVQLVESGGG LVQPGGSLRL SCAASGYTFT SYNMHWVRQA PGKGLEWVGA IYPGNGATSY   60
```

```
NQKFKGRFTI SVDKSKNTLY LQMNSLRAED TAVYYCARVV YYSYRYWYFD VWGQGTLVTV    120
SS                                                                  122

SEQ ID NO: 6           moltype = AA  length = 213
FEATURE                Location/Qualifiers
REGION                 1..213
                       note = Synthetic Construct
source                 1..213
                       mol_type = protein
                       organism = synthetic construct
SEQUENCE: 6
DIQMTQSPSS LSASVGDRVT ITCRASSSVS YMHWYQQKPG KAPKPLIYAP SNLASGVPSR    60
FSGSGSGTDF TLTISSLQPE DFATYYCQQW SFNPPTFGQG TKVEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 7           moltype = AA  length = 452
FEATURE                Location/Qualifiers
REGION                 1..452
                       note = Synthetic Construct
source                 1..452
                       mol_type = protein
                       organism = synthetic construct
SEQUENCE: 7
EVQLVESGGG LVQPGGSLRL SCAASGYTFT SYNMHWVRQA PGKGLEWVGA IYPGNGDTSY    60
NQKFKGRFTI SVDKSKNTLY LQMNSLRAED TAVYYCARVV YYSNSYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 8           moltype = AA  length = 452
FEATURE                Location/Qualifiers
REGION                 1..452
                       note = Synthetic Construct
source                 1..452
                       mol_type = protein
                       organism = synthetic construct
SEQUENCE: 8
EVQLVESGGG LVQPGGSLRL SCAASGYTFT SYNMHWVRQA PGKGLEWVGA IYPGNGDTSY    60
NQKFKGRFTI SVDKSKNTLY LQMNSLRAED TAVYYCARVV YYSNSYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCKVSN KALPAPIAAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 9           moltype = AA  length = 213
FEATURE                Location/Qualifiers
REGION                 1..213
                       note = Synthetic Construct
source                 1..213
                       mol_type = protein
                       organism = synthetic construct
SEQUENCE: 9
DIQMTQSPSS LSASVGDRVT ITCRASSSVS YLHWYQQKPG KAPKPLIYAP SNLASGVPSR    60
FSGSGSGTDF TLTISSLQPE DFATYYCQQW AFNPPTFGQG TKVEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 10          moltype = AA  length = 452
FEATURE                Location/Qualifiers
REGION                 1..452
                       note = Synthetic Construct
source                 1..452
                       mol_type = protein
                       organism = synthetic construct
SEQUENCE: 10
EVQLVESGGG LVQPGGSLRL SCAASGYTFT SYNMHWVRQA PGKGLEWVGA IYPGNGATSY    60
NQKFKGRFTI SVDKSKNTLY LQMNSLRAED TAVYYCARVV YYSASYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCKVSN KALPAPIAAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452
```

```
SEQ ID NO: 11              moltype = AA   length = 452
FEATURE                    Location/Qualifiers
REGION                     1..452
                           note = Synthetic Construct
source                     1..452
                           mol_type = protein
                           organism = synthetic construct
SEQUENCE: 11
EVQLVESGGG LVQPGGSLRL SCAASGYTFT SYNMHWVRQA PGKGLEWVGA IYPGNGATSY     60
NQKFKGRFTI SVDKSKNTLY LQMNSLRAED TAVYYCARVV YYSASYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCAVSN KALPAPIEAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 12              moltype = AA   length = 452
FEATURE                    Location/Qualifiers
REGION                     1..452
                           note = Synthetic Construct
source                     1..452
                           mol_type = protein
                           organism = synthetic construct
SEQUENCE: 12
EVQLVESGGG LVQPGGSLRL SCAASGYTFT SYNMHWVRQA PGKGLEWVGA IYPGNGATSY     60
NQKFKGRFTI SVDKSKNTLY LQMNSLRAED TAVYYCARVV YYSASYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCKVSN AALPAPIAAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 13              moltype = AA   length = 452
FEATURE                    Location/Qualifiers
REGION                     1..452
                           note = Synthetic Construct
source                     1..452
                           mol_type = protein
                           organism = synthetic construct
SEQUENCE: 13
EVQLVESGGG LVQPGGSLRL SCAASGYTFT SYNMHWVRQA PGKGLEWVGA IYPGNGATSY     60
NQKFKGRFTI SVDKSKNTLY LQMNSLRAED TAVYYCARVV YYSASYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCKVSN AALPAPIAAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHWH YTQKSLSLSP GK                                  452

SEQ ID NO: 14              moltype = AA   length = 452
FEATURE                    Location/Qualifiers
REGION                     1..452
                           note = Synthetic Construct
source                     1..452
                           mol_type = protein
                           organism = synthetic construct
SEQUENCE: 14
EVQLVESGGG LVQPGGSLRL SCAASGYTFT SYNMHWVRQA PGKGLEWVGA IYPGNGATSY     60
NQKFKGRFTI SVDKSKNTLY LQMNSLRAED TAVYYCARVV YYSYRYWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCKVSN AALPAPIAAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 15              moltype = AA   length = 452
FEATURE                    Location/Qualifiers
REGION                     1..452
                           note = Synthetic Construct
source                     1..452
                           mol_type = protein
                           organism = synthetic construct
SEQUENCE: 15
EVQLVESGGG LVQPGGSLRL SCAASGYTFT SYNMHWVRQA PGKGLEWVGA IYPGNGDTSY     60
NQKFKGRFTI SVDKSKNTLY LQMNSLRAED TAVYYCARVV YYSNSYWYFD VWGQGTLVTV    120
```

```
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNATYRVVSV LTVLHQDWLN GKEYKCKVSN AALPAPIAAT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 16           moltype = AA   length = 107
FEATURE                 Location/Qualifiers
REGION                  1..107
                        note = Synthetic Construct
source                  1..107
                        mol_type = protein
                        organism = synthetic construct
SEQUENCE: 16
DIQMTQSPSS LSASVGDRVT ITCKASQDVS IGVAWYQQKP GKAPKLLIYS ASYRYTGVPS     60
RFSGSGSGTD FTLTISSLQP EDFATYYCQQ YYIYPYTFGQ GTKVEIK                  107

SEQ ID NO: 17           moltype = AA   length = 119
FEATURE                 Location/Qualifiers
REGION                  1..119
                        note = Synthetic Construct
source                  1..119
                        mol_type = protein
                        organism = synthetic construct
SEQUENCE: 17
EVQLVESGGG LVQPGGSLRL SCAASGFTFT DYTMDWVRQA PGKGLEWVAD VNPNSGGSIY     60
NQRFKGRFTL SVDRSKNTLY LQMNSLRAED TAVYYCARNL GPSFYFDYWG QGTLVTVSS    119

SEQ ID NO: 18           moltype = AA   length = 107
FEATURE                 Location/Qualifiers
REGION                  1..107
                        note = Synthetic Construct
source                  1..107
                        mol_type = protein
                        organism = synthetic construct
SEQUENCE: 18
DIQMTQSPSS LSASVGDRVT ITCRASQDVN TAVAWYQQKP GKAPKLLIYS ASFLYSGVPS     60
RFSGSRSGTD FTLTISSLQP EDFATYYCQQ HYTTPPTFGQ GTKVEIK                  107

SEQ ID NO: 19           moltype = AA   length = 120
FEATURE                 Location/Qualifiers
REGION                  1..120
                        note = Synthetic Construct
source                  1..120
                        mol_type = protein
                        organism = synthetic construct
SEQUENCE: 19
EVQLVESGGG LVQPGGSLRL SCAASGFNIK DTYIHWVRQA PGKGLEWVAR IYPTNGYTRY     60
ADSVKGRFTI SADTSKNTAY LQMNSLRAED TAVYYCSRWG GDGFYAMDYW GQGTLVTVSS   120

SEQ ID NO: 20           moltype = AA   length = 108
FEATURE                 Location/Qualifiers
REGION                  1..108
                        note = Synthetic Construct
source                  1..108
                        mol_type = protein
                        organism = synthetic construct
SEQUENCE: 20
DIQMTQTTSS LSASLGDRVI ISCSASQDIS NYLNWYQQKP DGTVKVLIYF TSSLHSGVPS     60
RFSGSGSGTD YSLTISNLEP EDIATYYCQQ YSTVPWTFGG GTKLEIKR                108

SEQ ID NO: 21           moltype = AA   length = 123
FEATURE                 Location/Qualifiers
REGION                  1..123
                        note = Synthetic Construct
source                  1..123
                        mol_type = protein
                        organism = synthetic construct
SEQUENCE: 21
EIQLVQSGPE LKQPGETVRI SCKASGYTFT NYGMNWVKQA PGKGLKWMGW INTYTGEPTY     60
AADFKRRFTF SLETSASTAY LQISNLKNDD TATYFCAKYP HYYGSSHWYF DVWGAGTTVT   120
VSS                                                                 123

SEQ ID NO: 22           moltype = AA   length = 108
FEATURE                 Location/Qualifiers
REGION                  1..108
                        note = Synthetic Construct
source                  1..108
```

```
                          mol_type = protein
                          organism = synthetic construct
SEQUENCE: 22
DIQMTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKR                  108

SEQ ID NO: 23             moltype = AA   length = 123
FEATURE                   Location/Qualifiers
REGION                    1..123
                          note = Synthetic Construct
source                    1..123
                          mol_type = protein
                          organism = synthetic construct
SEQUENCE: 23
EVQLVESGGG LVQPGGSLRL SCAASGYTFT NYGMNWVRQA PGKGLEWVGW INTYTGEPTY      60
AADFKRRFTF SLDTSKSTAY LQMNSLRAED TAVYYCAKYP HYYGSSHWYF DVWGQGTLVT     120
VSS                                                                  123

SEQ ID NO: 24             moltype = AA   length = 108
FEATURE                   Location/Qualifiers
REGION                    1..108
                          note = Synthetic Construct
source                    1..108
                          mol_type = protein
                          organism = synthetic construct
SEQUENCE: 24
DIQLTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKR                  108

SEQ ID NO: 25             moltype = AA   length = 123
FEATURE                   Location/Qualifiers
REGION                    1..123
                          note = Synthetic Construct
source                    1..123
                          mol_type = protein
                          organism = synthetic construct
SEQUENCE: 25
EVQLVESGGG LVQPGGSLRL SCAASGYDFT HYGMNWVRQA PGKGLEWVGW INTYTGEPTY      60
AADFKRRFTF SLDTSKSTAY LQMNSLRAED TAVYYCAKYP YYYGTSHWYF DVWGQGTLVT     120
VSS                                                                  123

SEQ ID NO: 26             moltype = AA   length = 108
FEATURE                   Location/Qualifiers
REGION                    1..108
                          note = Synthetic Construct
source                    1..108
                          mol_type = protein
                          organism = synthetic construct
SEQUENCE: 26
DIQMTQSPSS LSASVGDRVT ITCRASKTIS KYLAWYQQKP GKAPKLLIYS GSTLQSGVPS      60
RFSGSGSGTD FTLTISSLQP EDFATYYCQQ HNEYPLTFGQ GTKVEIKR                  108

SEQ ID NO: 27             moltype = AA   length = 121
FEATURE                   Location/Qualifiers
REGION                    1..121
                          note = Synthetic Construct
source                    1..121
                          mol_type = protein
                          organism = synthetic construct
SEQUENCE: 27
EVQLVESGGG LVQPGGSLRL SCAASGYSFT GHWMNWVRQA PGKGLEWVGM IHPSDSETRY      60
NQKFKDRFTI SVDKSKNTLY LQMNSLRAED TAVYYCARGI YFYGTTYFDY WGQGTLVTVS     120
S                                                                    121

SEQ ID NO: 28             moltype = AA   length = 214
FEATURE                   Location/Qualifiers
REGION                    1..214
                          note = Synthetic Construct
source                    1..214
                          mol_type = protein
                          organism = synthetic construct
SEQUENCE: 28
DIQMTQSPSS LSASVGDRVT ITCRASKTIS KYLAWYQQKP GKAPKLLIYS GSTLQSGVPS      60
RFSGSGSGTD FTLTISSLQP EDFATYYCQQ HNEYPLTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 29             moltype = AA   length = 451
FEATURE                   Location/Qualifiers
```

```
REGION                   1..451
                         note = Synthetic Construct
source                   1..451
                         mol_type = protein
                         organism = synthetic construct
SEQUENCE: 29
EVQLVESGGG LVQPGGSLRL SCAASGYSFT GHWMNWVRQA PGKGLEWVGM IHPSDSETRY    60
NQKFKDRFTI SVDKSKNTLY LQMNSLRAED TAVYYCARGI YFYGTTYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 30            moltype = DNA   length = 384
FEATURE                  Location/Qualifiers
source                   1..384
                         mol_type = unassigned DNA
                         organism = Escherichia coli
SEQUENCE: 30
atgttacacc aacaacgaaa ccaacacgcc aggcttattc ctgtggagtt atatatgagc    60
gataaaatta ttcacctgac tgacgacagt tttgacacgg atgtactcaa agcggacggg   120
gcgatcctcg tcgatttctg ggcagagtgg tgcggtccgt gcaaaatgat cgccccgatt   180
ctggatgaaa tcgctgacga atatcagggc aaactgaccg ttgcaaaact gaacatcgat   240
caaaaccctg gcactgcgcc gaaatatggc atccgtggta tcccgactct gctgctgttc   300
aaaaacggtg aagtggcggc aaccaaagtg ggtgcactgt ctaaaggtca gttgaaagag   360
ttcctcgacg ctaacctggc gtaa                                          384

SEQ ID NO: 31            moltype = DNA   length = 966
FEATURE                  Location/Qualifiers
source                   1..966
                         mol_type = unassigned DNA
                         organism = Escherichia coli
SEQUENCE: 31
atgggcacga ccaaacacag taaactgctt atcctgggtt caggcccggc gggatacacc    60
gctgctgtct acgcggcgcg cgccaacctg caacctgtgc tgattaccgg catgaaaaa    120
ggcggccaac tgaccaccac cacggaagtg aaaaactggc ctggcgatcc aaacgatctg   180
accggtccgt tattaatgga gcgcatgcac gaacatgcca ccaagtttga aactgagatc   240
attttttgatc atatcaacaa ggtggatctg caaaaccgtc cgttccgtct gaatggcgat   300
aacggcgaat acacttgcga cgcgctgatt attgccaccg gagcttctgc acgctatctc   360
ggcctgccct ctgaagaagc cttaaaggc cgtggggttt ctgcttgtgc aacctgcgac   420
ggtttcttct atcgcaacca gaaagttgcg tcatcgccg gcggcaatac tggcgttgaa   480
gaggcgttgt atctgtctaa catcgcttcg gaagtgcatc tgattcaccg ccgtgacggt   540
ttccgcgcgg aaaaaatcct cattaagcgc ctgatggata agtgagaa cggcaacatc   600
attctgcaca ccaaccgtac gctggaagaa gtgaccggcg atcaaatggg tgtcactggc   660
gttcgtctgc gcgatacgca aaacagcgat aacatcgagt cactcgacgt tgccggtctg   720
tttgttgcta tcggtcacag cccgaatact gcgattttcg aagggcagct ggaactgaa   780
aacggctaca tcaaagtaca gtcgggtatt catggtaatg ccaccagac cagcattcct   840
ggcgtctttg ccgcaggcga cgtgatggat cacatttatc gccaggccat tacttcggcc   900
ggtacaggct gcatggcagc acttgatgcg gaacgctacc tcgatggttt agctgacgca   960
aaataa                                                              966

SEQ ID NO: 32            moltype = DNA   length = 318
FEATURE                  Location/Qualifiers
source                   1..318
                         mol_type = unassigned DNA
                         organism = Mus musculus
SEQUENCE: 32
atggtgaagc tgatcgagag caaggaagct tttcaggagg ccctggccgc cgcgggagac    60
aagcttgtcg tggtggactt ctctgctacg tggtgtggac cttgcaaaat gatcaagccc   120
ttcttccatt ccctctgtga caagtattcc aatgtggtgt tccttgaagt ggatgtggat   180
gactgccagg atgttgctgc agactgtgaa gtcaaatgca tgccgacctt ccagtttat   240
aaaaagggtc aaaaggtggg ggagttctcc ggtgctaaca ggaaaagct tgaagcctct   300
attactgaat atgcctaa                                                 318

SEQ ID NO: 33            moltype = DNA   length = 501
FEATURE                  Location/Qualifiers
source                   1..501
                         mol_type = unassigned DNA
                         organism = Mus musculus
SEQUENCE: 33
atggctcagc ggctcctcct ggggaggttc ctgacctcag tcatctccag gaagcctcct    60
cagggtctgt gggcttccct cacctctaag accctgcaga cccctccagta caatgctcct   120
ggtctaacag taatgcccag cccagcccgg acagtacaca ccaccagagt ctgtttgacg   180
acctttaacg tccaggatgg acctgacttt caagacagag ttgtcaacag tgagacacca   240
gttgttgtgg actttcatgc acagtggtgt ggccctgca agatcctagg accgcggcta   300
gagaagatgt tcgccaagca gcacgggaag gtggtcatgg ccaagtggga cattgacgat   360
cacacagacc ttgccattga atatgaggtg tcagctgtgc ctaccgtgct agccatcaag   420
```

```
aacggggacg tggtggacaa gtttgtgggg atcaaggacg aggaccagct agaagccttc   480
ctgaagaagc tgattggctg a                                             501

SEQ ID NO: 34           moltype = DNA  length = 1494
FEATURE                 Location/Qualifiers
source                  1..1494
                        mol_type = unassigned DNA
                        organism = Mus musculus
SEQUENCE: 34
atgaatggct ccaaagatcc ccctgggtcc tatgacttcg acctgatcat cattggagga   60
ggctcaggag gactggcagc agctaaggag gcagccaaat ttgacaagaa agtgctggtc   120
ttggattttg tcacaccgac tcctcttggg accagatggg gtctcggagg aacgtgtgtg   180
aatgtgggtt gcatacctaa gaagctgatg caccaggcag ctttgctcgg acaagctctg   240
aaagactcgc gcaactatgg ctggaaagtc gaagcacaag tgaagcatga ctgggagaaa   300
atgacggaat ctgtgcagag tcacatcggc tcgctgaact ggggctaccg cgtagctctc   360
cgggagaaaa aggtcgtcta tgagaatgct tacgggaggt tcattggtcc tcacaggatt   420
gtggcgacaa ataacaaagg taagaaaaaa atctattcag cagagcggtt cctcatcgcc   480
acaggtgaga ggccccgcta cctgggcatc cctggagaca aagagtactg catcagcagt   540
gatgatcttt tctccttgcc ttactgcccg gggaagaccc tagtagttgg tgcatcctat   600
gtcgccttgg aatgtgcagg atttctggct ggtatcggct tagacgtcac tgtaatggtg   660
cggtccattc tccttagagg atttgaccaa gacatggcca acaaaatcgg tgaacacatg   720
gaagaacatg gtatcaagtt tataaggcag ttcgtcccaa cgaaaattga acagatcgaa   780
gcaggaacac caggccgact cagggtgact gctcaatcca caaacagcga ggagaccata   840
gagggcgaat taacacagt gttgctggcg gtaggaagag attcttgtac gagaactatt   900
ggcttagaga ccgtgggcgt gaagataaac gaaaaaaccg gaaagatacc cgtcacggat   960
gaagagcaga ccaatgtgcc ttacatctac gccatcggta acatcctgga ggggaagcta   1020
gagctgactc ccgtagccat ccaggcgggg agattgctgg ctcagaggct gtatggaggc   1080
tccaatgtca aatgtgacta tgacaatgtc ccaacgactg tatttactcc tttggaatat   1140
ggctgttgtg gcctctctga agaaaaagcc gtagagaaat ttggggaaga aaatattgaa   1200
gtttaccata gtttctttg gccattgaa tggacagtcc catcccggga taacaacaaa   1260
tgttatgcaa aaataatctg caaccttaaa gacgatgaac gtgcgtggg cttccacgtg   1320
ctgggtccaa acgctggaga ggtgacgcag ggctttgcgg ctgcgctcaa gtgtgggctg   1380
actaagcagc agctggacag caccatcggc atccacccgg tctgtgcaga gatattcaca   1440
acgttgtcag tgacgaagcg ctctggggga gacatcctcc agtctggctg ctga         1494

SEQ ID NO: 35           moltype = DNA  length = 1578
FEATURE                 Location/Qualifiers
source                  1..1578
                        mol_type = unassigned DNA
                        organism = Mus musculus
SEQUENCE: 35
atggcggcga tggtggcggc gatggtggcg gcgctgcgtg gacccagcag gcgcttccgg   60
ccgcggacac gggctctgac acgcgggaca aggggcgagc cgagtgcagc gggagggcag   120
cagagctttg atctcttggt gatcggtggg ggatccggtg gcctagcctt gccaaggaa   180
gctgctcagc tgggaaagaa ggtggctgtg gctgactatg tggaaccttc tccccgaggc   240
accaagtggg gccttggtgg cacctgtgtc aacgtgggtt gcatacccaa gaagctgatg   300
catcaggccg cactgctggg gggcatgatc agagatgctc accactatgg ctgggaggtg   360
gcccagcctg tccaacacaa ctggaagaca atggcagaag ccgtgcaaaa ccatgtgaaa   420
tccttgaact ggggtcatcg cgtccaactg caggacagga aagtcaagta ctttaacatc   480
aaagccagct ttgtggatga gcacacagtt cgcggtgtgg acaaaggcgg gaaggcgact   540
ctgctttcag ctgagcacat tgtcattgct acaggaggac ggccaaggta ccccacacva   600
gtcaaaggag ccctggaata tggaatcaca agtgacgaca tcttctggct gaaggagtcc   660
cctgggaaaa cgttggtggt tggagccagc tatgtggccc tagagtgtgc tggcttcctc   720
actggaattg gactggatac cactgtcatg atgcgcagca tccctctccg aggctttgac   780
cagcaaatgt catctttggt cacagagcac atggagtctc atggcaccca gttcctgaaa   840
ggctgtgtcc cctcccacat caaaaaaactc ccaactaacc agctgcaggt cacttgggag   900
gatcatgctt ctggcaagga agacacaggc acctttgaca ctgtcctgtg gccataggg   960
cgagttccag aaaccaggac tttgaatctg gagaaggctg gcatcagtac caaccctaag   1020
aatcagaaga ttattgtgga tgcccaggag gctacctctg ttccccacat ctatgccatt   1080
ggagatgttg ctgaggggcg gcctgagctg acgcccacag ctatcaaggc aggaaagctt   1140
ctggctcagc ggctctttgg gaaatcctca accttaatgg attacagcaa tgttcccaca   1200
actgtcttta caccactgga gtatggctgt gtggggctgt ctgaggagga ggctgtggct   1260
ctccatggcc aggagcatgt agaggtttac catgcatatt ataagcccct agagttcacg   1320
gtggcggata gggatgcatc acagtgctac ataaagatgg tatgcatgag ggagccccca   1380
caactggtgc tgggcctgca cttccttggc cccaacgctg gagaagtcac ccaaggattt   1440
gctcttggga tcaagtgtgg ggcttcatat gcacaggtga tgcagacagt agggatccat   1500
cccacctgct ctgaggaggt ggtcaagctg cacatctcca agcgctccgg cctggagcct   1560
actgtgactg gttgctga                                                 1578
```